US012331118B2

(12) United States Patent
Poirier et al.

(10) Patent No.: US 12,331,118 B2
(45) Date of Patent: **\*Jun. 17, 2025**

(54) HUMANIZED ANTI-HUMAN-PD-1 ANTIBODY AND METHODS OF USING THEM FOR CANCER TREATMENT

(71) Applicant: OSE IMMUNOTHERAPEUTICS, Nantes (FR)

(72) Inventors: Nicolas Poirier, Treillieres (FR); Caroline Mary, Sainte Pazanne (FR); Virginie Thepenier, Sainte Pazanne (FR); Aurore Morello, Saint Sebastien sur Loire (FR); Sabrina Pengam, Sainte Luce sur Loire (FR)

(73) Assignee: OSE IMMUNOTHERAPEUTICS, Nantes (FR)

( * ) Notice: Subject to any disclaimer, the term of this patent is extended or adjusted under 35 U.S.C. 154(b) by 457 days.

This patent is subject to a terminal disclaimer.

(21) Appl. No.: 17/830,381

(22) Filed: Jun. 2, 2022

(65) Prior Publication Data

US 2022/0332826 A1 Oct. 20, 2022

Related U.S. Application Data

(63) Continuation of application No. 17/414,967, filed as application No. PCT/EP2019/085776 on Dec. 17, 2019, now Pat. No. 11,352,430.

(30) Foreign Application Priority Data

Dec. 21, 2018 (EP) ..................................... 18306801

(51) Int. Cl.
C07K 16/28 (2006.01)
A61K 39/00 (2006.01)
A61K 45/06 (2006.01)
A61P 35/00 (2006.01)

(52) U.S. Cl.
CPC .......... C07K 16/2818 (2013.01); A61K 45/06 (2013.01); A61P 35/00 (2018.01); A61K 2039/505 (2013.01)

(58) Field of Classification Search
CPC ............................ C07K 16/2818; A61P 35/00; A61K 2039/505
See application file for complete search history.

(56) References Cited

U.S. PATENT DOCUMENTS

| 10,434,157 | B2 | 10/2019 | Costantini |
| 11,191,820 | B2 | 12/2021 | Costantini |
| 11,325,959 | B2 | 5/2022 | Conduzorgues |
| 11,352,430 | B2 | 6/2022 | Poirier et al. |
| 2020/0384067 | A1 | 12/2020 | Costantini |
| 2022/0025050 | A1 | 1/2022 | Poirier et al. |
| 2022/0056135 | A1 | 2/2022 | Poirier et al. |
| 2022/0259277 | A1 | 8/2022 | Conduzorgues |
| 2023/0071889 | A1 | 3/2023 | Poirier et al. |

FOREIGN PATENT DOCUMENTS

| EP | 3 176 180 | 6/2017 |
| WO | WO 2014/179664 | 11/2014 |
| WO | WO 2017/055547 | 4/2017 |
| WO | WO 2020/127369 | 6/2020 |
| WO | WO 2020/127373 | 6/2020 |
| WO | WO 2020/127377 | 6/2020 |

OTHER PUBLICATIONS

Chen, D. S. et al. "Oncology Meets Immunology: The Cancer-Immunity Cycle" *Immunity*, Jul. 25, 2013, pp. 1-10, vol. 39.
Rao, M. et al. "Anti-PD-1/PD-L1 therapy for infectious diseases: learning from the cancer paradigm" *International Journal of Infectious Diseases*, 2017, pp. 221-228, vol. 56.
Van Vugt, M. J. H. et al. "Immunogenicity of pembrolizumab in patients with advanced tumors" *Journal for Immuno Therapy of Cancer*, 2019, pp. 1-8, vol. 7, No. 212.
Written Opinion in International Application No. PCT/EP2019/085776, Apr. 3, 2020, pp. 1-7.
Claims as filed for U.S. Appl. No. 17/414,970, filed Jun. 17, 2021, pp. 1-7.
Claims pending for U.S. Appl. No. 17/785,427, filed Jun. 15, 2022, pp. 1-5.
Claims pending for U.S. Appl. No. 17/924,371, filed Nov. 10, 2022, pp. 1-4.

*Primary Examiner* — Elly-Gerald Stoica
(74) *Attorney, Agent, or Firm* — SALIWANCHIK, LLOYD & EISENSCHENK

(57) ABSTRACT

Described herein are humanized anti-PD-1 antibodies, nucleic acids encoding such, and uses thereof in enhancing immune responses by activating T cells and treating diseases such as cancer and an infectious disease.

9 Claims, 17 Drawing Sheets

Specification includes a Sequence Listing.

A

B

C

D

E

A

B

C

A

B

A

B

A

B

A

B

FIGURE 14C and D

SEQUENCE LISTING

<160> NUMBER OF SEQ ID NOS: 51

<210> SEQ ID NO 1
<211> LENGTH: 5
<212> TYPE: PRT
<213> ORGANISM: artificial
<220> FEATURE:
<223> OTHER INFORMATION: HC CDR1

<400> SEQUENCE: 1

His Tyr Ala Met Asn
1               5

<210> SEQ ID NO 2
<211> LENGTH: 17
<212> TYPE: PRT
<213> ORGANISM: artificial
<220> FEATURE:
<223> OTHER INFORMATION: HC CDR2

<400> SEQUENCE: 2

Trp Ile Asn Thr Asn Thr Gly Glu Pro Thr Tyr Ala Gln Gly Phe Thr
1               5                   10                  15

Gly

<210> SEQ ID NO 3
<211> LENGTH: 8
<212> TYPE: PRT
<213> ORGANISM: artificial
<220> FEATURE:
<223> OTHER INFORMATION: HC CDR3

<400> SEQUENCE: 3

Glu Arg Glu Pro Gly Met Asp Ser
1               5

<210> SEQ ID NO 4
<211> LENGTH: 8
<212> TYPE: PRT
<213> ORGANISM: artificial
<220> FEATURE:
<223> OTHER INFORMATION: HC CDR3

<400> SEQUENCE: 4

Glu Arg Glu Pro Gly Met Asp Thr
1               5

<210> SEQ ID NO 5
<211> LENGTH: 8
<212> TYPE: PRT
<213> ORGANISM: artificial
<220> FEATURE:
<223> OTHER INFORMATION: HC CDR3

<400> SEQUENCE: 5

Glu Arg Glu Pro Gly Met Glu Ser
1               5

<210> SEQ ID NO 6
<211> LENGTH: 8
<212> TYPE: PRT
<213> ORGANISM: artificial
<220> FEATURE:
<223> OTHER INFORMATION: HC CDR3

<400> SEQUENCE: 6

```
Glu Arg Glu Pro Gly Met Asp His
1               5

<210> SEQ ID NO 7
<211> LENGTH: 8
<212> TYPE: PRT
<213> ORGANISM: artificial
<220> FEATURE:
<223> OTHER INFORMATION: HC CDR3

<400> SEQUENCE: 7

Glu Arg Glu Pro Gly Met Asp Ala
1               5

<210> SEQ ID NO 8
<211> LENGTH: 8
<212> TYPE: PRT
<213> ORGANISM: artificial
<220> FEATURE:
<223> OTHER INFORMATION: HC CDR3

<400> SEQUENCE: 8

Glu Arg Glu Pro Gly Met Asp Tyr
1               5

<210> SEQ ID NO 9
<211> LENGTH: 8
<212> TYPE: PRT
<213> ORGANISM: artificial
<220> FEATURE:
<223> OTHER INFORMATION: HC CDR3

<400> SEQUENCE: 9

Glu Arg Glu Pro Gly Met Asp Asn
1               5

<210> SEQ ID NO 10
<211> LENGTH: 8
<212> TYPE: PRT
<213> ORGANISM: artificial
<220> FEATURE:
<223> OTHER INFORMATION: HC CDR3

<400> SEQUENCE: 10

Glu Arg Glu Pro Gly Met Asp Glu
1               5

<210> SEQ ID NO 11
<211> LENGTH: 16
<212> TYPE: PRT
<213> ORGANISM: artificial
<220> FEATURE:
<223> OTHER INFORMATION: LC CDR1

<400> SEQUENCE: 11

Arg Ser Ser Gln Ser Leu Val His Ala Asn Gly Asn Thr Tyr Leu Glu
1               5                   10                  15

<210> SEQ ID NO 12
<211> LENGTH: 16
<212> TYPE: PRT
<213> ORGANISM: artificial
<220> FEATURE:
<223> OTHER INFORMATION: LC CDR1

<400> SEQUENCE: 12

Arg Ser Ser Gln Ser Leu Val His Ala Asn Thr Asn Thr Tyr Leu Glu
```

```
<210> SEQ ID NO 13
<211> LENGTH: 7
<212> TYPE: PRT
<213> ORGANISM: artificial
<220> FEATURE:
<223> OTHER INFORMATION: LC CDR2

<400> SEQUENCE: 13

Lys Val Ser Asn Arg Phe Ser
1               5

<210> SEQ ID NO 14
<211> LENGTH: 9
<212> TYPE: PRT
<213> ORGANISM: artificial
<220> FEATURE:
<223> OTHER INFORMATION: LC CDR3

<400> SEQUENCE: 14

Phe Gln Gly Thr His Val Pro Asn Thr
1               5

<210> SEQ ID NO 15
<211> LENGTH: 117
<212> TYPE: PRT
<213> ORGANISM: artificial
<220> FEATURE:
<223> OTHER INFORMATION: HC variable domain

<400> SEQUENCE: 15

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr His Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Arg Glu Pro Gly Met Asp Ser Trp Gly Gln Gly Thr Leu
            100                 105                 110

Val Thr Val Ser Ser
        115

<210> SEQ ID NO 16
<211> LENGTH: 117
<212> TYPE: PRT
<213> ORGANISM: artificial
<220> FEATURE:
<223> OTHER INFORMATION: HC variable domain

<400> SEQUENCE: 16

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr His Tyr
            20                  25                  30

Ala Met Asn Trp Val Arg Gln Ala Pro Gly Gln Gly Leu Glu Trp Met
```

```
            35                  40                  45
Gly Trp Ile Asn Thr Asn Thr Gly Glu Pro Thr Tyr Ala Gln Gly Phe
     50                  55                  60
Thr Gly Arg Phe Val Phe Ser Leu Asp Thr Ser Val Ser Thr Ala Tyr
 65                  70                  75                  80
Leu Gln Ile Ser Ser Leu Lys Ala Glu Asp Thr Ala Val Tyr Tyr Cys
                 85                  90                  95
Ala Arg Glu Arg Glu Pro Gly Met Asp Thr Trp Gly Gln Gly Thr Leu
             100                 105                 110
Val Thr Val Ser Ser
            115

<210> SEQ ID NO 17
<211> LENGTH: 117
<212> TYPE: PRT
<213> ORGANISM: artificial
<220> FEATURE:
<223> OTHER INFORMATION: HC variable domain

<400> SEQUENCE: 17

Gln Ile Gln Leu Val Gln Ser Gly Ser Glu Leu Lys Lys Pro Gly Ala
 1               5                  10                  15
Ser Val Lys Val Ser Cys Lys Ala Ser Gly Tyr Thr Phe Thr His Tyr
             20                  25                  30
Ala Met Asn Trp Val Arg Gln Ala Pro Gly Gln Gly Leu Glu Trp Met
         35                  40                  45
Gly Trp Ile Asn Thr Asn Thr Gly Glu Pro Thr Tyr Ala Gln Gly Phe
     50                  55                  60
Thr Gly Arg Phe Val Phe Ser Leu Asp Thr Ser Val Ser Thr Ala Tyr
 65                  70                  75                  80
Leu Gln Ile Ser Ser Leu Lys Ala Glu Asp Thr Ala Val Tyr Tyr Cys
                 85                  90                  95
Ala Arg Glu Arg Glu Pro Gly Met Glu Ser Trp Gly Gln Gly Thr Leu
             100                 105                 110
Val Thr Val Ser Ser
            115

<210> SEQ ID NO 18
<211> LENGTH: 117
<212> TYPE: PRT
<213> ORGANISM: artificial
<220> FEATURE:
<223> OTHER INFORMATION: HC variable domain

<400> SEQUENCE: 18

Gln Ile Gln Leu Val Gln Ser Gly Ser Glu Leu Lys Lys Pro Gly Ala
 1               5                  10                  15
Ser Val Lys Val Ser Cys Lys Ala Ser Gly Tyr Thr Phe Thr His Tyr
             20                  25                  30
Ala Met Asn Trp Val Arg Gln Ala Pro Gly Gln Gly Leu Glu Trp Met
         35                  40                  45
Gly Trp Ile Asn Thr Asn Thr Gly Glu Pro Thr Tyr Ala Gln Gly Phe
     50                  55                  60
Thr Gly Arg Phe Val Phe Ser Leu Asp Thr Ser Val Ser Thr Ala Tyr
 65                  70                  75                  80
Leu Gln Ile Ser Ser Leu Lys Ala Glu Asp Thr Ala Val Tyr Tyr Cys
                 85                  90                  95
```

```
Ala Arg Glu Arg Glu Pro Gly Met Asp His Trp Gly Gln Gly Thr Leu
                100                 105                 110
Val Thr Val Ser Ser
        115

<210> SEQ ID NO 19
<211> LENGTH: 117
<212> TYPE: PRT
<213> ORGANISM: artificial
<220> FEATURE:
<223> OTHER INFORMATION: HC variable domain

<400> SEQUENCE: 19

Gln Ile Gln Leu Val Gln Ser Gly Ser Glu Leu Lys Lys Pro Gly Ala
1               5                   10                  15
Ser Val Lys Val Ser Cys Lys Ala Ser Gly Tyr Thr Phe Thr His Tyr
            20                  25                  30
Ala Met Asn Trp Val Arg Gln Ala Pro Gly Gln Gly Leu Glu Trp Met
        35                  40                  45
Gly Trp Ile Asn Thr Asn Thr Gly Glu Pro Thr Tyr Ala Gln Gly Phe
    50                  55                  60
Thr Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Tyr Cys
                85                  90                  95
Ala Arg Glu Arg Glu Pro Gly Met Asp Ala Trp Gly Gln Gly Thr Leu
                100                 105                 110
Val Thr Val Ser Ser
        115

<210> SEQ ID NO 20
<211> LENGTH: 117
<212> TYPE: PRT
<213> ORGANISM: artificial
<220> FEATURE:
<223> OTHER INFORMATION: HC variable domain

<400> SEQUENCE: 20

Gln Ile Gln Leu Val Gln Ser Gly Ser Glu Leu Lys Lys Pro Gly Ala
1               5                   10                  15
Ser Val Lys Val Ser Cys Lys Ala Ser Gly Tyr Thr Phe Thr His Tyr
            20                  25                  30
Ala Met Asn Trp Val Arg Gln Ala Pro Gly Gln Gly Leu Glu Trp Met
        35                  40                  45
Gly Trp Ile Asn Thr Asn Thr Gly Glu Pro Thr Tyr Ala Gln Gly Phe
    50                  55                  60
Thr Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Tyr Cys
                85                  90                  95
Ala Arg Glu Arg Glu Pro Gly Met Asp Tyr Trp Gly Gln Gly Thr Leu
                100                 105                 110
Val Thr Val Ser Ser
        115

<210> SEQ ID NO 21
<211> LENGTH: 117
<212> TYPE: PRT
<213> ORGANISM: artificial
```

<220> FEATURE:
<223> OTHER INFORMATION: HC variable domain

<400> SEQUENCE: 21

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr His Tyr
                20                  25                  30

Ala Met Asn Trp Val Arg Gln Ala Pro Gly Gln Gly Leu Glu Trp Met
            35                  40                  45

Gly Trp Ile Asn Thr Asn Thr Gly Glu Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Arg Glu Pro Gly Met Asp Asn Trp Gly Gln Gly Thr Leu
            100                 105                 110

Val Thr Val Ser Ser
        115

<210> SEQ ID NO 22
<211> LENGTH: 117
<212> TYPE: PRT
<213> ORGANISM: artificial
<220> FEATURE:
<223> OTHER INFORMATION: HC variable domain

<400> SEQUENCE: 22

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr His Tyr
                20                  25                  30

Ala Met Asn Trp Val Arg Gln Ala Pro Gly Gln Gly Leu Glu Trp Met
            35                  40                  45

Gly Trp Ile Asn Thr Asn Thr Gly Glu Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Arg Glu Pro Gly Met Asp Glu Trp Gly Gln Gly Thr Leu
            100                 105                 110

Val Thr Val Ser Ser
        115

<210> SEQ ID NO 23
<211> LENGTH: 112
<212> TYPE: PRT
<213> ORGANISM: artificial
<220> FEATURE:
<223> OTHER INFORMATION: LC variable domain

<400> SEQUENCE: 23

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ala
                20                  25                  30

```
Asn Gly Asn Thr Tyr Leu Glu Trp Tyr Gln Gln Arg Pro Gly Gln Ser
            35                  40                  45

Pro Arg Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Thr His Val Pro Asn Thr Phe Gly Gln Gly Thr Lys Leu Glu Ile Lys
                100                 105                 110

<210> SEQ ID NO 24
<211> LENGTH: 112
<212> TYPE: PRT
<213> ORGANISM: artificial
<220> FEATURE:
<223> OTHER INFORMATION: LC variable domain

<400> SEQUENCE: 24

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val His Ala
             20                  25                  30

Asn Thr Asn Thr Tyr Leu Glu Trp Tyr Gln Gln Arg Pro Gly Gln Ser
            35                  40                  45

Pro Arg Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Thr His Val Pro Asn Thr Phe Gly Gln Gly Thr Lys Leu Glu Ile Lys
                100                 105                 110

<210> SEQ ID NO 25
<211> LENGTH: 444
<212> TYPE: PRT
<213> ORGANISM: artificial
<220> FEATURE:
<223> OTHER INFORMATION: HC

<400> SEQUENCE: 25

Gln Ile Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr His Tyr
             20                  25                  30

Ala Met Asn Trp Val Arg Gln Ala Pro Gly Gln Gly Leu Glu Trp Met
            35                  40                  45

Gly Trp Ile Asn Thr Asn Thr Gly Glu Pro Thr Tyr Ala Gln Gly Phe
 50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Glu Arg Glu Pro Gly Met Asp Ser Trp Gly Gln Gly Thr Leu
                100                 105                 110

Val Thr Val Ser Ser Ala Ser Thr Lys Gly Pro Ser Val Phe Pro Leu
            115                 120                 125
```

Ala Pro Cys Ser Arg Ser Thr Ser Glu Ser Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 26
<211> LENGTH: 444
<212> TYPE: PRT
<213> ORGANISM: artificial
<220> FEATURE:
<223> OTHER INFORMATION: HC

<400> SEQUENCE: 26

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr His Tyr
            20                  25                  30

Ala Met Asn Trp Val Arg Gln Ala Pro Gly Gln Gly Leu Glu Trp Met
        35                  40                  45

-continued

Gly Trp Ile Asn Thr Asn Thr Gly Glu Pro Thr Tyr Ala Gln Gly Phe
              50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Glu Arg Glu Pro Gly Met Asp Thr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 27
<211> LENGTH: 444

```
<212> TYPE: PRT
<213> ORGANISM: artificial
<220> FEATURE:
<223> OTHER INFORMATION: HC

<400> SEQUENCE: 27
```

| | | | | | | | | | | | | | | |
|---|---|---|---|---|---|---|---|---|---|---|---|---|---|---|
| Gln | Ile | Gln | Leu | Val | Gln | Ser | Gly | Ser | Glu | Leu | Lys | Lys | Pro | Gly | Ala |
| 1 | | | | 5 | | | | | 10 | | | | | 15 | |

| Ser | Val | Lys | Val | Ser | Cys | Lys | Ala | Ser | Gly | Tyr | Thr | Phe | Thr | His | Tyr |
|---|---|---|---|---|---|---|---|---|---|---|---|---|---|---|---|
| | | | 20 | | | | | 25 | | | | | 30 | | |

| Ala | Met | Asn | Trp | Val | Arg | Gln | Ala | Pro | Gly | Gln | Gly | Leu | Glu | Trp | Met |
|---|---|---|---|---|---|---|---|---|---|---|---|---|---|---|---|
| | | 35 | | | | | 40 | | | | | 45 | | | |

| Gly | Trp | Ile | Asn | Thr | Asn | Thr | Gly | Glu | Pro | Thr | Tyr | Ala | Gln | Gly | Phe |
|---|---|---|---|---|---|---|---|---|---|---|---|---|---|---|---|
| 50 | | | | | 55 | | | | | 60 | | | | | |

| Thr | Gly | Arg | Phe | Val | Phe | Ser | Leu | Asp | Thr | Ser | Val | Ser | Thr | Ala | Tyr |
|---|---|---|---|---|---|---|---|---|---|---|---|---|---|---|---|
| 65 | | | | 70 | | | | | 75 | | | | | 80 | |

| Leu | Gln | Ile | Ser | Ser | Leu | Lys | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Glu | Arg | Glu | Pro | Gly | Met | Glu | Ser | Trp | Gly | Gln | Gly | Thr | Leu |
|---|---|---|---|---|---|---|---|---|---|---|---|---|---|---|---|
| | | | 100 | | | | | 105 | | | | | 110 | | |

| Val | Thr | Val | Ser | Ser | Ala | Ser | Thr | Lys | Gly | Pro | Ser | Val | Phe | Pro | Leu |
|---|---|---|---|---|---|---|---|---|---|---|---|---|---|---|---|
| | | 115 | | | | | 120 | | | | | 125 | | | |

| Ala | Pro | Cys | Ser | Arg | Ser | Thr | Ser | Glu | Ser | Thr | Ala | Ala | Leu | Gly | Cys |
|---|---|---|---|---|---|---|---|---|---|---|---|---|---|---|---|
| 130 | | | | | 135 | | | | | 140 | | | | | |

| Leu | Val | Lys | Asp | Tyr | Phe | Pro | Glu | Pro | Val | Thr | Val | Ser | Trp | Asn | Ser |
|---|---|---|---|---|---|---|---|---|---|---|---|---|---|---|---|
| 145 | | | | 150 | | | | | 155 | | | | | 160 | |

| Gly | Ala | Leu | Thr | Ser | Gly | Val | His | Thr | Phe | Pro | Ala | Val | Leu | Gln | Ser |
|---|---|---|---|---|---|---|---|---|---|---|---|---|---|---|---|
| | | | | 165 | | | | | 170 | | | | | 175 | |

| Ser | Gly | Leu | Tyr | Ser | Leu | Ser | Ser | Val | Val | Thr | Val | Pro | Ser | Ser | Ser |
|---|---|---|---|---|---|---|---|---|---|---|---|---|---|---|---|
| | | | 180 | | | | | 185 | | | | | 190 | | |

| Leu | Gly | Thr | Lys | Thr | Tyr | Thr | Cys | Asn | Val | Asp | His | Lys | Pro | Ser | Asn |
|---|---|---|---|---|---|---|---|---|---|---|---|---|---|---|---|
| | | 195 | | | | | 200 | | | | | 205 | | | |

| Thr | Lys | Val | Asp | Lys | Arg | Val | Glu | Ser | Lys | Tyr | Gly | Pro | Pro | Cys | Pro |
|---|---|---|---|---|---|---|---|---|---|---|---|---|---|---|---|
| | 210 | | | | | 215 | | | | | 220 | | | | |

| Pro | Cys | Pro | Ala | Pro | Glu | Phe | Leu | Gly | Gly | Pro | Ser | Val | Phe | Leu | Phe |
|---|---|---|---|---|---|---|---|---|---|---|---|---|---|---|---|
| 225 | | | | | 230 | | | | | 235 | | | | | 240 |

| Pro | Pro | Lys | Pro | Lys | Asp | Thr | Leu | Met | Ile | Ser | Arg | Thr | Pro | Glu | Val |
|---|---|---|---|---|---|---|---|---|---|---|---|---|---|---|---|
| | | | | 245 | | | | | 250 | | | | | 255 | |

| Thr | Cys | Val | Val | Val | Asp | Val | Ser | Gln | Glu | Asp | Pro | Glu | Val | Gln | Phe |
|---|---|---|---|---|---|---|---|---|---|---|---|---|---|---|---|
| | | | 260 | | | | | 265 | | | | | 270 | | |

| Asn | Trp | Tyr | Val | Asp | Gly | Val | Glu | Val | His | Asn | Ala | Lys | Thr | Lys | Pro |
|---|---|---|---|---|---|---|---|---|---|---|---|---|---|---|---|
| | | 275 | | | | | 280 | | | | | 285 | | | |

| Arg | Glu | Glu | Gln | Phe | Asn | Ser | Thr | Tyr | Arg | Val | Val | Ser | Val | Leu | Thr |
|---|---|---|---|---|---|---|---|---|---|---|---|---|---|---|---|
| | 290 | | | | | 295 | | | | | 300 | | | | |

| Val | Leu | His | Gln | Asp | Trp | Leu | Asn | Gly | Lys | Glu | Tyr | Lys | Cys | Lys | Val |
|---|---|---|---|---|---|---|---|---|---|---|---|---|---|---|---|
| 305 | | | | | 310 | | | | | 315 | | | | | 320 |

| Ser | Asn | Lys | Gly | Leu | Pro | Ser | Ser | Ile | Glu | Lys | Thr | Ile | Ser | Lys | Ala |
|---|---|---|---|---|---|---|---|---|---|---|---|---|---|---|---|
| | | | | 325 | | | | | 330 | | | | | 335 | |

| Lys | Gly | Gln | Pro | Arg | Glu | Pro | Gln | Val | Tyr | Thr | Leu | Pro | Pro | Ser | Gln |
|---|---|---|---|---|---|---|---|---|---|---|---|---|---|---|---|
| | | | 340 | | | | | 345 | | | | | 350 | | |

| Glu | Glu | Met | Thr | Lys | Asn | Gln | Val | Ser | Leu | Thr | Cys | Leu | Val | Lys | Gly |
|---|---|---|---|---|---|---|---|---|---|---|---|---|---|---|---|
| | | | 355 | | | | | 360 | | | | | 365 | | |

| Phe | Tyr | Pro | Ser | Asp | Ile | Ala | Val | Glu | Trp | Glu | Ser | Asn | Gly | Gln | Pro |
|---|---|---|---|---|---|---|---|---|---|---|---|---|---|---|---|
| 370 | | | | | 375 | | | | | 380 | | | | | |

```
Glu Asn Asn Tyr Lys Thr Thr Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
        420                 425                 430

Tyr Thr Gln Lys Ser Leu Ser Leu Ser Pro Gly Lys
        435                 440

<210> SEQ ID NO 28
<211> LENGTH: 444
<212> TYPE: PRT
<213> ORGANISM: artificial
<220> FEATURE:
<223> OTHER INFORMATION: HC

<400> SEQUENCE: 28

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr His Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Glu Pro Thr Tyr Ala Gln Gly Phe
50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Arg Glu Pro Gly Met Asp His Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300
```

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 29
<211> LENGTH: 444
<212> TYPE: PRT
<213> ORGANISM: artificial
<220> FEATURE:
<223> OTHER INFORMATION: HC

<400> SEQUENCE: 29

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr His Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Glu Pro Thr Tyr Ala Gln Gly Phe
50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
            85                  90                  95

Ala Arg Glu Arg Glu Pro Gly Met Asp Ala Trp Gly Gln Gly Thr Leu
        100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
        210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440

<210> SEQ ID NO 30
<211> LENGTH: 444
<212> TYPE: PRT
<213> ORGANISM: artificial
<220> FEATURE:
<223> OTHER INFORMATION: HC

<400> SEQUENCE: 30

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr His Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Arg Glu Pro Gly Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 31
<211> LENGTH: 444
<212> TYPE: PRT
<213> ORGANISM: artificial
<220> FEATURE:
<223> OTHER INFORMATION: HC

<400> SEQUENCE: 31

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr His Tyr
                20                  25                  30

Ala Met Asn Trp Val Arg Gln Ala Pro Gly Gln Gly Leu Glu Trp Met
            35                  40                  45

Gly Trp Ile Asn Thr Asn Thr Gly Glu Pro Thr Tyr Ala Gln Gly Phe
        50                  55                  60

-continued

```
Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Glu Arg Glu Pro Gly Met Asp Asn Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440
```

<210> SEQ ID NO 32
<211> LENGTH: 444
<212> TYPE: PRT
<213> ORGANISM: artificial
<220> FEATURE:
<223> OTHER INFORMATION: HC

<400> SEQUENCE: 32

```
Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr His Tyr
            20                  25                  30

Ala Met Asn Trp Val Arg Gln Ala Pro Gly Gln Gly Leu Glu Trp Met
        35                  40                  45

Gly Trp Ile Asn Thr Asn Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Arg Glu Pro Gly Met Asp Glu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
```

```
                        405                 410                 415
Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440

<210> SEQ ID NO 33
<211> LENGTH: 219
<212> TYPE: PRT
<213> ORGANISM: artificial
<220> FEATURE:
<223> OTHER INFORMATION: LC

<400> SEQUENCE: 33

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ala
            20                  25                  30

Asn Gly Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr His Val Pro Asn Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 34
<211> LENGTH: 219
<212> TYPE: PRT
<213> ORGANISM: artificial
<220> FEATURE:
<223> OTHER INFORMATION: LC

<400> SEQUENCE: 34

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ala
            20                  25                  30

Asn Thr Asn Thr Tyr Leu Glu Trp Tyr Gln Gln Arg Pro Gly Gln Ser
        35                  40                  45
```

```
Pro Arg Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Thr His Val Pro Asn Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
210                 215

<210> SEQ ID NO 35
<211> LENGTH: 327
<212> TYPE: PRT
<213> ORGANISM: artificial
<220> FEATURE:
<223> OTHER INFORMATION: HC constant domain

<400> SEQUENCE: 35

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
             115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190
```

```
Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 36
<211> LENGTH: 107
<212> TYPE: PRT
<213> ORGANISM: artificial
<220> FEATURE:
<223> OTHER INFORMATION: LC contant domain

<400> SEQUENCE: 36

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 37
<211> LENGTH: 30
<212> TYPE: PRT
<213> ORGANISM: artificial
<220> FEATURE:
<223> OTHER INFORMATION: HFR1

<400> SEQUENCE: 37

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr
            20                  25                  30

<210> SEQ ID NO 38
<211> LENGTH: 14
<212> TYPE: PRT
<213> ORGANISM: artificial
```

<220> FEATURE:
<223> OTHER INFORMATION: HFR2

<400> SEQUENCE: 38

Trp Val Arg Gln Ala Pro Gly Gln Gly Leu Glu Trp Met Gly
1               5                   10

<210> SEQ ID NO 39
<211> LENGTH: 32
<212> TYPE: PRT
<213> ORGANISM: artificial
<220> FEATURE:
<223> OTHER INFORMATION: HFR3

<400> SEQUENCE: 39

Arg Phe Val Phe Ser Leu Asp Thr Ser Val Ser Thr Ala Tyr Leu Gln
1               5                   10                  15

Ile Ser Ser Leu Lys Ala Glu Asp Thr Ala Val Tyr Tyr Cys Ala Arg
            20                  25                  30

<210> SEQ ID NO 40
<211> LENGTH: 11
<212> TYPE: PRT
<213> ORGANISM: artificial
<220> FEATURE:
<223> OTHER INFORMATION: HFR4

<400> SEQUENCE: 40

Trp Gly Gln Gly Thr Leu Val Thr Val Ser Ser
1               5                   10

<210> SEQ ID NO 41
<211> LENGTH: 23
<212> TYPE: PRT
<213> ORGANISM: artificial
<220> FEATURE:
<223> OTHER INFORMATION: LFR1

<400> SEQUENCE: 41

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 42
<211> LENGTH: 15
<212> TYPE: PRT
<213> ORGANISM: artificial
<220> FEATURE:
<223> OTHER INFORMATION: LFR2

<400> SEQUENCE: 42

Trp Tyr Gln Gln Arg Pro Gly Gln Ser Pro Arg Leu Leu Ile Tyr
1               5                   10                  15

<210> SEQ ID NO 43
<211> LENGTH: 32
<212> TYPE: PRT
<213> ORGANISM: artificial
<220> FEATURE:
<223> OTHER INFORMATION: LFR3

<400> SEQUENCE: 43

Gly Val Pro Asp Arg Phe Ser Gly Ser Gly Ser Gly Thr Asp Phe Thr
1               5                   10                  15

```
Leu Lys Ile Ser Arg Val Glu Ala Glu Asp Val Gly Val Tyr Tyr Cys
            20                  25                  30
```

<210> SEQ ID NO 44
<211> LENGTH: 10
<212> TYPE: PRT
<213> ORGANISM: artificial
<220> FEATURE:
<223> OTHER INFORMATION: LFR4

<400> SEQUENCE: 44

```
Phe Gly Gln Gly Thr Lys Leu Glu Ile Lys
1               5                   10
```

<210> SEQ ID NO 45
<211> LENGTH: 19
<212> TYPE: PRT
<213> ORGANISM: artificial
<220> FEATURE:
<223> OTHER INFORMATION: signal peptide

<400> SEQUENCE: 45

```
Met Asp Trp Leu Trp Asn Leu Leu Phe Leu Met Ala Ala Ala Gln Ser
1               5                   10                  15

Ile Gln Ala
```

<210> SEQ ID NO 46
<211> LENGTH: 19
<212> TYPE: PRT
<213> ORGANISM: artificial
<220> FEATURE:
<223> OTHER INFORMATION: signal peptide

<400> SEQUENCE: 46

```
Met Lys Leu Pro Val Arg Leu Leu Val Leu Met Phe Trp Ile Pro Ala
1               5                   10                  15

Ser Ser Ser
```

<210> SEQ ID NO 47
<211> LENGTH: 330
<212> TYPE: PRT
<213> ORGANISM: artificial
<220> FEATURE:
<223> OTHER INFORMATION: IgG1m-N298A

<400> SEQUENCE: 47

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 48
<211> LENGTH: 351
<212> TYPE: DNA
<213> ORGANISM: artificial
<220> FEATURE:
<223> OTHER INFORMATION: VH HK

<400> SEQUENCE: 48

```
cagatccagc tggtgcagag cggctctgag ctgaagaagc caggcgcttc tgtgaaggtg    60
tcctgcaagg ccagcggcta caccttcaca cactatgcta tgaattgggt gagacaggct   120
ccaggacagg gactggagtg gatgggctgg atcaacacca atacaggcga gcctacctac   180
gctcagggct ttacaggccg cttcgtgttt tctctggata cctccgtgag cacagcctat   240
ctgcagatct ccagcctgaa ggctgaggac accgccgtgt actattgtgc tagggagagg   300
gagccaggaa tggataactg ggacagggc accctggtga cagtgtcttc c              351
```

<210> SEQ ID NO 49
<211> LENGTH: 336
<212> TYPE: DNA
<213> ORGANISM: artificial
<220> FEATURE:
<223> OTHER INFORMATION: VL LD

<400> SEQUENCE: 49

```
gacgtggtca tgacacagag cccactgtct ctgcctgtga ccctgggaca gccagcctct    60
atctcctgca gatccagcca gtctctggtg cacgctaaca ccaatacata cctggagtgg   120
tatcagcaga ggccaggaca gtccccaagg ctgctgatct acaaggtgtc caacagattc   180
agcggagtgc cagaccgctt tagcggatct ggatccggaa ccgacttcac cctgaagatc   240
```

```
tccagggtgg aggctgagga tgtgggcgtg tactattgtt tccagggcac ccatgtgcct      300
aatacatttg gccagggcac caagctggag atcaag                                336

<210> SEQ ID NO 50
<211> LENGTH: 1335
<212> TYPE: DNA
<213> ORGANISM: artificial
<220> FEATURE:
<223> OTHER INFORMATION: CH HK

<400> SEQUENCE: 50
cagatccagc tggtgcagag cggctctgag ctgaagaagc caggcgcttc tgtgaaggtg      60
tcctgcaagg ccagcggcta caccttcaca cactatgcta tgaattgggt gagacaggct      120
ccaggacagg gactggagtg gatgggctgg atcaacacca atacaggcga gcctacctac      180
gctcagggct ttacaggccg cttcgtgttt tctctggata cctccgtgag cacagcctat      240
ctgcagatct ccagcctgaa ggctgaggac accgccgtgt actattgtgc tagggagagg      300
gagccaggaa tggataactg gggacagggc accctggtga cagtgtcttc cgctagcacc      360
aagggcccat cggtcttccc cctggcgccc tgctccagga gcacctccga gagcacagcc      420
gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacgaagac ctacacctgc      600
aacgtagatc acaagcccag caacaccaag gtggacaaga gagttgagtc caaatatggt      660
cccccatgcc caccatgccc agcacctgag ttcctggggg gaccatcagt cttcctgttc      720
cccccaaaac ccaaggacac tctcatgatc tcccggaccc ctgaggtcac gtgcgtggtg      780
gtggacgtga gccaggaaga ccccgaggtc cagttcaact ggtacgtgga tggcgtggag      840
gtgcataatg ccaagacaaa gccgcggag gagcagttca acagcacgta ccgtgtggtc      900
agcgtcctca ccgtcctgca ccaggactgg ctgaacggca aggagtacaa gtgcaaggtc      960
tccaacaaag gcctcccgtc ctccatcgag aaaaccatct ccaaagccaa agggcagccc      1020
cgagagccac aggtgtacac cctgccccca tcccaggagg atgaccaa gaaccaggtc      1080 agcctgacct gcctggtcaa aggcttctac cccagcgaca tcgccgtgga gtgggagagc      1140
aatgggcagc cggagaacaa ctacaagacc acgcctcccg tgctggactc cgacggctcc      1200
ttcttcctct acagcaggct aaccgtggac aagagcaggt ggcaggaggg gaatgtcttc      1260
tcatgctccg tgatgcatga ggctctgcac aaccactaca cacagaagag cctctccctg      1320
tctccgggta aatga                                                       1335

<210> SEQ ID NO 51
<211> LENGTH: 660
<212> TYPE: DNA
<213> ORGANISM: artificial
<220> FEATURE:
<223> OTHER INFORMATION: CL LD

<400> SEQUENCE: 51
gacgtggtca tgacacagag cccactgtct ctgcctgtga ccctgggaca gccagcctct      60
atctcctgca gatccagcca gtctctggtg cacgctaaca ccaatacata cctggagtgg      120
tatcagcaga ggccaggaca gtccccaagg ctgctgatct acaaggtgtc caacagattc      180
agcggagtgc cagaccgctt tagcggatct ggatccggaa ccgacttcac cctgaagatc      240
```

```
tccagggtgg aggctgagga tgtgggcgtg tactattgtt tccagggcac ccatgtgcct    300
aatacatttg gccagggcac caagctggag atcaagcgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttag    660
```

HUMANIZED ANTI-HUMAN-PD-1 ANTIBODY AND METHODS OF USING THEM FOR CANCER TREATMENT

CROSS-REFERENCE TO RELATED APPLICATIONS

This application is a continuation of U.S. application Ser. No. 17/414,967, filed Jun. 17, 2021, now U.S. Pat. No. 11,352,430, which is the U.S. national stage application of International Patent Application No. PCT/EP2019/085776, filed Dec. 17, 2019.

The Sequence Listing for this application is labeled "Seq-List.txt" which was created on Jun. 3, 2021 and is 61 KB. The entire content of the sequence listing is incorporated herein by reference in its entirety.

FIELD OF THE INVENTION

The present invention relates to the field of immunology and immunotherapy, particularly in the treatment of human diseases. More specifically, the present invention relates to a humanized anti-human PD-1 antibody or antigen binding fragment thereof, useful in the treatment of human diseases.

BACKGROUND OF THE INVENTION

Programmed cell death protein 1 (PD-1, also known as CD279) is a cell surface protein molecule that belongs to the immunoglobulin superfamily. PD-1 is expressed on T and B lymphocytes and macrophages, and plays a role in cell fate and differentiation. Particularly, PD-1, functioning as an immune checkpoint, plays an important role in down-regulating the immune system by preventing the activation of T-cells, which in turn reduces autoimmunity and promotes self-tolerance. Two ligands for PD-1 have been identified, PD-L1 and PD-L2, that have been shown to downregulate T cell activation, inducing co-inhibitory signals in T cells and promoting their apoptosis, anergy, and functional exhaustion, upon binding to PD-1 (Freeman et al. (2000) J Exp Med 192: 1027-34; Latchman et al. (2001) Nat Immunol 2:261-8; Carter et al. (2002) Eur J Immunol 32:634-43). The ligands PD-L1 and PD-L2 are not expressed in normal human cells, but may be abundant in a variety of human cancers (Dong et al. (2002) Nat Med 8:787-9, Brahmer et al., N Eng J Med, 366(26), 2012; Topalian et al., N Eng J Med, 366(26), 2012; Wolchok et al., N Engl J Med. 2013 Jul 11; 369(2): 122-133).). PD-L1 is more widely expressed than PD-L2 and is expressed by a variety of hematopoietic and non-hematopoietic cells.

Tumors, microbes and viruses have exploited co-inhibitory pathways such as PD-L1/PD-1 to evade immune defense and surveillance by creating an immune suppressive microenvironment. Particularly, PD-L1/PD-1 pathway caused by tumors, microbes or viruses can achieve the escape of host immunological surveillance through a variety of mechanisms, including promoting T cell inactivation, fatigue, unresponsiveness and apoptosis, inducing T-reg cell amplification, and enhancing intrinsic ability of tumor to resist killing and apoptosis. The interaction of PD-1 and PD-L1 mediated by cancer cells also leads to the reduction of tumor infiltrating lymphocytes and the inhibition of T cell proliferation mediated by T cell receptors by reducing signals downstream of TCR, resulting in decreased activation and cytokine production (Dong et al. J. Mol. Med. 2003, 81: 281-7; Blank et al. Cancer Immunol. Immunother. 2005, 54: 307-314; Konishi et al. Clin. Cancer Res. 2004, 10: 5094-100). The expression of PD-1 on tumor infiltrating lymphocytes or tumor cells has been found in a number of primary tumor biopsies (Ribas A. Cancer Discov. 2015, 5(9):915-9).

Given its immunosuppressive role, PD-1 inhibitors have been developed to counteract this deleterious effect on human immune system. Such PD-1 inhibitors are believed to activate the immune system to attack tumors or infected cells and therefore may be used to treat cancer and diseases. Indeed, strategies using inhibitors of PD-1 or PD-L1 to disrupt their interaction have shown potential for improving cancer immunotherapy (Brahmer et al., N Eng J Med, 366(26), 2012; Powles et al., Nature, 515(7528), 2014; Topalian et al., N Eng J Med, 366(26), 2012; Ansell, Curr Opin Hematol, 22(4), 2015). Particularly, blockade of the interactions between PD-1 and its ligands enhances tumor-specific CD8 T-cell immunity that is capable of eliminating tumor cells (Topalian S. et al. Curr Opin Immunol. 2012, 24(2):207-12). The inhibitory effect of PD-1 is also accomplished through a dual mechanism of promoting apoptosis in antigen specific T-cells in lymph nodes while simultaneously reducing apoptosis in regulatory T cells.

The use of monoclonal antibodies ("mAbs") specific for PD-1/PD-L1 blockade are known in the art to counteract the immunosuppressive effect of PD-1/PD-L1 signaling pathway. However, significant practical problems have stood in the way of their widespread in vivo use in humans. A major concern is that monoclonal antibodies of non-human origin often are immunogenic, thereby limiting their effectiveness and, in some cases, causing dangerous allergic reactions. The immune response to such foreign mAbs includes the production of specific, high affinity antibodies which bind to and effect elimination of the mAbs, thereby substantially reducing the mAb's effectiveness by promoting its clearance from the body and inhibiting its ability to bind to the targeted antigen. To overcome this problem, it is possible to humanize non-human antibody of interest to reduce immunogenicity to humans, while retaining the specificity and affinity of the parental non-human antibody (classically a murine antibody). Such humanized antibody typically comprises one or more variable domains in which the antigen binding domains are derived from the non-human antibody, and framework regions derived from human or humanized antibody sequences.

Thus, there is a need to develop humanized antibodies to provide improved agents for safe immunotherapy, notably against cancer, targeting human PD-1.

SUMMARY OF THE INVENTION

The present invention is based on the development of a humanized antibody specifically targeting human PD-1, which show high binding affinity to PD-1 and a strong competition with its ligand PDL-1 and/or PDL-2. This humanized antibody has been engineered to present a high manufacturability and production yield in mammalian cell-based production systems. This humanized antibody is in particular called herein "HKLD".

Further, the applicant has observed a substantial and unexpected effect of the antibody leading to a phagocytosis action of macrophages towards tumoral cells which do not express PD-L1, with promising efficiency of this antibody notably for treating PD-L1 negative tumors and/or patients suffering of a deficiency of their T cell immune response.

Strong benefic and unexpected effects are shown and explained notably at the beginning of the detailed description and in the examples.

In a first aspect, the humanized monoclonal anti-human-PD-1 antibody or an antigen-binding fragment thereof comprising:
(i) a heavy chain variable domain comprising HCDR1 comprising or consisting of an amino acid sequence of SEQ ID NO: 1, HCDR2 comprising or consisting of an amino acid sequence of SEQ ID NO: 2 and HCDR3 comprising or consisting of an amino acid sequence of SEQ ID NO: 9, and
(ii) a light chain variable domain comprising LCDR1 comprising or consisting of an amino acid sequence of SEQ ID NO: 12, LCDR2 comprising or consisting of an amino acid sequence of SEQ ID NO: 13 and LCDR3 comprising or consisting of an amino acid sequence of SEQ ID NO: 14, wherein the antibody or antigen binding fragment thereof is an antagonist of the binding of human PD-L1 and/or PD-L2 to human PD-1.

In a second aspect, the humanized monoclonal anti-human-PD-1 antibody or an antigen-binding fragment thereof comprises (a) a VH comprising or consisting of an amino acid sequence selected from the group consisting of SEQ ID NO: 21; and (b) a VL comprising or consisting of an amino acid sequence of SEQ ID NO: 24.

Preferably, the antibody or antigen binding fragment thereof is an antagonist of the binding of human PD-L1 and/or PD-L2 to human PD-1.

In a particular aspect, the antibody or antigen-binding fragment thereof comprises—(a) a heavy chain comprising or consisting of an amino acid sequence selected from the group consisting of SEQ ID NO: 31, optionally with one, two or three modification(s) selected from substitution(s), addition(s), deletion(s) and any combination thereof at any position but positions 7, 16, 17, 20, 33, 38, 43, 46, 62, 63, 65, 69, 73, 76, 78, 80, 84, 85, 88, 93, 95, 96, 97, 98, 100, 101, 105, 106 and 112 of SEQ ID NO: 31, and (b) a light chain comprising or consisting of an amino acid sequence of SEQ ID NO: 34, optionally with one, two or three modification(s) selected from substitution(s), addition(s), deletion(s) and any combination thereof at any position but positions 3, 4, 7, 14, 17, 18, 28, 29, 33, 34, 39, 42, 44, 50, 81, 88, 94, 97, 99 and 105 of SEQ ID NO: 34.

In a particular aspect, the antibody or antigen-binding fragment thereof comprises a light chain constant domain derived from a human kappa light chain constant domain and a heavy chain constant domain derived from a human IgG1, IgG2, IgG3 or IgG4 heavy chain constant domain.

In a more specific aspect, the antibody or antigen-binding fragment thereof comprises a light chain constant domain derived from a human kappa light chain constant domain and a heavy chain constant domain derived from a human IgG1 heavy chain constant domain, optionally with a substitution or a combination of substitutions selected from the group consisting of T250Q/M428L; M252Y/S254T/T256E+H433K/N434F; E233P/L234V/L235A/G236A+A327G/A330S/P331S; E333A; S239D/A330L/1332E; P2571/Q311; K326W/E333S; S239D/1332E/G236A; N297A; L234A/L235A; N297A+M252Y/S254T/T256E; K322A and K444A, preferably selected from the group consisting of N297A optionally in combination with M252Y/S254T/T256E, and L234A/L235A.

In another more specific aspect, the antibody or antigen-binding fragment thereof comprises a light chain constant domain derived from a human kappa light chain constant domain and a heavy chain constant domain derived from a human IgG4 heavy chain constant domain, optionally with a substitution or a combination of substitutions selected from the group consisting of S228P; L234A/L235A, S228P+M252Y/S254T/T256E and K444A.

Preferably, the antibody or antigen-binding fragment thereof specifically binds to human PD-1 with a binding affinity constant (KD) for a human PD-1 equal or lower than $10^{-7}$ M, the affinity being preferably determined by biosensor analysis.

Particularly, the antibody or antigen-binding fragment thereof has a humanness (T20) equal or greater than 85%, preferably equal or greater than 88% and/or which has a high production yield in mammalian cells.

In a second aspect, the invention concerns an isolated nucleic acid molecule or a group of isolated nucleic acid molecules encoding the antibody or antigen-binding fragment thereof as disclosed herein.

In a third aspect, the invention concerns a vector comprising the isolated nucleic acid molecule or the group of isolated nucleic acid molecules as disclosed herein.

The invention also concerns a host cell comprising the isolated nucleic acid molecule and/or the group of isolated nucleic acid molecules and/or the vector according to the invention.

In another aspect, the invention relates to a method for producing the antibody or antigen-binding fragment thereof, comprising a step of culturing a host cell as disclosed herein and optionally a step of isolating the antibody or antigen-binding fragment.

In another aspect, the invention concerns a pharmaceutical composition comprising an antibody or an antigen-binding fragment thereof and/or the isolated nucleic acid molecule and/or a group of isolated nucleic acid molecules and/or the vector and/or the host cell as disclosed herein and a pharmaceutically acceptable carrier.

Optionally, the pharmaceutical composition further comprises an additional therapeutic agent, preferably selected in the group consisting of alkylating agents, angiogenesis inhibitors, antibodies, in particular anti-tumor targeting antibodies, antimetabolites, antimitotics, antiproliferatives, antivirals, aurora kinase inhibitors, apoptosis promoters (for example, Bcl-2 family inhibitors), activators of death receptor pathway, Bcr-Abl kinase inhibitors, BiTE (Bi-Specific T cell Engager) antibodies, antibody drug conjugates, biologic response modifiers, Bruton's tyrosine kinase (BTK) inhibitors, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNAs, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteasome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, hypomethylating agents, checkpoints inhibitors, peptide vaccine and the like, epitopes or neoepitopes from tumor antigens, as well as combinations of one or more of these agents.

Particularly, the antibody or antigen-binding fragment thereof, the pharmaceutical composition, the isolated nucleic acid molecule or the group of isolated nucleic acid molecules, the vector, or the host cell are for use as a medicament.

Optionally, the antibody or antigen-binding fragment thereof, the pharmaceutical composition, the isolated nucleic acid molecule or the group of isolated nucleic acid molecules, the vector, or the host cell are for use in combination with radiotherapy or an additional therapeutic agent, preferably selected in the group consisting of alkylating agents, angiogenesis inhibitors, antibodies, in particular anti-tumor targeting antibodies, antimetabolites, antimitotics, antiproliferatives, antivirals, aurora kinase inhibitors, apoptosis promoters (for example, Bcl-2 family inhibitors), activators of death receptor pathway, Bcr-Abl kinase inhibitors, BiTE (Bi-Specific T cell Engager) antibodies, antibody drug conjugates, biologic response modifiers, Bruton's tyrosine kinase (BTK) inhibitors, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNAs, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteasome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, hypomethylating agents, checkpoints inhibitors, peptide vaccine and the like, epitopes or neoepitopes from tumor antigens, as well as combinations of one or more of these agents.

In one aspect, the antibody or antigen-binding fragment thereof, the pharmaceutical composition, the isolated nucleic acid molecule or the group of isolated nucleic acid molecules, the vector, or the host cell for use as a medicament are for use in the prevention or treatment of cancer. Preferably, the cancer is selected from the group consisting of a hematologic malignancy or a solid tumor with expression of PD-1 and/or PD-L1 such as a cancer selected from the group consisting of hematolymphoid neoplasms, angioimmunoblastic T cell lymphoma, myelodysplastic syndrome, and acute myeloid leukemia, a cancer induced by virus or associated with immunodeficiency such as a cancer selected from the group consisting of Kaposi sarcoma (e.g., associated with Kaposi sarcoma herpes virus); cervical, anal, penile and vulvar squamous cell cancer and oropharyngeal cancers (e.g., associated with human papilloma virus); B cell non-Hodgkin lymphomas (NHL) including diffuse large B-cell lymphoma, Burkitt lymphoma, plasmablastic lymphoma, primary central nervous system lymphoma, HHV-8 primary effusion lymphoma, classic Hodgkin lymphoma, and lymphoproliferative disorders (e.g., associated with Epstein-Barr virus (EBV) and/or Kaposi sarcoma herpes virus); hepatocellular carcinoma (e.g., associated with hepatitis B and/or C viruses); Merkel cell carcinoma (e.g., associated with Merkel cell polyoma virus (MPV)); and cancer associated with human immunodeficiency virus infection (HIV) infection, and a cancer selected from the group consisting of metastatic or not metastatic, Melanoma, malignant mesothelioma, Non-Small Cell Lung Cancer, Renal Cell Carcinoma, Hodgkin's Lymphoma, Head and Neck Cancer, Urothelial Carcinoma, Colorectal Cancer, Hepatocellular Carcinoma, Small Cell Lung Cancer, Metastatic Merkel Cell Carcinoma, Gastric or Gastroesophageal cancers and Cervical Cancer.

In a particular aspect, the antibody or antigen-binding fragment thereof, the pharmaceutical composition, the isolated nucleic acid molecule or the group of isolated nucleic acid molecules, the vector, or the host cell is for use for treating a cancer wherein the tumor cells are PD-L1 negative. Preferably, the antibody or antigen-binding fragment thereof, the pharmaceutical composition, the isolated nucleic acid molecule or the group of isolated nucleic acid molecules, the vector, or the host cell for use as a medicament are for use in the prevention or treatment of an infectious disease, preferably a chronic infectious disease, even more preferably caused by a virus selected from the group consisting of HIV, hepatitis virus, herpes virus, adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

In a particular aspect, the antibody or antigen-binding fragment thereof, the pharmaceutical composition, the isolated nucleic acid molecule or the group of isolated nucleic acid molecules, the vector, or the host cell is for use for treating patients with a lymphopenic disorder.

In a particular aspect, the antibody or antigen-binding fragment thereof, the pharmaceutical composition, the isolated nucleic acid molecule or the group of isolated nucleic acid molecules, the vector, or the host cell for use as a drug for treating a subject that is immunosuppressed, immunocompromised or immunodepressed. In another particular aspect, the subject has a high mutation burden and neoantigen density.

Figure 1:
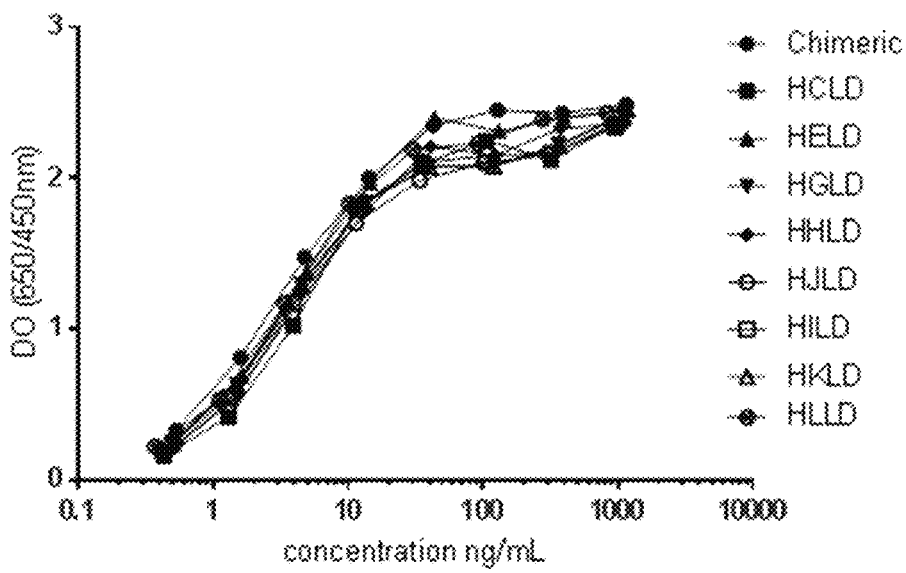
FIG. 1: Binding of the different humanized anti-PD1 variant antibodies on human PD1 by ELISA and FACS: A: ELISA analysis of the binding of antibodies at different concentrations (ng/ml): Chimeric (●) and humanized anti-PD1 variant antibodies from HC (■), HE (▲), HG (▼), HH (♦), HJ (●), HI (□), HK(∆) to HL (⊗) heavy chain variants combined to the LD light chain variant. Detection was performed with a donkey anti-human antibody coupled to peroxidase and revelation was performed by colorimetry at 450nm using TMB substrate. ED50 refers to the concentration required to reach 50% of the signal in this assay. B: Assessment of antibody binding by cytofluorometry on CD3/CD28 stimulated human PBMCs. Serial dilution (µg/ml) of HELC (■), HELD (▼) was added and revealed using a PE labeled mouse anti-human Fc mAb and Canto II cytometer. Data are represented by Mean Fluorescence Intensity (MFI) staining in PD1+ positive CD3+ T cell population. C: Assessment of antibody binding by cytofluorometry on CD3/CD28 stimulated T cells. Serial dilution (µg/ml) of humanized antibodies were added and revealed using a PE labeled mouse anti-human Fc mAb and Canto II cytometer. Data are represented by Mean Fluorescence Intensity (MFI) staining in PD1+ positive CD3+ T cell population.
Figure 1:
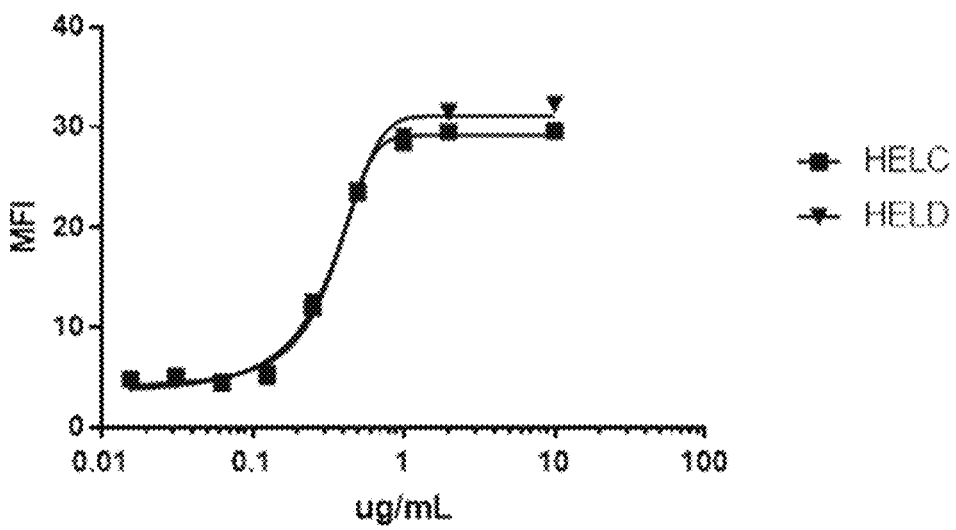
Figure 1:
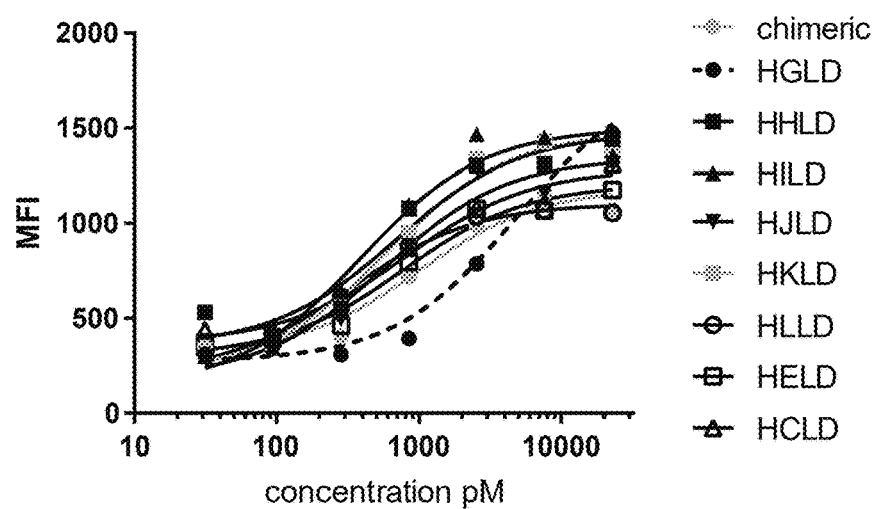

(A): where HC(E97)LB2 ( ) and HC(D97)LB2 (□) are compared to the Chimeric (Δ), at Kabat position R96 (B): where HELD(●) and HE(K96)LD (□) are compared to the Chimeric (Δ).

(C), (D) and (E) : ELISA binding of humanized anti-PD1 variants after mutations on the light variable chain at Kabat position N28 (C) : where HCLw(N28) (□) and the HCLw (Q28) (●) are compared to the Chimeric (Δ),at Kabat position V94 (D): where the Hwt-LA(E34) (□) and HwtLA (N34) (◇) are compared to the Chimeric (Δ) (E): where the HELD(V94) and HELD(L94) are compared to the Chimeric (Δ), at Kabat position E34. For the heavy chain, Kabat position 96 corresponds to sequential position 100 and Kabat position 97 corresponds to sequential position 101. For the light chain, Kabat position 28 corresponds to sequential position 33, Kabat position 34 corresponds to sequential position 39 and Kabat position 94 corresponds to sequential position 99.

Figure 3:
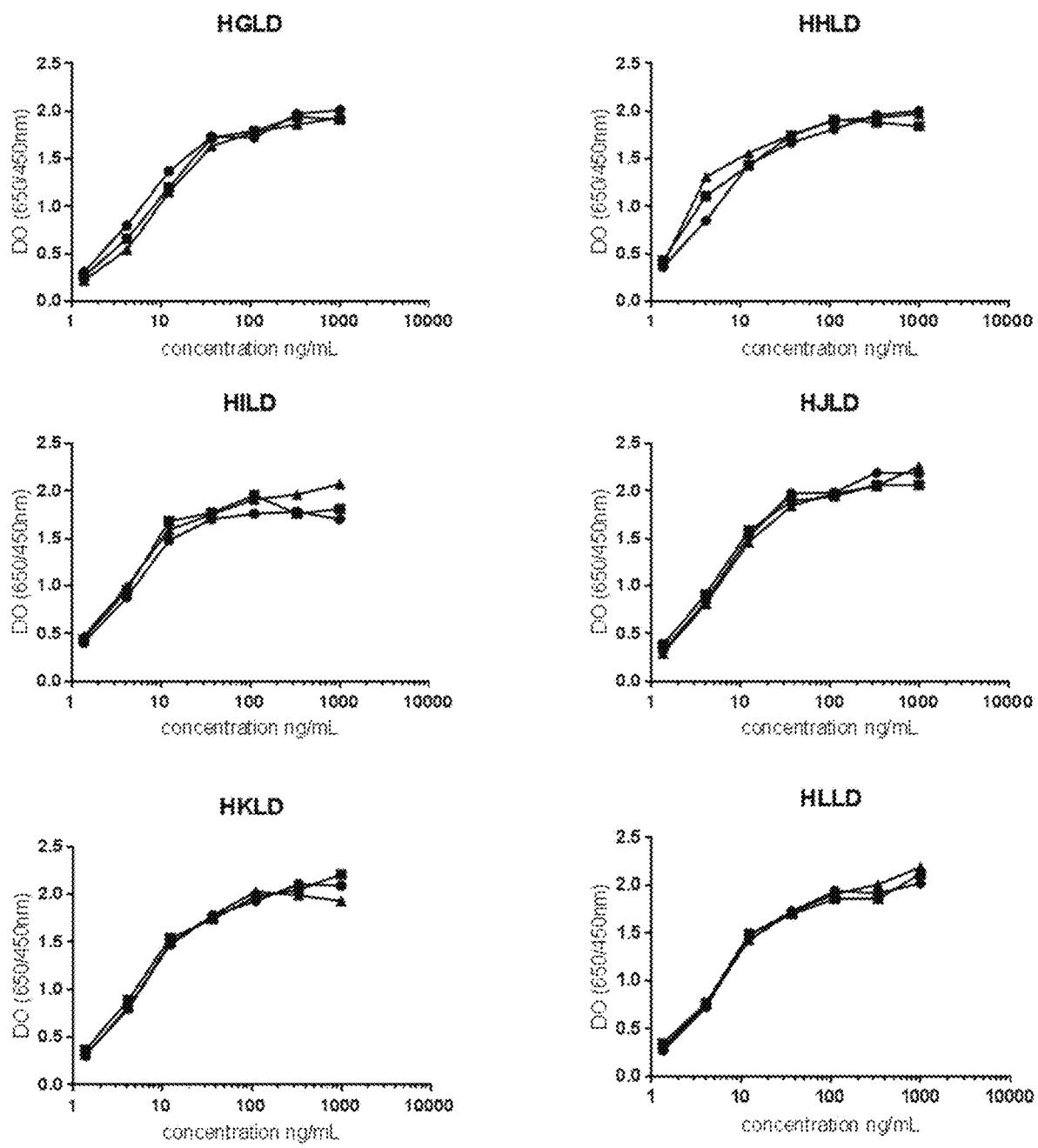

FIG. 3: Stability measurement of the humanized anti-PD1 variant antibodies after 7 days at 4° C. or 37° C. on PD1 binding by ELISA. Days 0 (●), Day 7 at 4° C. (■) and Day 7 at 37° C. (▲).

Figure 4:
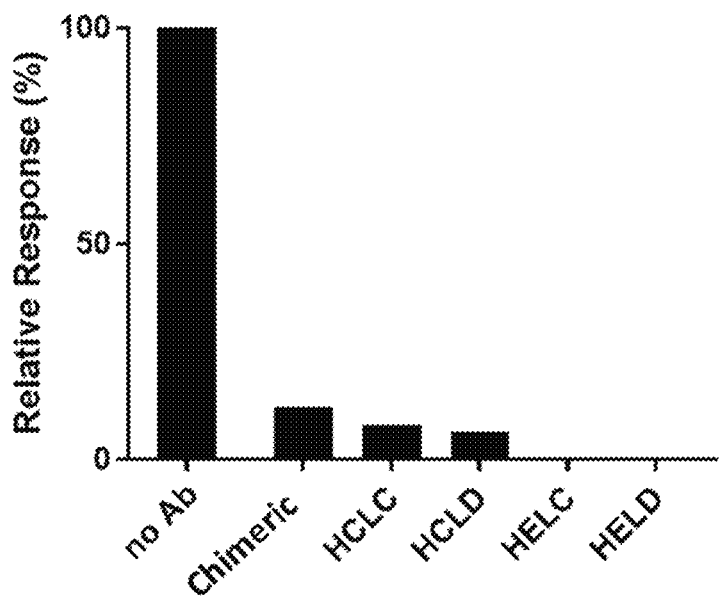
Figure 4:
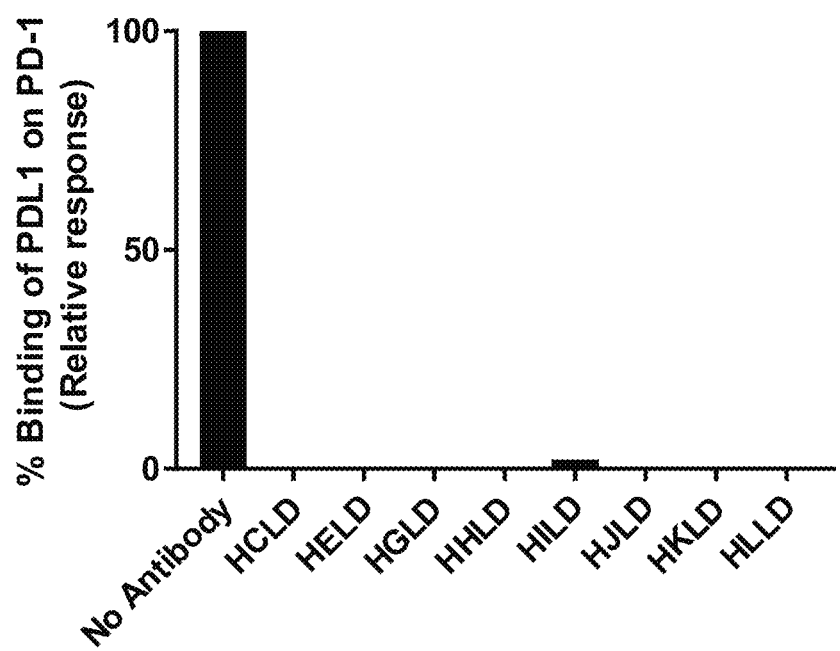
Figure 4:
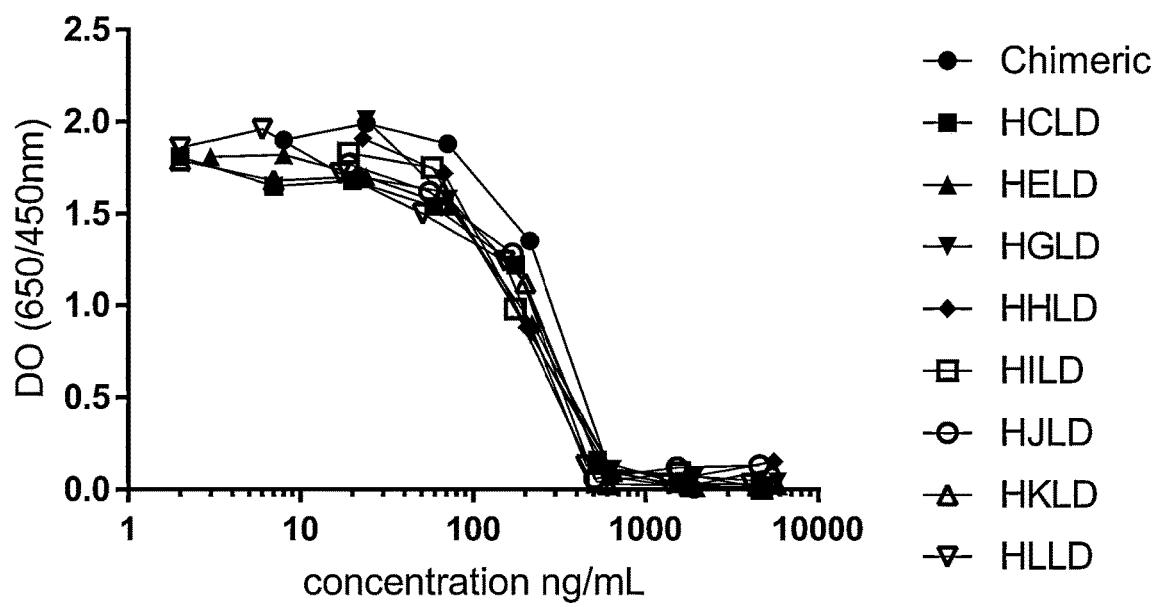

FIG. 4: Antagonist activity of the humanized anti-PD1 variant antibodies on PD1-PDL1 interaction: A: competition between PDL1 and humanized anti-PD1 variant antibodies on the binding to PD1 measured by Biacore.

B: competition between humanized antibodies and PDL1 on PD1 measured by Blitz. Data are represented in percentage of binding response where 100% represents Ka of PD1/PD-L1 interaction without antibody (Relative Response).

C. Binding study of PD1 to PDL1 in presence of an increased concentration of humanized anti-PD1 variant antibodies by ELISA leading to the measurement of the IC50 value of each variant antibodies.

Figure 5A:
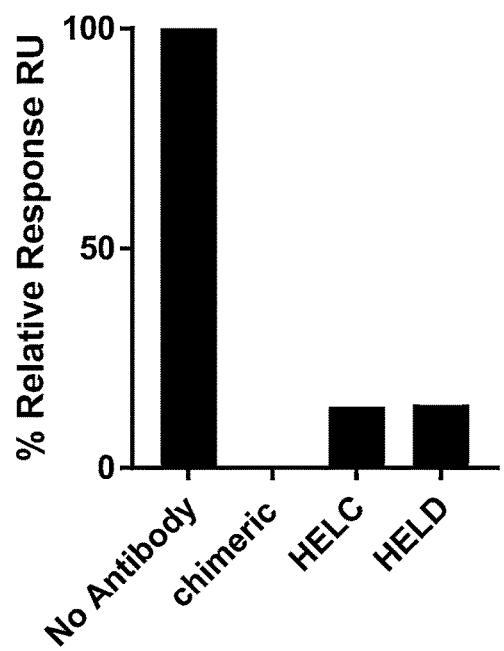
Figure 5B:
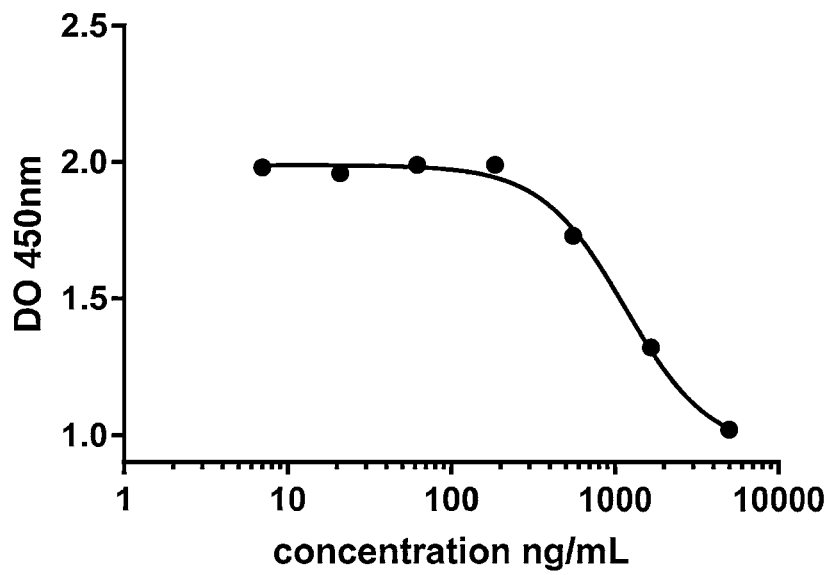

FIGS. 5A-5B: Antagonist activity of the humanized anti-PD1 variant antibodies on PD1-PDL2

A. competition between PDL2 and humanized anti-PD1 variant antibodies on the binding to PD1 measured by Biacore:

B. Binding study of PD1 to PDL2 in presence of an increased concentration of humanized anti-PD1 variant (HKLD) antibodies by ELISA.

Figure 6:
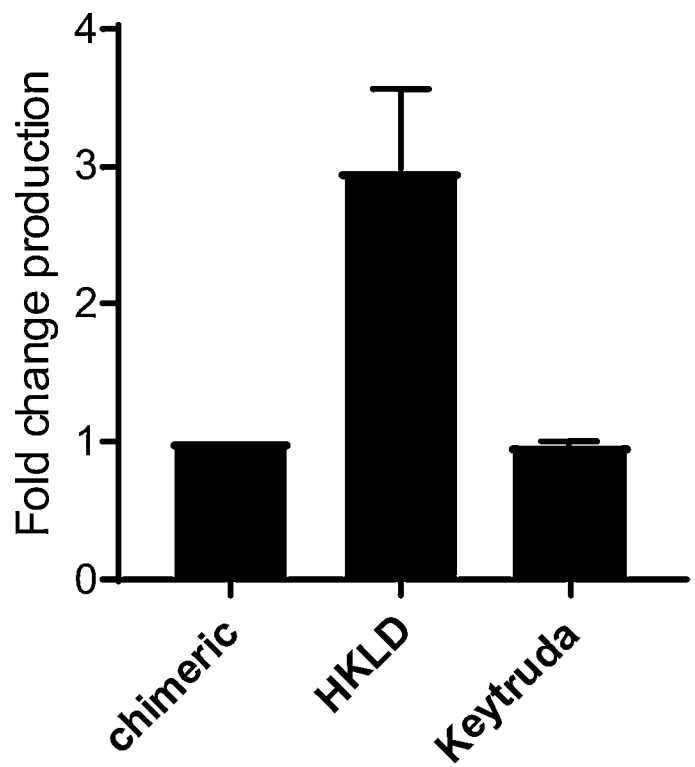

FIG. 6: Higher productivity of the humanized anti-PD1 variant antibodies compared to the chimeric variant and the Keytruda in mammalian cells. Adherent CHO-K1 cells were transiently transfected with DNA encoding Keytruda, HKLD or chimeric anti PD-1 antibody in 12 well-plate. Productivity was dosed by ELISA using (immobilized donkey anti human Fc antibody for detection and revelation with a mouse anti human kappa+a peroxidase conjugated goat anti mouse antibody). Concentration was determined with human IvIgG standard. Data were normalized to the productivity of the chimeric anti PD-1 antibody.

Figure 7:
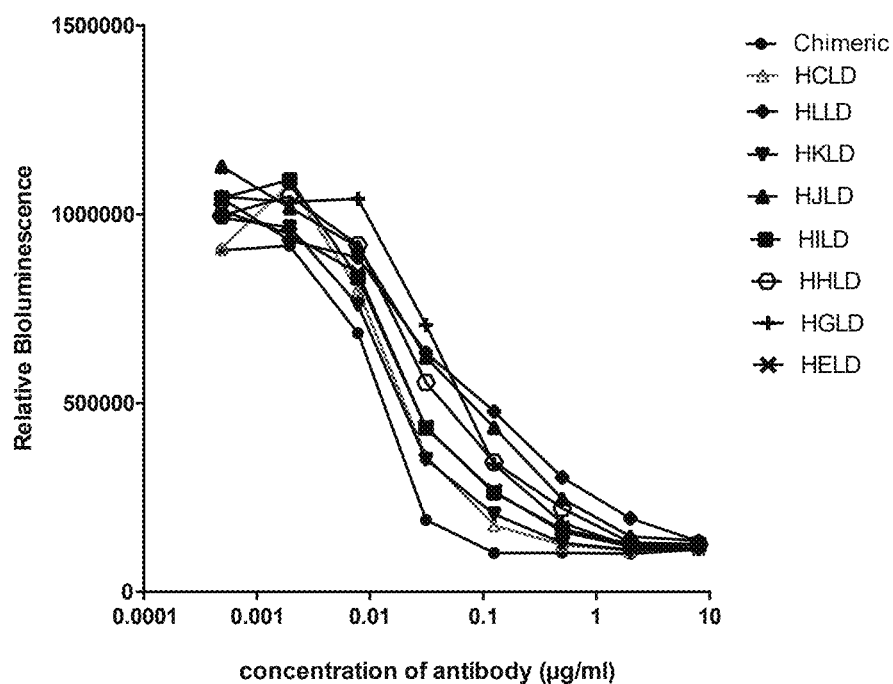
Figure 7:
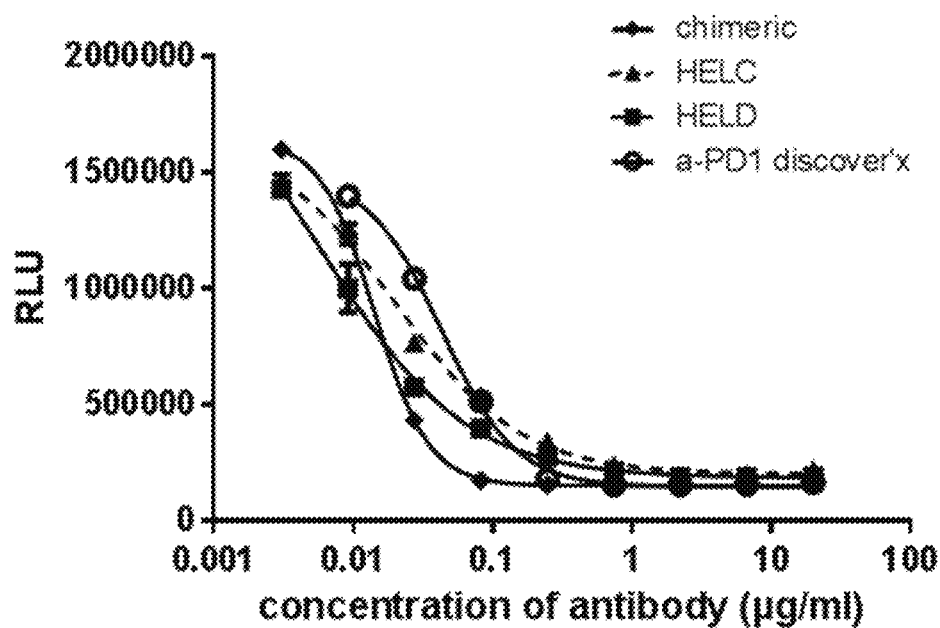

FIG. 7: Bioassay on SHP1-phosphorylation measuring the antagonist activity of the humanized anti-PD1 variant antibodies to block PD1 signaling: PD-1 signaling was tested using a Discoverx bioassay. Chemiluminescence (RLU: (Relative luminescence signal) measured is proportional to PD-1 signaling activation. A: represents results comparing different concentration (µg/ml) of humanized anti-PD1 variant antibodies with the LD variant of the light chain. B: represents results comparing LD and LC variants of the light chain combined with the HE variant of the heavy chain (HELC or HELD antibodies). IC50 (ng/mL) refers to the concentration required to reach 50% of signal inhibition.

Figure 8:
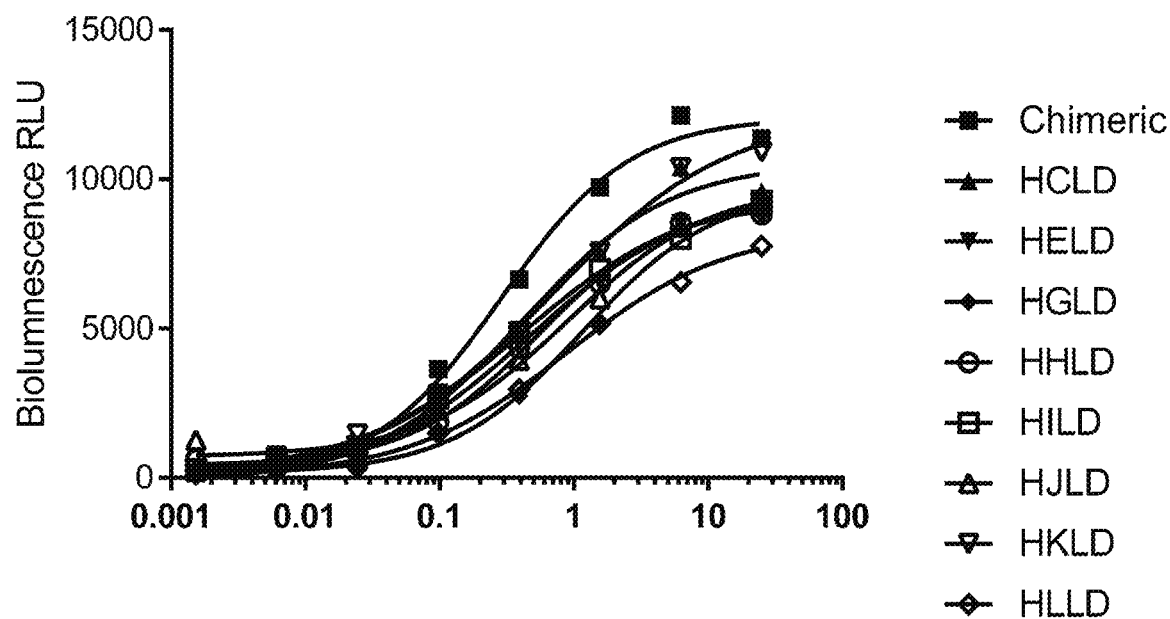

FIG. 8: Bioassay measuring T cell activation in presence of a humanized anti-PD1 variant antibody. A Promega PD-1/PD-L1 bioassay was performed using NFAT luciferase reporter system. Serial dilution of each humanized anti-PD1 variant antibodies were tested. X-axis represents concentration of the antibody in µg/mL. EC50 (µg/mL) refers to the concentration of antibody required to reach 50% of maximum luminescence.

Figure 9:
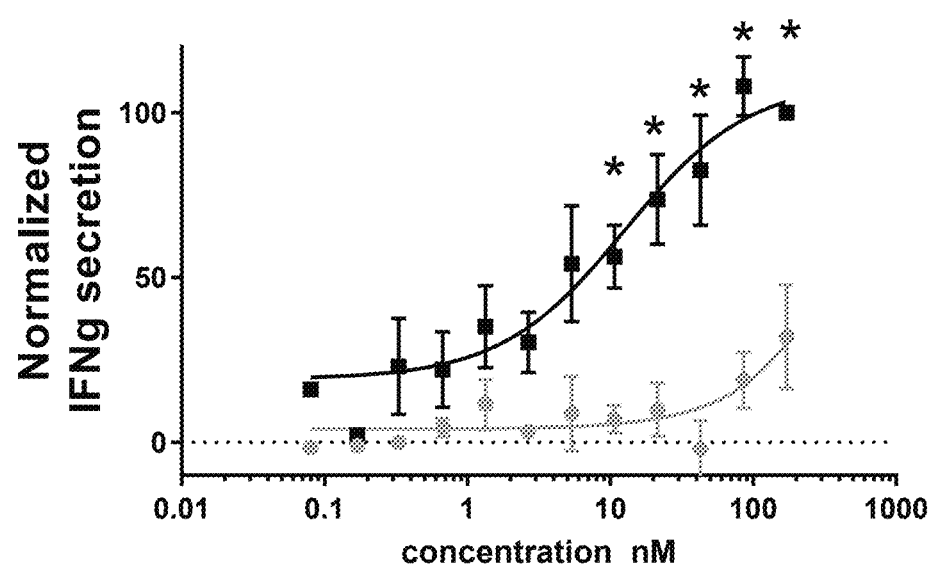

FIG. 9: IFNgamma secretion by T cells following treatment with humanized PD-1 antibody in a Mixed Leucocyte Reaction assay. Monocyte derived dendritic cells were cocultured with allogenic CD4 T cells during 5 days. A. IFNg level in the supernatant quantified by ELISA. Dose curve response of HKLD (black ■) or IgG4 isotype control (grey ●) antibodies were tested. Data represent 4 independent experiments. Statistical significance *p<0,05 was calculated with t-test student.

Figure 10:
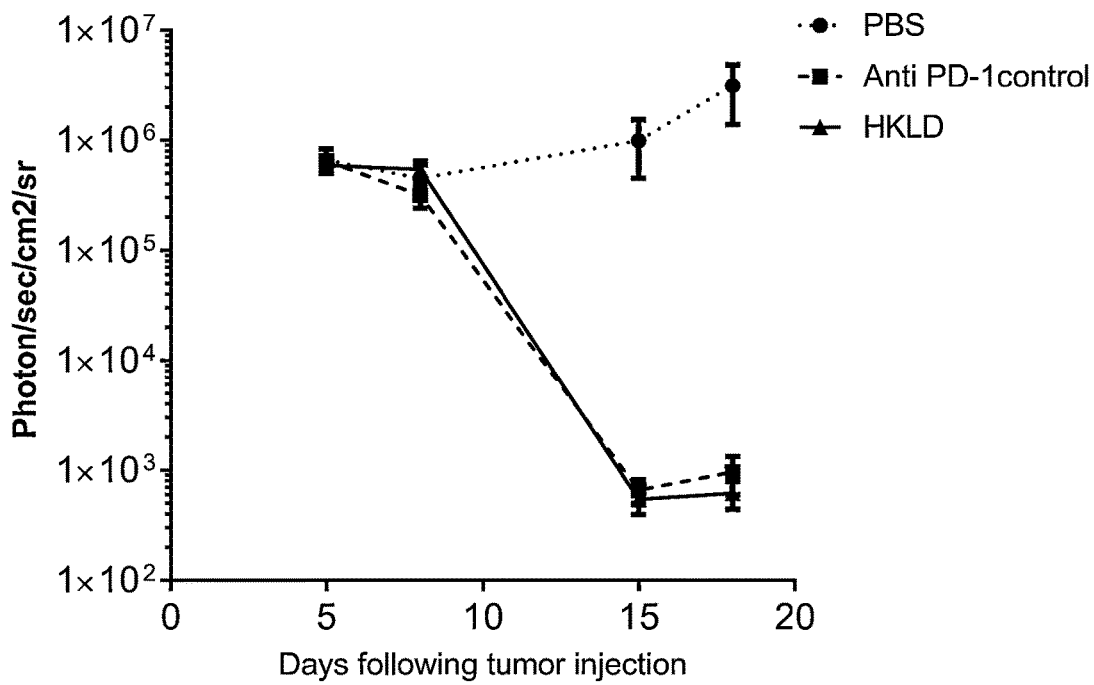
Figure 10:
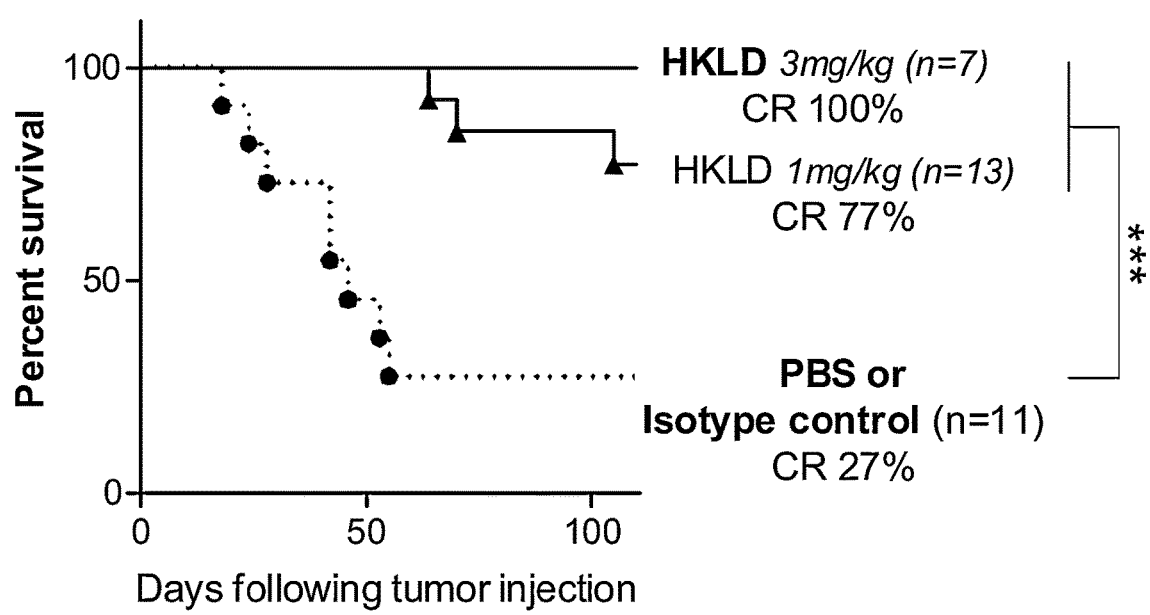

FIG. 10: In vivo efficacy of humanized anti PD-1 variant in a mesothelioma mouse model expressing human form of PD-1. Mice genetically modified to express the extracellular portion of human PD-1 in which exon 2 of PDCD1 gene was replaced with the human counterpart (licensed by Oxford University Innovation). Mesothelioma AK7 cells were injected orthotopically into the pleural cavity and tumor growth was measured by Bioluminescence (photo/s/cm2/sr) (A) and overall survival was assessed (B). Mice were treated with PBS (●) (negative control) or with the anti PD-1 humanized form (HKLD variant) (▲) or an anti PD-1 control (■).

Figure 11:
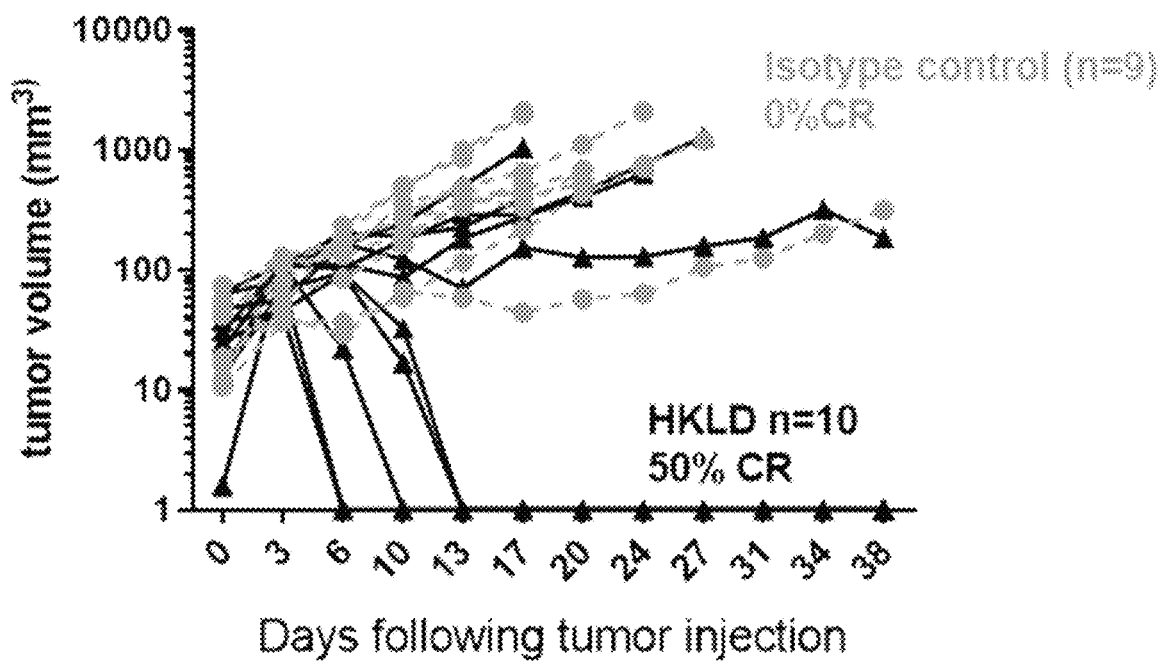
Figure 11:
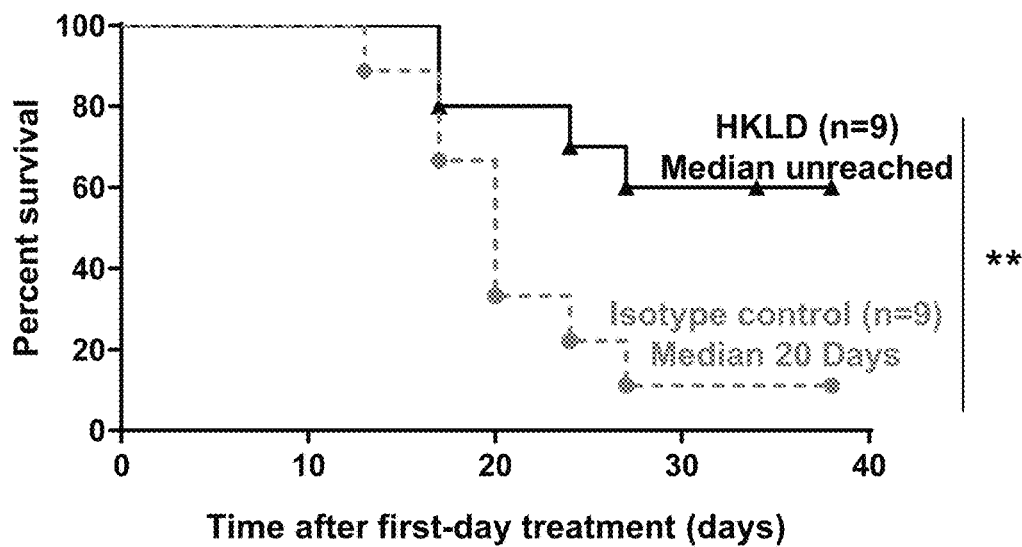
Figure 12:
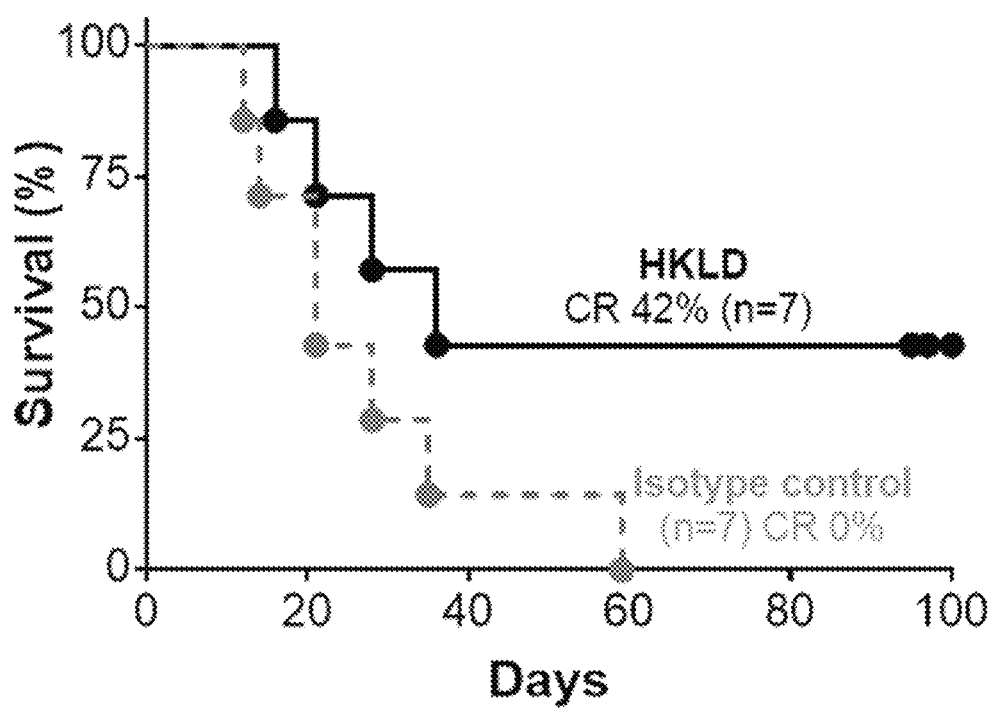

FIG. 11: In vivo efficacy of humanized anti PD-1 variant in ectopic MC38 colon carcinoma mouse model expressing human form of PD-1. MC38 were subcutaneously injected and mice were treated with PBS (grey ●) (negative control) or with the anti PD-1 humanized form (HKLD variant) (black) ▲) and tumor volume (A) and overall survival (B) were assessed. FIG. 12: In vivo efficacy of humanized anti PD-1 variant in hepatocarcinoma mouse model.

Hepa1.6 cells inoculated into the portal vein of the mice form an hepatocarcinoma model. Mice were treated with isotype control IgG4 (grey) (negative control ●) or with the anti PD-1 humanized form (HKLD variant) (black ●) Overall survival was assessed.

Figure 13:
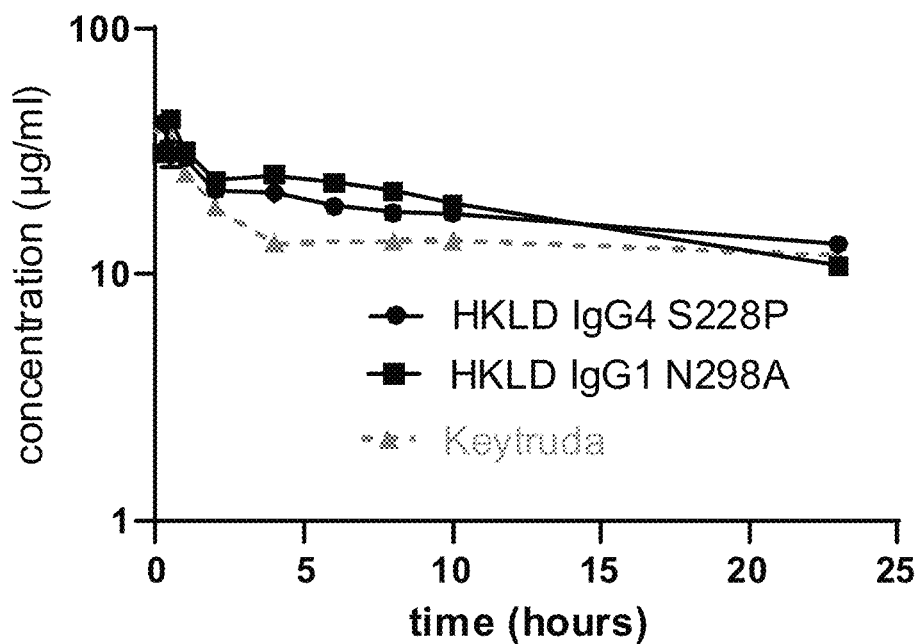
Figure 13:
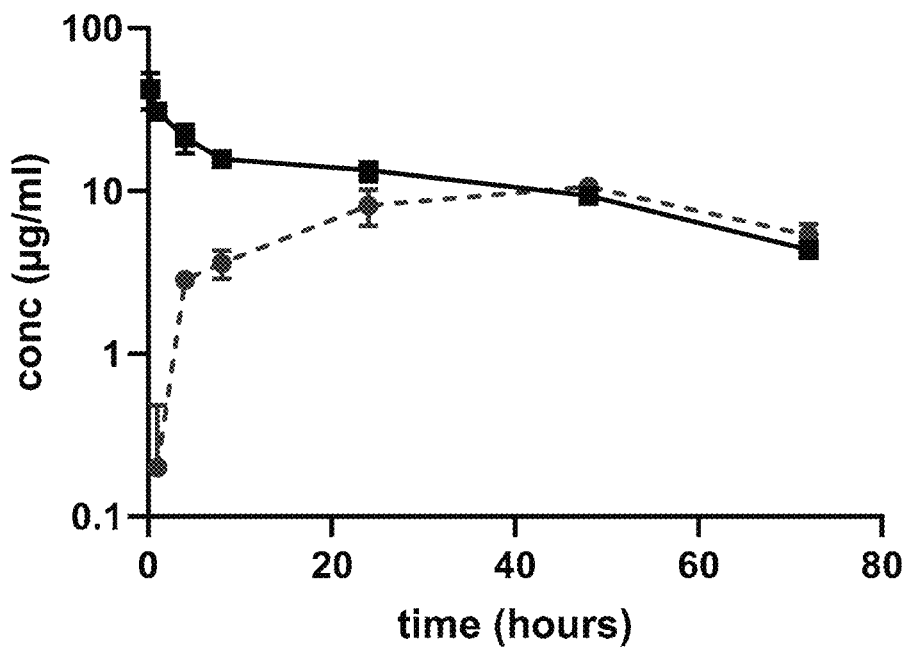
Figure 13:
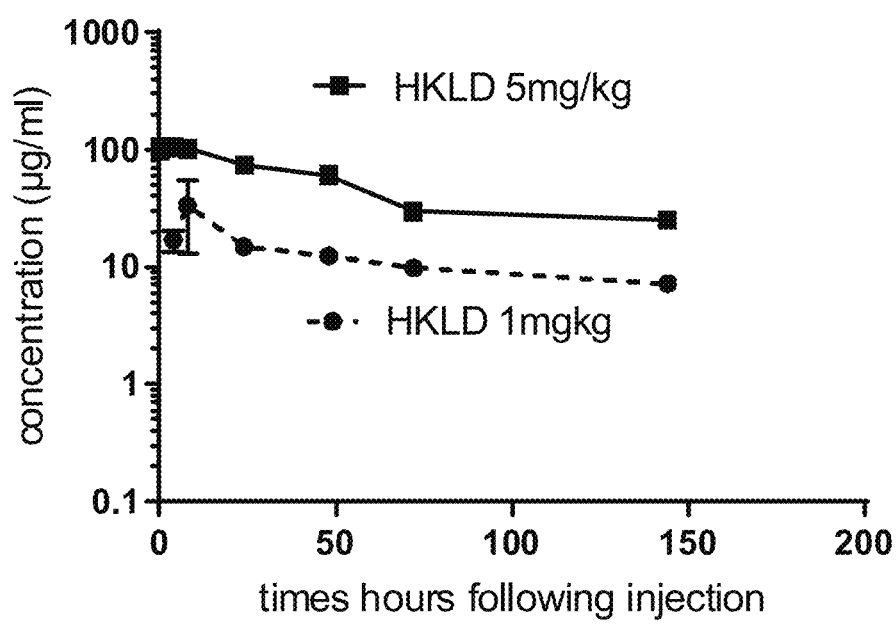

FIG. 13: Pharmacokinetics of humanized PD-1 antibody in cynomolgus monkey and mice following a single injection. A: Balb/C Mice were intravenously with HKLD variant IgG4 S228P isotype (●) or HKLD variant IgG1 N298A isotype (■) or Keytruda (1 dose at 5 mg/kg) (grey ▲). B: Balb/C Mice were intravenously (■) or subcutaneously (●) injected with HKLD variant IgG4 S228P isotype (1 dose 5 mg/kg). C: Cynomolgus monkeys were intravenously injected at 1 mg/kg (●) or 5 mg/kg (■) with HKLD variant. The anti PD-1 antibody was quantified in the sera by homemade ELISA or using MSD technology.

FIGS. 14A-14D: humanized anti PD-1 promotes phagocytosis of PD-L1 negative tumor cells by blocking PD-L1/PD-1 negative interaction on macrophage. A. PD-1/PD-L1 flow cytometry staining of Raji cells, MO, M1 and macrophages used for phagocytosis assay; B. In vitro phagocytosis assay with humanized anti PD-1 antibody. Human M1-macrophages were stained with Cell Proliferation Dye eFluor450 and incubated with CPDeFluor670 labeled Raji cells for 1 hour in the presence of Rituximab (10 ng/mL) and isotype control or humanized anti PD-1 (HKLD, 10 ug/mL). Data represent phagocytosis of 3 independent experiments and are normalized to the maximal phagocytosis. C. same phagocytosis assay was performed with M1 macrophages and Raji cells in the presence of isotype control, humanized anti PD-1, pembrolizumab or nivolumab antibody (10 ug/mL). D. Phagocytosis assay of MO versus M1 macrophages with Raji cells incubated with isotype control, humanized anti PD-1. Data are represented in fold change phagocytosis compared to isotype control.

DETAILED DESCRIPTION OF THE INVENTION

Introduction

Figure 14A:
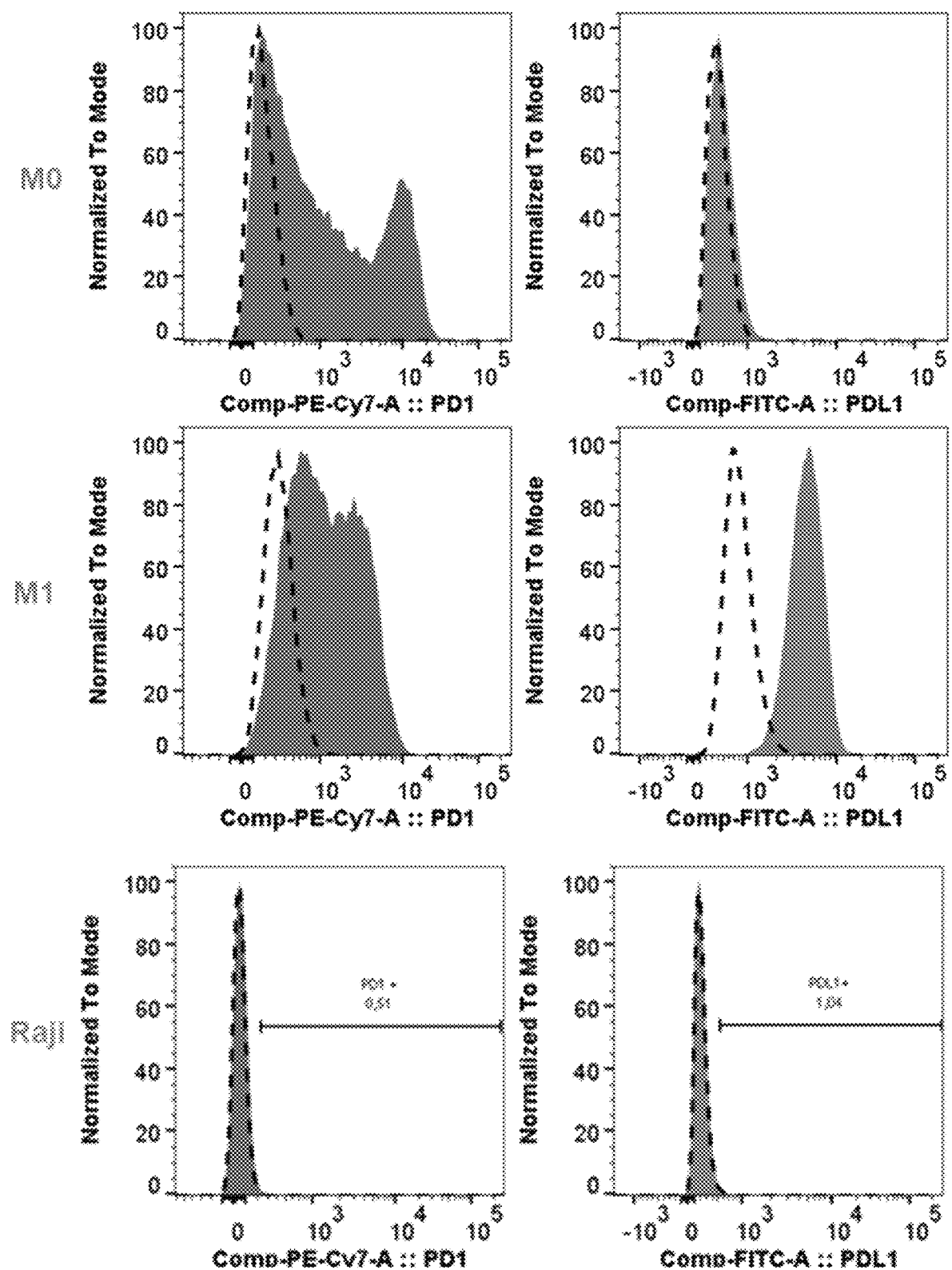
Figure 14B:
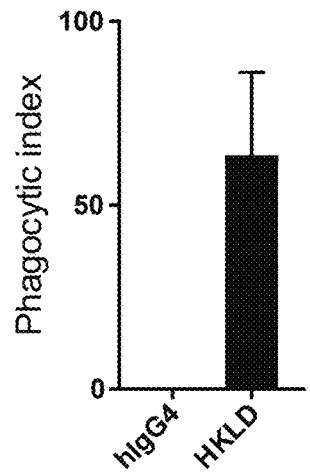
Figure 14B:
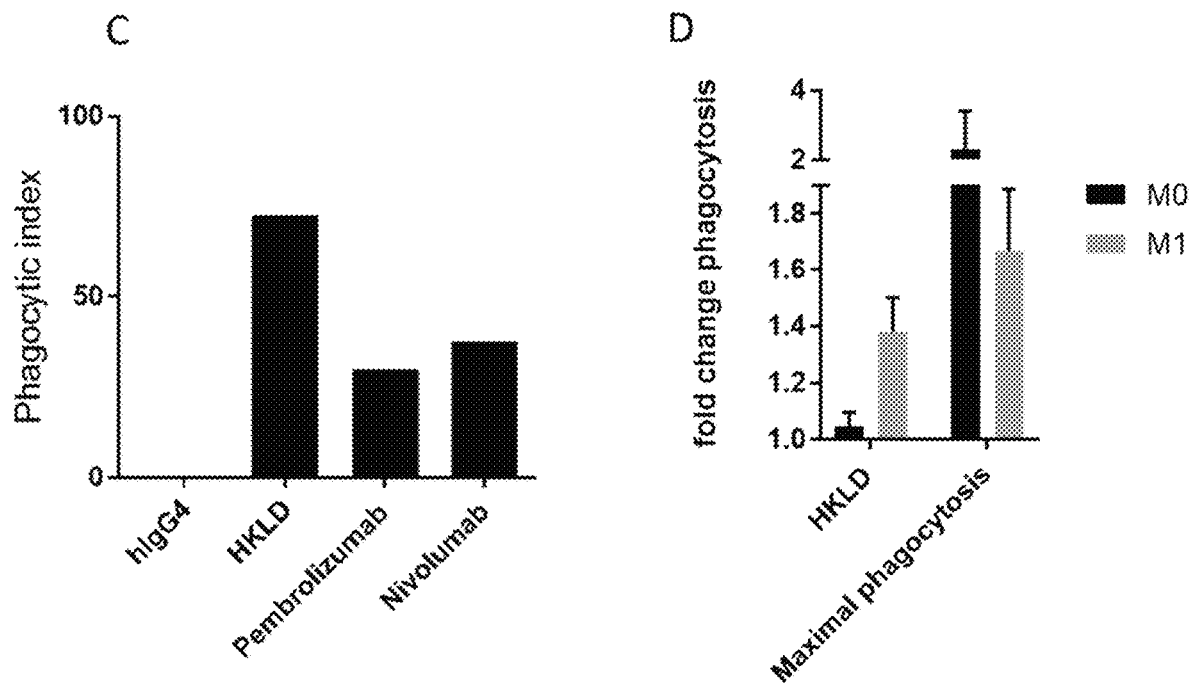

The humanized anti-hPD1 antibody of the invention (HKLD) have all of the following advantages:

- It has a high percentage of humanization, particularly a T20 humanness score of 91.07% for the heavy chain and of 88.7% for the light chain. In comparison, the anti-PD1 antibody called Keytruda, which is a clinically approved antibody and is a standard, has a T20 humanness score of 75.7% for the heavy chain and 82.7% for the light chain (See Table 9). T20 humanness score is a parameter commonly used in the field of antibody humanization first disclosed by Gao et al (BMC Biotechnol, 2013, 13, 55). T20 humanness score is usually used in patent application for defining a humanized antibody (e.g., WO15161311, WO17127664, WO18136626, WO18190719, WO19060750, or WO19170677).
- It surprisingly presents a high manufacturability and high productivity yield when it is produced in mammalian cells (e.g., COS, CHO) compared to a chimeric antibody. Indeed, in CHO cells and in COS cells, it has a production increased by a 3-4 fold factor compared to the chimeric antibody (See Table 11) and an increased production by 2 fold compared to Keytruda (see FIG. 6).
- It presents a binding affinity (KD) for a human PD-1 less than 10-8 M. The humanized antibody of the invention shows an improved binding to PD-1 in comparison to the chimeric antibody as assessed by different methods. The affinity of the humanized antibody HKLD is comparable to the one of the anti-PD1 antibody called Keytruda (see Table 7).
- It has an antagonist activity and inhibits the binding of human PD-L1 and/or PD-L2 to human PD-1 (see, Table 13). More particularly, when compared to the chimeric antibody, the humanized antibody of the invention shows an improved binding to PD1 expressing cells (FIG. 1C) and antagonist capacity (see Tables 14 and 15).
- It is highly stable (see Table 12).
- It blocks PD-1 signaling (SHP-1 phosphorylation and recruitment, cf. Table 15 and FIG. 7) and promotes T cell activation (NFAT mediated activation, cf. Table 16 and FIG. 8).
- It stimulates secretion of effector cytokine by human T cells, more particularly the secretion of IFNg cytokine (FIG. 9).
- Accordingly, it is capable to restore T cell activation.
- It promotes anti-tumor immune response in vivo. Indeed, the humanized antibody of the invention is capable of decreasing the tumor size and to increase the survival in several types of tumors (FIGS. 10-12).
- It has a surprising additional advantage because it is capable of enhancing phagocytosis of tumor cells which are PD-L1 negative by blocking PDL1/PD-1 binding on macrophages (FIG. 14). This effect is specific of the humanized anti-PD-1 antibody of the invention has not been observed with other anti-PD-1 antibodies, especially pembrolizumab and nivolumab (FIG. 14C). Therefore, the humanized anti-PD-1 antibody of the invention induces immune response against tumor cells which do not express PD-L1 through this phagocytosis. This property is of particular interest for immunosuppressed or immunodepressed patients and/or for treating tumors comprising tumor cells which do not express PD-L1. More particularly, it is useful for the treatment of patients who may have a low number of T cells, especially tumor-infiltrated T cells and/or who have a high number of exhausted T cells. Indeed, the antibody can have an additional antitumoral effect through the activation of phagocytosis by macrophages. Without to be bound Without being bound by a theory, the inventors believe that the specific effect of the antibody of the present invention on macrophages could be due to its capacity to bind PD-1 and PD-L1 on the same cell, namely the same macrophage.
- Finally, the humanized antibody of the invention presents a favorable pharmacokinetic (FIG. 13).

Altogether, the humanized anti-PD1 antibody of the invention presents a very high humanization, even in comparison with Keytruda, an anti-PD1 already clinically approved. Compared to the chimeric antibody, it surprisingly presents a better productivity yield, a better binding to PD-1 and a better antagonist capacity. It is stable and has a favorable pharmacokinetic. It enhances T cell activation, activates phagocytosis by macrophages and promotes antitumor immune response in vivo.

Definitions

In order that the present invention may be more readily understood, certain terms are defined hereafter. Additional definitions are set forth throughout the detailed description.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art.

As used herein, the terms "Programmed Death 1", "Programmed Cell Death 1", "PD1", "PD-1", "PDCD1", "PD-1 antigen", "human PD-1", "hPD-1" and "hPD1" are used interchangeably and refer to the Programmed Death-1 receptor, also known as CD279, and include variants and isoforms of human PD-1, and analogs having at least one common epitope with PD-1. PD-1 is a key regulator of the threshold of immune response and peripheral immune tolerance. It is expressed on activated T cells, B cells, monocytes, and dendritic cells and binds to its ligands PD-L1 and PD-L2. Human PD-1 is encoded by the PDCD1 gene. As an example, the amino acid sequence of a human PD-1 is disclosed under GenBank accession number NP_005009. PD1 has four splice variants expressed on human Peripheral blood mononuclear cells (PBMC). Accordingly, PD-1 proteins include full-length PD-1, as well as alternative splice variants of PD-1, such as PD-1Aex2, PD-1Aex3, PD-1Aex2,3 and PD-1Aex2,3,4. Unless specified otherwise, the terms include any variant and, isoform of human PD-1 that are naturally expressed by PBMC, or that are expressed by cells transfected with a PD-1 gene.

As used herein, the term "antibody" describes a type of immunoglobulin molecule and is used in its broadest sense. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass. The heavy-chain constant domains that correspond to the different classes of immunoglobulins are called alpha, delta, epsilon, gamma, and mu, respectively. Unless specifically noted otherwise, the term "antibody" includes intact immunoglobulins and "antibody fragment" or "antigen binding fragment" (such as Fab, Fab', F(ab')2, Fv), single chain (scFv), mutants thereof, molecules comprising an antibody portion, diabodies, linear antibodies, single chain antibodies, and any other modified configuration of the immunoglobulin molecule that comprises an antigen recognition site of the required specificity, including glycosylation variants of antibodies, amino acid sequence variants of antibodies. Preferably, the term "antibody" refers to a humanized antibody.

As used herein, an "antigen-binding fragment" of an antibody means a part of an antibody, i.e. a molecule corresponding to a portion of the structure of the antibody of the invention, that exhibits antigen-binding capacity for PD-1, possibly in its native form; such fragment especially exhibits the same or substantially the same antigen-binding specificity for said antigen compared to the antigen-binding specificity of the corresponding four-chain antibody. Advantageously, the antigen-binding fragments have a similar binding affinity as the corresponding 4-chain antibodies. However, antigen-binding fragment that have a reduced antigen-binding affinity with respect to corresponding 4-chain antibodies are also encompassed within the invention. The antigen-binding capacity can be determined by measuring the affinity between the antibody and the target fragment. These antigen-binding fragments may also be designated as "functional fragments" of antibodies. Antigen-binding fragments of antibodies are fragments which comprise their hypervariable domains designated CDRs (Complementary Determining Regions) or part(s) thereof encompassing the recognition site for the antigen, i.e. the extracellular domain of PD1, thereby defining antigen recognition specificity.

A "Fab" fragment contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. F(ab') fragments are produced by cleavage of the disulfide bond at the hinge cysteines of the F(ab')2 pepsin digestion product. Additional chemical couplings of antibody fragments are known to those of ordinary skill in the art. Fab and F(ab')2 fragments lack the Fc fragment of an intact antibody, clear more rapidly from the circulation of animals, and may have less non-specific tissue binding than an intact antibody (see, e.g., Wahl et al, 1983, J. Nucl. Med. 24:316).

An "Fv" fragment is the minimum fragment of an antibody that contains a complete target recognition and binding site. This region consists of a dimer of one heavy and one light chain variable domain in a tight, non-covalent association (VH-VL dimer). It is in this configuration that the three CDRs of each variable domain interact to define a target binding site on the surface of the VH-VL dimer. Often, the six CDRs confer target binding specificity to the antibody. However, in some instances even a single variable domain (or half of an Fv comprising only three CDRs specific for a target) can have the ability to recognize and bind target, although at a lower affinity than the entire binding site.

"Single-chain Fv" or "scFv" antibody binding fragments comprise the VH and VL domains of an antibody, where these domains are present in a single polypeptide chain. Generally, the Fv polypeptide further comprises a polypeptide linker between the VH and VL domains which enables the scFv to form the desired structure for target binding.

"Single domain antibodies" are composed of a single VH or VL domains which exhibit sufficient affinity to PD-1. In a specific embodiment, the single domain antibody is a camelized antibody {See, e.g., Riechmann, 1999, Journal of Immunological Methods 231:25-38).

In terms of structure, an antibody may have heavy (H) chains and light (L) chains interconnected by disulfide bonds. There are two types of light chain, lambda (λ) and kappa (K). Each heavy and light chain contains a constant region and a variable region (or "domain"). Light and heavy chain variable regions contain a "framework" region interrupted by three hypervariable regions, also called "complementarity-determining regions" or "CDRs". The extent of the framework region and CDRs have been defined (see, Kabat et al., Sequences of Proteins of Immunological Interest, and U.S. Department of Health and Human Services, 1991, which is hereby incorporated by reference). Preferably, the CDRs are defined according to Kabat method. The framework regions act to form a scaffold that provides, for positioning the CDRs in correct orientation by inter-chain, non-covalent interactions. The CDRs are primarily responsible for binding to an epitope of an antigen. The CDRs of each chain are typically referred to as "Complementarity Determining Region 1" or "CDR1", "CDR2", and "CDR3", numbered sequentially starting from the N-terminus. The VL and VH domain of the antibody according to the invention may comprise four framework regions or "FR's", which are referred to in the art and herein as "Framework region 1" or "FR1", "FR2", "FR3", and "FR4", respectively. These framework regions and complementary determining regions are preferably operably linked in the following order: FR1-CDR1-FR2-CDR2-FR3-CDR3-FR4 (from amino terminus to carboxy terminus).

An "antibody heavy chain" as used herein, refers to the larger of the two types of polypeptide chains present in antibody conformations. The CDRs of the antibody heavy chain are typically referred to as "HCDR1", "HCDR2" and "HCDR3". The framework regions of the antibody heavy chain are typically referred to as "HFR1", "HFR2", "HFR3" and "HFR4".

An "antibody light chain," as used herein, refers to the smaller of the two types of polypeptide chains present in antibody conformations, K and λ light chains refer to the two major antibody light chain isotypes. The CDRs of the antibody light chain are typically referred to as "LCDR1", "LCDR2" and "LCDR3". The framework regions of the antibody light chain are typically referred to as "LFR1", "LFR2", "LFR3" and "LFR4".

With regard to the binding of an antibody to a target molecule, the terms "bind" or "binding" refer to peptides, polypeptides, proteins, fusion proteins and antibodies (including antibody fragments) that recognize and contact an antigen. Preferably, it refers to an antigen-antibody type interaction. The terms "specific binding", "specifically binds to," "specific for," "selectively binds" and "selective for" a particular antigen (e.g., PD-1) or an epitope on a particular antigen (e.g., PD-1) mean that the antibody recognizes and binds a specific antigen, but does not substantially recognize or bind other molecules in a sample. For example, an antibody that specifically (or preferentially) binds to PD-1 or to a PD-1 epitope is an antibody that binds this PD-1 epitope for example with greater affinity, avidity, more readily, and/or with greater duration than it binds to other PD-1 epitopes or non-PD-1 epitopes. Preferably, the term "specific binding" means the contact between an antibody and an antigen with a binding affinity equal or lower than $10^{-7}$ M. In certain aspects, antibodies bind with affinities equal or lower than $10^{-8}$ M, $10^{-9}$ M or $10^{-10}$ M.

As used herein "PD-1 antibody," "anti-PD-1 antibody," "PD-1 Ab," "PD-1-specific antibody" or "anti-PD-1 Ab" or "humanized anti-PD-1 antibody" are used interchangeably and refer to an antibody, as described herein, which specifically binds to PD-1, preferably human PD-1. In some embodiments, the antibody binds to the extracellular domain of PD-1. Particularly, an anti-PD-1 antibody is an antibody capable of binding to a PD-1 antigen and inhibits the PD-1-mediated signaling pathway, thereby enhancing immune responses such as T cell activation.

As used herein, the term "humanized antibody" is intended to refer to antibodies in which CDR sequences derived from the germline of another mammalian species, such as a mouse, have been grafted onto human framework sequences (e.g. chimeric antibodies that contain minimal sequence derived from a non-human antibody). A "humanized form" of an antibody, e.g., a non-human antibody, also refers to an antibody that has undergone humanization. A humanized antibody is generally a human immunoglobulin (recipient antibody) in which residues from one or more CDRs are replaced by residues from at least one CDR of a non-human antibody (donor antibody) while maintaining the desired specificity, affinity, and capacity of the original antibody. The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by framework region residues from the donor antibody. Alternatively, selected framework region residues of the donor antibody are replaced by framework region residues from a human or humanized antibody. Additional framework region modifications may be made within the human framework sequences. Humanized antibodies thus may also comprise residues that are not found in either the recipient antibody or the donor antibody. Such amino acid modifications may be made to further refine antibody function and/or increased the humanization process. By "amino acid change" or "amino acid modification" is meant herein a change in the amino acid sequence of a polypeptide. "Amino acid modifications" include substitution, insertion and/or deletion in a polypeptide sequence. By "amino acid substitution" or "substitution" herein is meant the replacement of an amino acid at a particular position in a parent polypeptide sequence with another amino acid. By "amino acid insertion" or "insertion" is meant the addition of an amino acid at a particular position in a parent polypeptide sequence. By "amino acid deletion" or "deletion" is meant the removal of an amino acid at a particular position in a parent polypeptide sequence. The amino acid substitutions may be conservative. A conservative substitution is the replacement of a given amino acid residue by another residue having a side chain ("R-group") with similar chemical properties (e.g., charge, bulk and/or hydrophobicity). As used herein, "amino acid position" or "amino acid position number" are used interchangeably and refer to the position of a particular amino acid in an amino acids sequence, generally specified with the one letter codes for the amino acids. The first amino acid in the amino acids sequence (i.e. starting from the N terminus) should be considered as having position 1.

A conservative substitution is the replacement of a given amino acid residue by another residue having a side chain ("R-group") with similar chemical properties (e.g., charge, bulk and/or hydrophobicity). In general, a conservative amino acid substitution will not substantially change the functional properties of a protein. Conservative substitutions and the corresponding rules are well-described in the state of the art. For instance, conservative substitutions can be defined by substitutions within the groups of amino acids reflected in the following tables:

TABLE A

| Amino Acid Residue | |
|---|---|
| Amino Acid groups | Amino Acid Residues |
| Acidic Residues | ASP and GLU |
| Basic Residues | LYS, ARG, and HIS |
| Hydrophilic Uncharged Residues | SER, THR, ASN, and GLN |
| Aliphatic Uncharged Residues | GLY, ALA, VAL, LEU, and ILE |
| Non-polar Uncharged Residues | CYS, MET, and PRO |
| Aromatic Residues | PHE, TYR, and TRP |

TABLE B

Alternative Conservative Amino Acid Residue Substitution Groups

| | | | |
|---|---|---|---|
| 1 | Alanine (A) | Serine (S) | Threonine (T) |
| 2 | Aspartic acid (D) | Glutamic acid (E) | |
| 3 | Asparagine (N) | Glutamine (Q) | |
| 4 | Arginine (R) | Lysine (K) | |
| 5 | Isoleucine (I) | Leucine (L) | Methionine (M) |
| 6 | Phenylalanine (F) | Tyrosine (Y) | Tryptophan (W) |

TABLE C

Further Alternative Physical and Functional Classifications of Amino Acid Residues

| | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | E, Q, T, K, S, G, P, D, E, and R |

As used herein, an "isolated antibody" is an antibody that has been separated and/or recovered from a component of its natural environment. An isolated antibody includes an antibody in situ within recombinant cells, since at least one component of the antibody's natural environment is not present. In some embodiments, an antibody is purified to homogeneity and/or to greater than 90%, 95% or 99% purity as determined by, for example, electrophoretic (e.g., SDS-PAGE, isoelectric focusing (IEF), capillary electrophoresis) or chromatographic (e.g., ion exchange or reverse phase HPLC) under reducing or non-reducing conditions.

The terms "derive from" and "derived from" as used herein refers to a compound having a structure derived from the structure of a parent compound or protein and whose structure is sufficiently similar to those disclosed herein and based upon that similarity, would be expected by one skilled in the art to exhibit the same or similar properties, activities and utilities as the claimed compounds. For example, a humanized antibody derived from a murine antibody refers to an antibody or antibody fragment that shares similar properties with the murine antibody, e.g. recognizes the same epitope, shares similar VH and VL with modified residues that participate and/or increased the humanization of the antibody.

The term "treatment" refers to any act intended to ameliorate the health status of patients such as therapy, prevention, prophylaxis and retardation of the disease or of the symptoms of the disease. It designates both a curative treatment and/or a prophylactic treatment of a disease. A curative treatment is defined as a treatment resulting in cure or a treatment alleviating, improving and/or eliminating, reducing and/or stabilizing a disease or the symptoms of a disease or the suffering that it causes directly or indirectly. A prophylactic treatment comprises both a treatment resulting in the prevention of a disease and a treatment reducing and/or delaying the progression and/or the incidence of a disease or the risk of its occurrence. In certain embodiments, such a term refers to the improvement or eradication of a disease, a disorder, an infection or symptoms associated with it. In other embodiments, this term refers to minimizing the spread or the worsening of cancers. Treatments according to the present invention do not necessarily imply 100% or complete treatment. Rather, there are varying degrees of treatment of which one of ordinary skill in the art recognizes as having a potential benefit or therapeutic effect. Preferably, the term "treatment" refers to the application or administration of a composition including one or more active agents to a subject who has a disorder/disease, for instance associated with the signaling pathway mediated by PD-1.

As used herein, the terms "disorder" or "disease" refer to the incorrectly functioning organ, part, structure, or system of the body resulting from the effect of genetic or developmental errors, infection, poisons, nutritional deficiency or imbalance, toxicity, or unfavorable environmental factors. Preferably, these terms refer to a health disorder or disease e.g. an illness that disrupts normal physical or mental functions. More preferably, the term disorder refers to immune and/or inflammatory diseases that affect animals and/or humans, such as cancer.

The term "immune disease", as used herein, refers to a condition in a subject characterized by cellular, tissue and/or organ injury caused by an immunologic reaction of the subject to its own cells, tissues and/or organs. The term "inflammatory disease" refers to a condition in a subject characterized by inflammation, e.g., chronic inflammation. Autoimmune disorders may or may not be associated with inflammation. Moreover, inflammation may or may not be caused by an autoimmune disorder.

The term "cancer" as used herein is defined as disease characterized by the rapid and uncontrolled growth of aberrant cells. Cancer cells can spread locally or through the bloodstream and lymphatic system to other parts of the body.

As used herein, the term "disease associated with or related to PD-1", "PD-1 positive cancer" or "PD-1 positive infectious disease" is intended to refer to the cancer or infectious disease (e.g. caused by a virus and/or bacteria) which is resulted from PD-1 expression or has the symptom/characteristic of PD-1 expression , i.e. any condition that is caused by, exacerbated by, or otherwise linked to increased or decreased expression or activities of PD-1.

As used herein, the term "subject", "host", "individual," or "patient" refers to human, including adult and child.

As used herein, a "pharmaceutical composition" refers to a preparation of one or more of the active agents, such as comprising a humanized anti-PD1 antibody according to the invention, with optional other chemical components such as physiologically suitable carriers and excipients. The purpose of a pharmaceutical composition is to facilitate administration of the active agent to an organism. Compositions of the present invention can be in a form suitable for any conventional route of administration or use. In one embodiment, a "composition" typically intends a combination of the active agent, e.g., compound or composition, and a naturally-occurring or non-naturally-occurring carrier, inert (for example, a detectable agent or label) or active, such as an adjuvant, diluent, binder, stabilizer, buffers, salts, lipophilic solvents, preservative, adjuvant or the like and include pharmaceutically acceptable carriers. An "acceptable vehicle" or "acceptable carrier" as referred to herein, is any known compound or combination of compounds that are known to those skilled in the art to be useful in formulating pharmaceutical compositions.

"An effective amount" or a "therapeutic effective amount" as used herein refers to the amount of active agent required to confer therapeutic effect on the subject, either alone or in combination with one or more other active agents, e.g. the amount of active agent that is needed to treat the targeted disease or disorder, or to produce the desired effect. The "effective amount" will vary depending on the agent(s), the disease and its severity, the characteristics of the subject to be treated including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

As used herein, the term "medicament" refers to any substance or composition with curative or preventive properties against disorders or diseases.

The term "in combination" as used herein refers to the use of more than one therapy (e.g., prophylactic and/or therapeutic agents). The use of the term "in combination" does not restrict the order in which therapies (e.g., prophylactic and/or therapeutic agents) are administered to a subject with a disease or disorder.

The terms "polynucleotide", "nucleic acid" and "nucleic acid sequence" are equivalent and refer to a polymeric form of nucleotide of any length, for example RNA or DNA or analogs thereof. Nucleic acids (e.g., components, or portions, of the nucleic acids) of the present invention may be naturally occurring, modified or engineered. Engineered nucleic acids include recombinant nucleic acids and synthetic nucleic acids. "Isolated nucleic acid encoding an anti-PD1 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell. As used herein, the terms "nucleic acid construct", "plasmid", and "vector" are equivalent and refer to a nucleic acid molecule that serves to transfer a passenger nucleic acid sequence, such as DNA or RNA, into a host cell.

As used herein, the term "host cell" is intended to include any individual cell or cell culture that can be or has been recipient of vectors, exogenous nucleic acid molecules, and polynucleotides encoding the antibody construct of the present invention; and/or recipients of the antibody construct itself. The introduction of the respective material into the cell can be carried out by way of transformation, transfection and the like. The term "host cell" is also intended to include progeny or potential progeny of a single cell. Host cells include bacterial, microbial, plant and animal cells.

"Immune cells" as used herein refers to cells involved in innate and adaptive immunity for example such as white blood cells (leukocytes) which are derived from hematopoietic stem cells (HSC) produced in the bone marrow, lymphocytes (T cells, B cells, natural killer (NK) cells and Natural Killer T cells (NKT)) and myeloid-derived cells (neutrophil, eosinophil, basophil, monocyte, macrophage, dendritic cells). In particular, the immune cell can be selected in the non-exhaustive list comprising B cells, T cells, in particular $CD4^+$ T cells and $CD8^+$ T cells, NK cells, NKT cells, APC cells, dendritic cells and monocytes. "T cell" as used herein includes for example CD4+ T cells, CD8+ T cells, T helper 1 type T cells, T helper 2 type T cells, T helper 17 type T cells and inhibitory T cells.

The term "immune response" refers to the action of, for example, lymphocytes, antigen presenting cells, phagocytic cells, granulocytes, and soluble macromolecules produced by the above cells or the liver (including antibodies, cytokines, and complements) that results in selective damage to, destruction of, or elimination from the human body of invading pathogens, cells or tissues infected with pathogens, cancerous cells, or, in cases of autoimmunity or pathological inflammation, normal human cells or tissues.

The term "antagonist" as used herein, refers to a substance that-block blocks or reduces the activity or functionality of another substance. Particularly, this term refers to an antibody that binds to a cellular receptor (e.g. PD-1) as a reference substance (e.g. PD-L1 and/or PD-L2), preventing it from producing all or part of its usual biological effects (e.g. the creation of an immune suppressive microenvironment). The antagonist activity of a humanized antibody according to the invention may be assessed by competitive ELISA.

As used herein, the term "isolated" indicates that the recited material (e.g., antibody, polypeptide, nucleic acid, etc.) is substantially separated from, or enriched relative to, other materials with which it occurs in nature. Particularly, an "isolated" antibody is one which has been identified and separated and/or recovered from a component of its natural environment. For example, the isolated antibody is purified (1) to greater than 75% by weight of antibody as determined by the Lowry method, or (2) to homogeneity by SDS-PAGE under reducing or non-reducing conditions. Isolated antibody includes the antibody in situ within recombinant cells since at least one component of the antibody's natural environment will not be present. Ordinarily, however, isolated antibody will be prepared by at least one purification step.

The term "and/or" as used herein is to be taken as specific disclosure of each of the two specified features or components with or without the other. For example, "A and/or B" is to be taken as specific disclosure of each of (i) A, (ii) B and (iii) A and B, just as if each is set out individually.

The term "a" or "an" can refer to one of or a plurality of the elements it modifies (e.g., "a reagent" can mean one or more reagents) unless it is contextually clear either one of the elements or more than one of the elements is described.

The term "about" as used herein in connection with any and all values (including lower and upper ends of numerical ranges) means any value having an acceptable range of deviation of up to +/−10% (e.g., +/−0.5%, +/−1%, +/−1.5%, +/−2%, +/−2.5%, +/−3%, +/−3.5%, +/−4%, +/−4.5%, +/−5%, +/−5.5%, +/−6%, +/−6.5%, +/−7%, +/−7.5%, +/−8%, +/−8.5%, +/−9%, +1-9.5%). The use of the term "about" at the beginning of a string of values modifies each of the values (i.e. "about 1, 2 and 3" refers to about 1, about 2 and about 3). Further, when a listing of values is described herein (e.g. about 50%, 60%, 70%, 80%, 85% or 86%) the listing includes all intermediate and fractional values thereof (e.g., 54%, 85.4%).

Humanized Antibody Against Human PD-1

Provided herein is a humanized antibody that binds to human PD-1. In some aspects, the humanized antibody specifically binds to human PD-1, preferably to the extracellular domain of human PD-1. In some aspects, the humanized antibody selectively binds to one or more of full-length human PD-1, PD-1Aex2, PD-1Aex3, PD-1Aex2,3 and PD-1Aex2,3,4.

In some aspects, the humanized anti-PD1 antibody is an isolated antibody, particularly a non-natural isolated antibody. Such isolated humanized anti-PD1 antibody can be prepared by at least one purification step. In some embodiments, an isolated antibody is purified to at least 80%, 85%, 90%, 95% or 99% by weight. In some embodiments, an isolated antibody is provided as a solution comprising at least 85%, 90%, 95%, 98%, 99% to 100% by weight of an antibody, the remainder of the weight comprising the weight of other solutes dissolved in the solvent.

Humanized forms of the anti-PD1 antibody according to this invention may comprise immunoglobulin of any class, such as IgD, IgE, IgG, IgA, or IgM (or sub-class thereof), immunoglobulin chains or fragments thereof (such as Fv, Fab, Fab', F(ab')2, scFv or other antigen-binding subsequences of antibodies) which contain minimal sequence derived from a non-human (e.g. murine) immunoglobulin targeting human PD-1. Preferably, the humanized anti-hPD-1 antibody according to the invention derives from an IgG1, IgG2, IgG3 or IgG4, preferably from IgG4.

Preferably, the humanized antibody against human PD-1 is a monoclonal antibody.

Preferably, such antibody has the ability to block or inhibit the interaction between PD-1 and at least one of its ligand (e.g. PD-L1 and/or PD-L2). The ability to "block binding" or "block interaction" or "inhibit interaction" as used herein refers to the ability of an antibody or antigen-binding fragment to prevent the binding interaction between two molecules (e.g. PD-1 and its ligand PD-L1 and/or PD-L2) to any detectable degree.

Preferably, the antibody or antigen binding fragment thereof is an antagonist of the binding of human PD-L1 and/or PD-L2 to human PD-1, more preferably of human PD-L1 and PD-L2 to human PD-1.

In certain embodiments, the anti-hPD1 antibody or antigen-binding fragment inhibits the binding interaction between PD-1 and at least one of its ligands (e.g. PD-L1 and/or PD-L2, preferably PD-L1 and PD-L2) by at least 50%. In certain embodiments, this inhibition may be greater than 60%, greater than 70%, greater than 80%, or greater than 90%.

"Complementarity determining regions" or "CDRs" are known in the art as referring to non-contiguous sequences of amino acids within antibody variable regions, which confer antigen specificity and binding affinity. The precise amino acid sequence boundaries of a given CDR can be readily determined using any of a number of well-known schemes, including those described by Kabat et al., (Sequences of Proteins of Immunological Interest 5th ed. (1991) "Kabat" numbering scheme); Al-Lazikani et al., 1997, J. Mol. Biol, 273:927-948 ("Chothia" numbering scheme); MacCallum et al, 1996, J. Mol. Biol. 262:732-745 ("Contact" numbering scheme); Lefranc et al., Dev. Comp. Immunol., 2003, 27:55-77 ("IMGT" numbering scheme); and Honegge and Pluckthun, J. Mol. Biol, 2001, 309:657-70 ("AHo" numbering scheme). Unless otherwise specified, the numbering scheme used for identification of a particular CDR herein is the Kabat numbering scheme.

The CDRs regions of the humanized antibody are derived from a murine antibody and have been optimized to i) provide a safe humanized antibody with a very high level of humanization; and ii) increase the antibody properties, more particularly a higher production yield.

In one embodiment, the humanized anti-human-PD-1 antibody or antigen binding fragment thereof comprises:
(i) a heavy chain variable domain comprising HCDR1 comprising or consisting of an amino acid sequence of SEQ ID NO: 1, HCDR2 comprising or consisting of an amino acid sequence of SEQ ID NO: 2 and HCDR3 comprising or consisting of an amino acid sequence of SEQ ID NO: 9, and
(ii) a light chain variable domain comprising LCDR1 comprising or consisting of an amino acid sequence of SEQ ID NO: 12, LCDR2 comprising or consisting of an amino acid sequence of SEQ ID NO: 13 and LCDR3 comprising or consisting of an amino acid sequence of SEQ ID NO: 14.

In one embodiment, the anti-PD1 antibody or antigen binding fragment according to the invention comprises framework regions, in particular heavy chain variable region framework regions (HFR) HFR1, HFR2, HFR3 and HFR4 and light chain variable region framework regions (LFR) LFR1, LFR2, LFR3 and LFR4.

Preferably, the anti-PD1 antibody or antigen binding fragment according to the invention comprises human or humanized framework regions. A "human acceptor framework" for the purposes herein is a framework comprising the amino acid sequence of a light chain variable domain (VL) framework or a heavy chain variable domain (VH) framework derived from a human immunoglobulin framework or a human consensus framework, as defined below. A human acceptor framework derived from a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence. A "human consensus framework" is a framework which represents the most commonly occurring amino acid residues in a selection of human immunoglobulin VL or VH framework sequences.

Particularly, the anti-PD1 antibody or antigen binding fragment comprises heavy chain variable region framework regions (HFR) HFR1, HFR2, HFR3 and HFR4 comprising an amino acid sequence of SEQ ID NOs: 37, 38, 39 and 40, respectively, optionally with one, two or three modification (s) selected from substitution(s), addition(s), deletion(s) and any combination thereof at any position but positions 27, 29 and 32 of HFR3, i.e., of SEQ ID NO: 40. Preferably, the anti-PD1 antibody or antigen binding fragment comprises HFR1 of SEQ ID NO: 37, HFR2 of SEQ ID NO: 38, HFR3 of SEQ ID NO: 39 and HFR4 of SEQ ID NO: 40.

Alternatively or additionally, the anti-PD1 antibody or antigen binding fragment comprises light chain variable region framework regions (LFR) LFR1, LFR2, LFR3 and LFR4 comprising an amino acid sequence of SEQ ID NOs: 41, 42, 43 and 44, respectively, optionally with one, two or three modification(s) selected from substitution(s), addition(s), deletion(s) and any combination thereof. Preferably, the humanized anti-PD1 antibody or antigen binding fragment comprises LFR1 of SEQ ID NO: 41, LFR2 of SEQ ID NO: 42, LFR3 of SEQ ID NO: 43 and LFR4 of SEQ ID NO: 44.

The VL and VH domain of the antibody according to the invention may comprise four framework regions interrupted by three complementary determining regions preferably operably linked in the following order: FR1-CDR1-FR2-CDR2-FR3-CDR3-FR4 (from amino terminus to carboxy terminus).

In a first embodiment, the anti-human-PD-1 humanized antibody or antigen binding fragment thereof comprises:
(a) a heavy chain variable region (VH) comprising or consisting of an amino acid sequence of SEQ ID NO: 21, optionally with one, two or three modification(s) selected from substitution(s), addition(s), deletion(s) and any combination thereof at any position but positions 7, 16, 17, 20, 33, 38, 43, 46, 62, 63, 65, 69, 73, 76, 78, 80, 84, 85, 88, 93, 95, 96, 97, 98, 100, 101, 105, 106 and 112 of SEQ ID NO: 21;
(b) a light chain variable region (VL) comprising or consisting of an amino acid sequence of SEQ ID NO: 24, optionally with one, two or three modification(s) selected from substitution(s), addition(s), deletion(s) and any combination thereof at any position but positions 3, 4, 7, 14, 17, 18, 28, 29, 33, 34, 39, 42, 44, 50, 81, 88, 94, 97, 99 and 105 of SEQ ID NO: 24.

Preferably, the modifications are substitutions, in particular conservative substitutions.

Preferably, the anti-human-PD-1 humanized antibody or antigen binding fragment thereof comprises: (a) a heavy chain variable region (VH) comprising or consisting of an amino acid sequence of SEQ ID NO: 21; and (b) a light chain variable region (VL) comprising or consisting of an amino acid sequence of SEQ ID NO: 24.

In one embodiment, the heavy chain (CH) and the light chain (CL) comprises the VL and VH sequences as described hereabove.

In a particular embodiment, the anti-human-PD-1 antibody or antigen binding fragment thereof comprises: (a) a heavy chain comprising or consisting of an amino acid sequence of SEQ ID NO: 31, optionally with one, two or three modification(s) selected from substitution(s), addition(s), deletion(s) and any combination thereof at any position but positions 7, 16, 17, 20, 33, 38, 43, 46, 62, 63, 65, 69, 73, 76, 78, 80, 84, 85, 88, 93, 95, 96, 97, 98, 100, 101, 105, 106 and 112 of SEQ ID NO: 31, and (b) a light chain comprising or consisting of an amino acid sequence of SEQ ID NO: 34, optionally with one, two or three modification(s) selected from substitution(s), addition(s), deletion(s) and any combination thereof at any position but positions 3, 4, 7, 14, 17, 18, 28, 29, 33, 34, 39, 42, 44, 50, 81, 88, 94, 97, 99 and 105 of SEQ ID NO: 34.

Preferably, the modifications are substitutions, in particular conservative substitutions.

Preferably, the anti-human-PD-1 antibody or antigen binding fragment thereof comprises: (a) a heavy chain comprising or consisting of an amino acid sequence of SEQ ID NO: 31, and (b) a light chain comprising or consisting of an amino acid sequence of SEQ ID NO: 34.

Fc and Hinge Region

Several researches to develop therapeutic antibodies had led to engineer the Fc regions to optimize antibody properties allowing the generation of molecules that are better suited to the pharmacology activity required of them. The Fc region of an antibody mediates its serum half-life and effector functions, such as complement-dependent cytotoxicity (CDC), antibody-dependent cellular cytotoxicity (ADCC) and antibody-dependent cell phagocytosis (ADCP). Several mutations located at the interface between the CH2 and CH3 domains, such as T250Q/M428L and M252Y/S254T/T256E+H433K/N434F, have been shown to increase the binding affinity to FcRn and the half-life of IgG1 in vivo. However, there is not always a direct relationship between increased FcRn binding and improved half-life. One approach to improve the efficacy of a therapeutic antibody is to increase its serum persistence, thereby allowing higher circulating levels, less frequent administration and reduced doses. Engineering Fc regions may be desired to either reduce or increase the effector function of the antibody. For antibodies that target cell-surface molecules, especially those on immune cells, abrogating effector functions is required. Conversely, for antibodies intended for oncology use, increasing effector functions may improve the therapeutic activity. The four human IgG isotypes bind the activating Fcγ receptors (FcγRI, FcγRIIa, FcγRIIIa), the inhibitory FcγRIIb receptor, and the first component of complement (C1q) with different affinities, yielding very different effector functions. Binding of IgG to the FcγRs or C1q depends on residues located in the hinge region and the CH2 domain. Two regions of the CH2 domain are critical for FcγRs and C1q binding, and have unique sequences in IgG2 and IgG4.

The humanized antibody according to the invention optionally comprises at least a portion of an immunoglobulin constant region (Fc), typically that of a human or humanized immunoglobulin. Preferably, the Fc region is a part of the humanized anti-hPD-1 antibody described herein. As well known by one skilled in the art, the choice of IgG isotypes of the heavy chain constant domain centers on whether specific functions are required and the need for a suitable in vivo half-life. For example, antibodies designed for selective eradication of cancer cells typically require an active isotype that permits complement activation and effector-mediated cell killing by antibody-dependent cell-mediated cytotoxicity. Both human IgG1 and IgG3 (shorter half-life) isotypes meet these criteria, particularly human IgG1 isotype (wild type and variants). In particular, depending on the IgG isotype of the heavy chain constant domain (particularly human wild type and variants IgG1 isotype), the humanized anti-hPD1 antibody of the invention can be cytotoxic towards cells expressing PD-1 via a CDC, ADCC and/or ADCP mechanism. In fact, the fragment crystallisable (Fc) region interacts with a variety of accessory molecules to mediate indirect effector functions such as antibody-dependent cellular cytotoxicity (ADCC), antibody-dependent cellular phagocytosis (ADCP) and complement-dependent cytotoxicity (CDC).

In preferred embodiments, the constant region is derived from a human immunoglobulin heavy chain, for example, IgG1, IgG2, IgG3, IgG4, or other classes. In a further aspect, the human constant region is selected from the group consisting of IgG1, IgG2, IgG2, IgG3 and IgG4. Preferably, the humanized anti-PD1 antibody comprises an IgG1 or an IgG4 Fc-region. Even more preferably, the humanized anti-hPD1 antibody comprises an IgG4 Fc-region with a S228P that stabilizes the IgG4.

In one embodiment, the anti-PD1 antibody comprises a truncated Fc region or a fragment of the Fc region. In one embodiment, the constant region includes a CH2 domain. In another embodiment, the constant region includes CH2 and CH3 domains or includes hinge-CH2-CH3. Alternatively, the constant region can include all or a portion of the hinge region, the CH2 domain and/or the CH3 domain. In a preferred embodiment, the constant region contains a CH2 and/or a CH3 domain derived from a human IgG4 heavy chain.

In another embodiment, the constant region includes a CH2 domain and at least a portion of a hinge region. The hinge region can be derived from an immunoglobulin heavy chain, e.g., IgG1, IgG2, IgG3, IgG4, or other classes. Preferably, the hinge region is derived from human IgG1, IgG2, IgG3, IgG4, or other suitable classes, mutated or not. More preferably the hinge region is derived from a human IgG1 heavy chain. In one embodiment, the constant region includes a CH2 domain derived from a first antibody isotype and a hinge region derived from a second antibody isotype. In a specific embodiment, the CH2 domain is derived from a human IgG2 or IgG4 heavy chain, while the hinge region is derived from an altered human IgG1 heavy chain.

In one embodiment, the constant region contains a mutation that reduces affinity for an Fc receptor or reduces Fc effector function. For example, the constant region can contain a mutation that eliminates the glycosylation site within the constant region of an IgG heavy chain.

In another embodiment, the constant region includes a CH2 domain and at least a portion of a hinge region. The hinge region can be derived from an immunoglobulin heavy chain, e.g., IgG1, IgG2, IgG3, IgG4, or other classes. Preferably, the hinge region is derived from human IgG1, IgG2, IgG3, IgG4, or other suitable classes. The IgG1 hinge region has three cysteines, two of which are involved in disulfide bonds between the two heavy chains of the immunoglobulin. These same cysteines permit efficient and consistent disulfide bonding formation between Fc portions. Therefore, a preferred hinge region of the present invention is derived from IgG1, more preferably from human IgG1. In some embodiments, the first cysteine within the human IgG1 hinge region is mutated to another amino acid, preferably serine. The IgG2 isotype hinge region has four disulfide bonds that tend to promote oligomerization and possibly incorrect disulfide bonding during secretion in recombinant systems. A suitable hinge region can be derived from an IgG2 hinge; the first two cysteines are each preferably mutated to another amino acid. The hinge region of IgG4 is known to form interchain disulfide bonds inefficiently. However, a suitable hinge region for the present invention can be derived from the IgG4 hinge region, preferably containing a mutation that enhances correct formation of disulfide bonds between heavy chain-derived moieties (Angal S, et al. (1993) Mol. Immunol., 30:105-8). More preferably the hinge region is derived from a human IgG4 heavy chain.

In one embodiment, the constant region includes a CH2 domain derived from a first antibody isotype and a hinge region derived from a second antibody isotype. In a specific embodiment, the CH2 domain is derived from a human IgG4 heavy chain, while the hinge region is derived from an altered human IgG1 heavy chain.

In accordance with the present invention, the constant region can contain CH2 and/or CH3 domains and a hinge region that are derived from different antibody isotypes, i.e., a hybrid constant region. For example, in one embodiment, the constant region contains CH2 and/or CH3 domains derived from IgG2 or IgG4 and a mutant hinge region derived from IgG1. Alternatively, a mutant hinge region from another IgG subclass is used in a hybrid constant region. For example, a mutant form of the IgG4 hinge that allows efficient disulfide bonding between the two heavy chains can be used. A mutant hinge can also be derived from an IgG2 hinge in which the first two cysteines are each mutated to another amino acid. Assembly of such hybrid constant regions has been described in U.S. Patent Publication No. 20030044423, the disclosure of which is hereby incorporated by reference.

In one embodiment, in accordance with the present invention, the constant region can contain CH2 and/or CH3 has one of the mutation described in the Table D below, or any combination thereof.

and a heavy chain constant domain derived from a human IgG1 heavy chain constant domain, optionally with a substitution or a combination of substitutions selected from the group consisting of T250Q/M428L; M252Y/S254T/T256E+ H433K/N434F; E233P/L234V/L235A/G236A +A327G/ A330S/P331S; E333A; S239D/A330L/I332E; P257I/ Q311; K326W/E333S; S239D/I332E/G236A; N297A; L234A/L235A; N297A+M252Y/S254T/T256E; K444A, and K322A, preferably selected from the group consisting of N297A optionally in combination with M252Y/S254T/ T256E, and L234A/L235A.

In another specific aspect, the antibody or antigen-binding fragment thereof comprises a light chain constant domain derived from a human kappa light chain constant domain and a heavy chain constant domain derived from a human IgG4 heavy chain constant domain, optionally with a sub-

TABLE D

Suitable human engineered Fc domain of an antibody

| Engineered Fc | Isotype | Mutations | FcR/C1q Binding | Effector Function |
|---|---|---|---|---|
| hIgG1e1-Fc | IgG1 | T250Q/M428L | Increased binding to FcRn | Increased half-life |
| hIgG1e2-Fc | IgG1 | M252Y/S254T/T256E + H433K/N434F | Increased binding to FcRn | Increased half-life |
| hIgG1e3-Fc | IgG1 | E233P/L234V/L235A/G236A + A327G/A330S/P331S | Reduced binding to FcγRI | Reduced ADCC and CDC |
| hIgG1e4-Fc | IgG1 | E333A | Increased binding to FcγRIIIa | Increased ADCC and CDC |
| hIgG1e5-Fc | IgG1 | S239D/A330L/I332E | Increased binding to FcγRIIIa | Increased ADCC |
| hIgG1e6-Fc | IgG1 | P257I/Q311 | Increased binding to FcRn | Unchanged half-life |
| hIgG1e7-Fc | IgG1 | K326W/E333S | Increased binding to C1q | Increased CDC |
| hIgG1e9-Fc | IgG1 | S239D/I332E/G236A | Increased FcγRIIa/FcγRIIb ratio | Increased macrophage phagocytosis |
| hIgG1e9-Fc | IgG1 | N297A | Reduced binding to FcγRI | Reduced ADCC and CDC |
| hIgG1e9-Fc | IgG1 | LALA (L234A/L235A) | Reduced binding to FcγRI | Reduced ADCC and CDC |
| hIgG1e10-Fc | IgG1 | N297A + YTE (N298A + M252Y/S254T/T256E) | Reduced binding to FcγRI Increased binding to FcRn | Reduced ADCC and CDC Increased half-life |
| hIgG1e11-Fc | IgG1 | K322A | Reduced binding to C1q | Reduced CDC |
| hIgG2e1-Fc | IgG4 | S228P | — | Reduced Fab-arm exchange |
| hIgG4e1-Fc | IgG4 | LALA (L234A/L235A) | Increased binding to FcRn | Increased half-life |
| hIgG4e2-Fc | IgG4 | S228P + YTE (S228P + M252Y/S254T/T256E) | — Increased binding to FcRn | Reduced Fab-arm exchange Increased half-life |
| hIgG4e3-Fc | IgG4 | K444A | | Abolition of cleavage motif at the Cter of the antibody |
| hIgG1e3-Fc | IgG1 | K444A | | Abolition of cleavage motif at the Cter of the antibody |

Numbering of residues in the heavy chain constant region is according to EU numbering (Edelman, G. M. et al., Proc. Natl. Acad. USA, 63, 78-85 (1969); see Worldwide Website: imgt.org/I MGTScientificChart/Numbering/ Hu_IGHGnber.htm#refs).

In one specific aspect, the antibody or antigen-binding fragment thereof comprises a light chain constant domain derived from a human kappa light chain constant domain stitution or a combination of substitutions selected from the group consisting of S228P; L234A/L235A, S228P+M252Y/ S254T/T256E, and K444A.

In certain embodiments, amino acid modifications may be introduced into the Fc region of an antibody provided herein to generate an Fc region variant. In certain embodiments, the Fc region variant possesses some, but not all, effector functions. Such antibodies may be useful, for example, in applications in which the half-life of the antibody in vivo is important, yet certain effector functions are unnecessary or deleterious. Examples of effector functions include complement-dependent cytotoxicity (CDC) and antibody-directed complement-mediated cytotoxicity (ADCC). Numerous substitutions or substitutions or deletions with altered effector function are known in the art.

In one embodiment, the constant region contains a mutation that reduces affinity for an Fc receptor or reduces Fc effector function. For example, the constant region can contain a mutation that eliminates the glycosylation site within the constant region of an IgG heavy chain. Preferably, the CH2 domain contains a mutation that eliminates the glycosylation site within the CH2 domain.

In one embodiment, the anti-hPD1 according to the invention has a heavy chain constant domain of SEQ ID NO: 39 and/or a light chain constant domain of SEQ ID NO: 40, particularly a heavy chain constant domain of SEQ ID NO: 39 and a light chain constant domain of SEQ ID NO: 40.

In one embodiment, the anti-hPD1 according to the invention has a heavy chain constant domain of SEQ ID NO: 47 and/or a light chain constant domain of SEQ ID NO: 40, particularly a heavy chain constant domain of SEQ ID NO: 47 and a light chain constant domain of SEQ ID NO: 40.

TABLE E

Example of a heavy chain constant domain and a light chain constant domain suitable for the humanized antibody according to the invention.

| | |
|---|---|
| Heavy chain constant domain (IgG4m-S228P) SEQ ID NO: 39 | ASTKGPSVFPLAPCSRSTSESTAALGCLVKDYFPEPV TVSWNSGALTSGVHTFPAVLQSSGLYSLSSVVTVPSS SLGTKTYTCNVDHKPSNTKVDKRVESKYGPPCPPCPA PEFLGGPSVFLFPPKPKDTLMISRTPEVTCVVVDVSQ EDPEVQFNWYVDGVEVHNAKTKPREEQFNSTYRVVSV LTVLHQDWLNGKEYKCKVSNKGLPSSIEKTISKAKGQ PREPQVYTLPPSQEEMTKNQVSLTCLVKGFYPSDIAV EWESNGQPENNYKTTPPVLDSDGSFFLYSRLTVDKSR WQEGNVFSCSVMHEALHNHYTQKSLSLSPGK |
| Light chain constant domain (CLkappa) SEQ ID NO: 40 | RTVAAPSVFIFPPSDEQLKSGTASVVCLLNNFYPREA KVQWKVDNALQSGNSQESVTEQDSKDSTYSLSSTLTL SKADYEKHKVYACEVTHQGLSSPVTKSFNRGEC |
| Heavy chain constant domain (IgG1m-N298A) SEQ ID NO: 47 | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSCDKTHTCPP CPAPELLGGPSVFLFPPKPKDTLMISRTPEVTCVVVD VSHEDPEVKFNWYVDGVEVHNAKTKPREEQYASTYRV VSVLTVLHQDWLNGKEYKCKVSNKALPAPIEKTISKA KGQPREPQVYTLPPSRDELTKNQVSLTCLVKGFYPSD IAVEWESNGQPENNYKTTPPVLDSDGSFFLYSKLTVD KSRWQQGNVFSCSVMHEALHNHYTQKSLSLSPGK |

The alteration of amino acids near the junction of the Fc portion and the non-Fc portion can dramatically increase the serum half-life of the Fc fusion protein (PCT publication WO 01/58957). Accordingly, the junction region of a protein or polypeptide of the present invention can contain alterations that, relative to the naturally-occurring sequences of an immunoglobulin heavy chain and erythropoietin, preferably lie within about 10 amino acids of the junction point. These amino acid changes can cause an increase in hydrophobicity. In one embodiment, the constant region is derived from an IgG sequence in which the C-terminal lysine residue is replaced. Preferably, the C-terminal lysine of an IgG sequence is replaced with a non-lysine amino acid, such as alanine or leucine, to further increase serum half-life.

In particular, K444 amino acid in the IgG1 or IgG4 domain may be substituted by an alanine to reduce proteolytic cleavage. Then, in one embodiment, the anti-PD1 antibody comprises at least one further amino acid substitution consisting of K444A.

In one embodiment, the anti-PD1 antibody comprises an additional cysteine residue at the C-terminal domain of the IgG to create an additional disulfide bond.

In certain embodiments, an antibody may be altered to increase, decrease or eliminate the extent to which it is glycosylated. Glycosylation of polypeptides is typically either "N-linked" or "0-linked."

"N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

"O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used. Addition or deletion of N-linked glycosylation sites to the antibody may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an antibody.

The invention also relates to a humanized anti-PD-1 antibody or antigen-binding fragment thereof:
  which has a T20 humanness score greater than 85%;
  which presents a high manufacturability when produced in mammalian cells;
  which presents a high productivity yield in mammalian cells;
  which has a binding affinity (KD) for a human PD-1 equal or lower than $10^{-7}$ M;
  which has an antagonist activity and inhibits the binding of human PD-L1 and/or PD-L2 to human PD-1, preferably PD-L1 and PD-L2;
  which block or inhibits PD-1 signaling (SHP-1 phosphorylation and recruitment);
  which enhances T-cell activation, notably, (inhibition pSHP-1 and TCR mediated NFAT activation, IFN-gamma and IL-2 secretion;
  which promotes anti-tumor immune response; and/or
  which demonstrates a good pharmacokinetics and pharmacodynamics in vivo.

For purposes of this invention, "humanness" is measured using the T20 score analyzer to quantify the humanness of the variable region of monoclonal antibodies as described in Gao S H, Huang K, Tu H, Adler A S. BMC Biotechnology. 2013: 13:55.

A web-based tool is provided to calculate the T20 score of antibody sequences using the T20 Cutoff Human Databases: abAnalyzer.lakepharma.com. In computing a T20 score, an input VH, VK, or VL variable region protein sequence is first assigned Kabat numbering, and CDR residues are identified. The full-length sequence or the framework only sequence (with CDR residues removed) is compared to every sequence in a respective antibody database using the blastp protein-protein BLAST algorithm. The sequence identity between each pairwise comparison is isolated, and after every sequence in the database has been analyzed, the sequences are sorted from high to low based on the sequence identity to the input sequence. The percent identity of the Top 20 matched sequences is averaged to obtain the T20 score.

For each chain type (VH, VK, VL) and sequence length (full-length or framework only) in the "All Human Databases," each antibody sequence was scored with its respective database using the T20 score analyzer. The T20 score was obtained for the top 20 matched sequences after the input sequence itself was excluded (the percent identity of sequences 2 through 21 were averaged since sequence 1 was always the input antibody itself). The T20 scores for each group were sorted from high to low. The decrease in score was roughly linear for most of the sequences; however, the T20 scores for the bottom ~15% of antibodies started decreasing sharply. Therefore, the bottom 15 percent of sequences were removed and the remaining sequences formed the T20 Cutoff Human Databases, where the T20 score cutoff indicates the lowest T20 score of a sequence in the new database.

As used herein, a "humanized antibody" is one that has a T20 humanness score of at least 80% or at least 85%, more preferably at least 88%, even more preferably at least 90%, most preferably a T20 humanness score comprised between 85% and 95%, preferably between 88% and 92%.

Accordingly, the humanized anti-PD1 antibody according to the invention has a T20 humanness score of at least 80% or at least 85%, more preferably at least 88%, even more preferably at least 90%, most preferably a T20 humanness score comprised between 85% and 95%, preferably between 88% and 92%.

In one embodiment, the humanized anti-hPD1 antibody or antigen-binding fragment thereof as disclosed herein as an improved production yield, preferably in comparison with a correspondent chimeric antibody. Particularly, such humanized anti-hPD1 antibody has a production yield greater than 5 mg/L, 6mg/L, 7 mg/L, 8 mg/L or 9 mg/L in CHO cells, preferably greater than 1 or 2 g/L. Alternatively or additionally, such humanized anti-hPD1 antibody has a production yield greater than 2 mg/L, 3 mg/L or 4 mg/L in COS cells, preferably greater than 4 mg/L.

In another embodiment, such humanized anti-hPD1 antibody has a production yield of at least twice the production yield of a correspondent chimeric antibody.

The affinity of an antibody can be a measure of its binding with a specific antigen at a single antigen-antibody site and is in essence the summation of all the attractive and repulsive forces present in the interaction between the antigen-binding site of an antibody and a particular epitope. The affinity of an antibody to a particular antigen (e.g. PD-1) may be expressed by the equilibrium constant K of dissociation, defined by the equation Kd=[Ag][Ab]/[Ag Ab], which represents the affinity of the antibody-combining site; where [Ag] is the concentration of free antigen (M), [Ab] is the concentration of free antibody (M) and [Ag Ab] is the concentration (M) of the antigen-antibody complex. Where the antigen and antibody react strongly together there will be very little free antigen or free antibody, and hence the equilibrium constant or affinity of the antibody will be low. The average affinity for antibodies is equal or lower than $10^{-7}$ M. In certain aspects, the humanized anti-PD-1 antibody binds human PD-1 with affinities equal or lower than $10^{-8}$ M, preferably equal or lower than $10^{-9}$ M. In one aspect, the affinity is equal or lower than $1,5 \times 10^{-9}$ M. The affinity can be measured by any method available to the person skilled in the art, for example by biosensor analysis such as surface plasmon resonance (SPR) Biacore Analysis, Blitz analysis and Scatchard plot. More specifically, the binding affinity is measured by Biacore as detailed in Example 2. The humanized antibody of the invention has a better affinity than the chimeric antibody.

Binding affinity can be expressed $K_D$ or dissociation constant, and an increased binding affinity corresponds to a decreased $K_D$. One way of determining binding affinity of antibodies to PD-1 is by measuring binding affinity of Fab fragments of the antibody. To obtain Fab fragments, an antibody can be cleaved with papain or expressed recombinantly. The affinity of an anti-PD-1 Fab fragment of an antibody can be determined by surface plasmon resonance (BIIAcore3000™ surface plasmon resonance (SPR) system, BIAcore, INC, Piscaway N.J.). Kinetic association rates ($k_{on}$) and dissociation rates ($k_{off}$) (generally measured at 25° C.) are obtained; and equilibrium dissociation constant ($K_D$) values are calculated as $k_{off}/k_{on}$.

Particularly, the antibodies provided herein bind to human PD-1 with an affinity constant (KD) equal to or lower than 0.75 to 1.34 nM, preferably equal to or lower than 0.75 to 1 nM, more preferably equal to or lower than 0.75 to 0.8 nM, as may be determined by Blitz analysis. This system allows the measurement of rate and affinity constants for binding interactions ($k_a$, $k_d$, $K_D$).

In an embodiment, the invention relates to a humanized anti-hPD-1 antibody or antigen-binding fragment thereof as defined above that partially or fully, in particular fully, inhibits the binding of PDL-1 and/or PDL-2 to human PD-1.

Such a humanized antibody of the invention specifically binds hPD-1 and antagonizes the interaction between PD-1 and PD-L1 and/or PD-L2. Particularly, the humanized anti-hPD-1 antibody or antigen-binding fragment thereof as defined above is an antagonist of the binding of human PD-L1 and/or PD-L2 to human PD-1, preferably of human PD-L1 and PD-L2 to human PD-1.

In some examples, an anti-PD-1 antibody described herein suppresses the PD-1 signaling pathway by at least 20%, at least 40%, at least 50%, at least 75%, at least 90%, at least 100%, or by at least 2-fold, at least 5-fold, at least 10-fold, at least 20-fold, at least 50-fold, at least 100-fold, or at least 1000-fold. In particular, the humanized anti-hPD-1 antibody or antigen-binding fragment thereof is capable of reducing or inhibiting the binding of PD-L1 and/or PD-L2 to PD-1 by at least 50%, 60%, 70%, preferably 80%, more preferably 90% or most preferably 100%, as compared to a negative control molecule, in a binding assay, such as a competition ELISA assay. Such an assay is disclosed in Sebaugh J L. Guidelines for accurate EC50/1050 estimation. Pharm. Stat. 2011; 10: 128-134 and in Example 3. The humanized antibody of the invention has an 1050 as measured by this assay of less than 50 ng/ml, in particular less than 40 ng/ml and optionally less than 20 ng/ml. In comparison, the chimeric antibody has an IC50 of more than 50 ng/ml, i.e., about 60 ng/ml. Alternatively, the capacity of the humanized antibody of the invention to antagonize the binding of PD-L1 on PD-1 can also be measured by a competition assay with PD-L1 for PD-1 by Blitz and Biacore as detailed in Example 4.

Methods for determining antibody specificity and affinity by competitive inhibition are known in the art (see, e.g., Harlow et al., Antibodies: A Laboratory Manual, Cold Spring Harbor Laboratory Press, Cold Spring Harbor, NY (1998); Colligan et al., Current Protocols in Immunology, Green Publishing Assoc., NY (1992; 1993); Muller, Meth. Enzym. 92:589-601 (1983)) and described in the examples below.

Methods for determining the antagonist activity of an antibody are known in the art, and are for example ELISA, biosensor analysis such as Biacore and Blitz.

Nucleic Acid Molecules Encoding Anti-PD1 Antibody, Recombinant Expression Vectors and Host Cells Also disclosed herein are nucleic acids encoding the humanized anti-PD-1 antibody or antigen binding fragment thereof described herein, any light or heavy chain thereof, vectors such as expression vectors or recombinant viruses comprising these nucleic acids, and host cells comprising the nucleic acids and/or vectors.

Nucleic Acid Sequence

The invention also relates to a nucleic acid molecule or a group of nucleic acid molecules encoding the humanized anti-hPD-1 antibody or antigen binding fragment thereof as defined above or any light or heavy chain thereof.

Antibody DNA sequences can for example be amplified from RNA of cells that synthesize an immunoglobulin, synthesized using PCR with cloned immunoglobulins, or synthesized via oligonucleotides that encode known signal peptide amino acid sequences. Preferably, the peptide signal comprises or consists of the amino acid sequence of SEQ ID NO: 45 for the VH and/or CH; and/or of the amino acid sequence of SEQ ID NO: 46 for the VL and/or CL. Particularly, the peptide signal is in the N-terminal of the CH, VH, CL and/or VL.

Such nucleic acid may encode an amino acid sequence comprising the VL and/or an amino acid sequence comprising the VH of the antibody (e.g., the light and/or heavy chains of the antibody). Such nucleic acid may be readily isolated and sequenced using conventional procedures.

In one embodiment, the nucleic acid molecules encoding the humanized anti human PD-1 antibody comprises:
  a first nucleic acid molecule encoding a variable heavy chain domain of SEQ ID NO: 21, optionally with a peptide signal of SEQ ID NO. 45, and
  a second nucleic acid molecule encoding a variable light chain domain of SEQ ID NO: 24, optionally with a peptide signal of SEQ ID NO: 46.

In one embodiment, the nucleic acid molecules encoding the humanized anti-human PD-1 antibody comprises:
  a first nucleic acid molecule of SEQ ID NO: 48 encoding a variable heavy chain domain, optionally with a nucleic acid sequence encoding a peptide signal of SEQ ID NO. 45, and
  a second nucleic acid molecule of SEQ ID NO: 49 encoding a variable light chain domain, optionally with a nucleic acid sequence encoding a peptide signal of SEQ ID NO: 46.

In one specific embodiment, the nucleic acid molecules encoding the humanized anti-human PD-1 antibody comprises:
  a first nucleic acid molecule of SEQ ID NO: 50 encoding a heavy chain, and
  a second nucleic acid molecule of SEQ ID NO: 51 encoding a light chain.

In one embodiment, the nucleic acid molecule is an isolated, particularly non-natural, nucleic acid molecule.

The nucleic acid molecule or group of nucleic acid molecules encoding a humanized anti-PD1 antibody according to the invention is(are) preferably comprised in a vector or a group of vectors.

Vectors

In another aspect, the invention relates to a vector comprising the nucleic acid molecule or the group of nucleic acid molecules as defined above.

As used herein, a "vector" is a nucleic acid molecule used as a vehicle to transfer genetic material into a cell. The term "vector" encompasses plasmids, viruses, cosmids and artificial chromosomes. In general, engineered vectors comprise an origin of replication, a multicloning site and a selectable marker. The vector itself is generally a nucleotide sequence, commonly a DNA sequence, that comprises an insert (transgene) and a larger sequence that serves as the "backbone" of the vector. Modern vectors may encompass additional features besides the transgene insert and a backbone: promoter, genetic marker, antibiotic resistance, reporter gene, targeting sequence, protein purification tag. Vectors called expression vectors (expression constructs) specifically are for the expression of the transgene in the target cell, and generally have control sequences.

In one embodiment, both the heavy and light chain coding sequences and/or the constant region of the humanized anti-PD1 antibody are included in one expression vector. Each of the heavy chain coding sequence and the light chain coding sequence may be in operable linkage to a suitable promoter. Alternatively, expression of both the heavy chain and the light chain may be driven by the same promoter. In another embodiment, each of the heavy and light chains of the antibody is cloned in to an individual vector. In the latter case, the expression vectors encoding the heavy and light chains can be co-transfected into one host cell for expression of both chains, which can be assembled to form intact antibodies either in vivo or in vitro. Alternatively, the expression vector encoding the heavy chain and that encoding the light chain can be introduced into different host cells for expression each of the heavy and light chains, which can then be purified and assembled to form intact antibodies in vitro.

The nucleic acid molecule encoding the humanized anti-PD-1 antibody or antibody fragment thereof can be cloned into a vector by those skilled in the art, and then transformed into host cells. Accordingly, the present invention also provides a recombinant vector, which comprises a nucleic acid molecule encoding the anti-PD-1 antibody or fragment thereof of the present invention. In one preferred embodiment, the expression vector further comprises a promoter and a nucleic acid sequence encoding a secretion signal peptide, and optionally at least one drug-resistance gene for screening.

Suitable expression vectors typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence.

The methods known to the artisans in the art can be used to construct an expression vector containing the nucleic acid sequence of the anti-PD1 antibody described herein and appropriate regulatory components for transcription/translation. These methods include in vitro recombinant DNA techniques, DNA synthesis techniques, in vivo recombinant techniques, etc. The DNA sequence is efficiently linked to a proper promoter in the expression vector to direct the synthesis of mRNA. The expression vector may further comprise a ribosome-binding site for initiating the translation, transcription terminator and the like.

An expression vector can be introduced into host cells using a variety of techniques including calcium phosphate transfection, liposome-mediated transfection, electroporation, and the like. Preferably, transfected cells are selected and propagated wherein the expression vector is stably integrated in the host cell genome to produce stable transformants. Techniques for introducing vectors into eukaryotic cells and techniques for selecting stable transformants using a dominant selectable marker are described by Sambrook, by Ausubel, by Bebbington, "Expression of Antibody Genes in Nonlymphoid Mammalian Cells," in 2 METHODS: A companion to methods in enzymology 136 (1991), and by Murray (ed.), Gene transfer and expression protocols (Humana Press 1991). Suitable cloning vectors are described by Sambrook et al. (eds.), MOLECULAR CLONING: A LABORATORY MANUAL, Second Edition (Cold Spring Harbor Press 1989) (hereafter "Sambrook"); by Ausubel et al. (eds.), CURRENT PROTOCOLS IN MOLECULAR BIOLOGY (Wiley Interscience 1987) (hereafter "Ausubel"); and by Brown (ed.), MOLECULAR BIOLOGY LABFAX (Academic Press 1991).

Host Cells

The nucleic acid molecules, group of nucleic acid molecules and/or the vectors of the invention can be comprised in a host cell, particularly for the humanized anti-human PD-1 antibody production purposes. The invention thus provides host cells comprising at least a nucleic acid molecule and/or a group of nucleic acid molecule and/or a vector described hereabove.

As used herein, the term "host cell" is intended to include any individual cell or cell culture that can be or has been recipient of vectors, exogenous nucleic acid molecules, and polynucleotides encoding the antibody of the present invention and/or recipients of the antibody itself. The introduction of the respective material into the cell can be carried out by way of transformation, transfection and the like. The term "host cell" is also intended to include progeny or potential progeny of a single cell. Suitable host cells include prokaryotic or eukaryotic cells, and also include but are not limited to bacteria, yeast cells, fungi cells, plant cells, and animal cells such as insect cells and mammalian cells, e.g., murine, rat, rabbit, macaque or human.

In one embodiment, a host cell comprises (e.g., has been transformed with): (1) a vector comprising a nucleic acid that encodes an amino acid sequence comprising the VL of the antibody and/or an amino acid sequence comprising the VH of the antibody and/or the constant region of the antibody, or (2) a first vector comprising a nucleic acid that encodes an amino acid sequence comprising the VL of the antibody and a second vector comprising a nucleic acid that encodes an amino acid sequence comprising the VH of the antibody.

A method of humanized anti-PD1 antibody production is also provided herein. The method comprises culturing a host cell comprising a nucleic acid encoding the antibody, as provided above, under conditions suitable for expression of the antibody, and optionally recovering the antibody from the host cell (or host cell culture medium). Particularly, for recombinant production of a humanized anti-PD1 antibody, nucleic acid encoding an antibody, e.g., as described above, is isolated and inserted into one or more vectors for further cloning and/or expression in a host cell.

Suitable host cells for producing humanized anti-PD-1 antibodies include, but are not limited to, eukaryotic cells such as mammalian cells, plant cells, insect cells or yeast cells. Mammalian cells are especially preferred eukaryotic hosts because mammalian cells provide suitable post-translational modifications such as glycosylation. Preferably, such suitable eukaryotic host cell may be fungi such as *Pichia pastoris, Saccharomyces cerevisiae, Schizosaccharomyces pombe*; insect cell such as *Mythimna separate*; plant cell such as tobacco, and mammalian cells such as BHK cells, 293 cells, CHO cells, NSO cells and COS cells. Other examples of useful mammalian host cell lines are CV-1 in Origin with SV40 genes cell (COS cell), monkey kidney CV1 line transformed by SV40 (COS-7); human embryonic kidney line (293 or 293 cells as described, e.g., in Graham, F.L. et al, J. Gen Virol. 36 (1977) 59-74); baby hamster kidney cells (BHK); mouse Sertoli cells (TM4 cells as described, e.g., in Mather, J. P., Biol. Reprod. 23 (1980) 243-252); Human Epithelial Kidney cell (HEK cell); monkey kidney cells (CV1); African green monkey kidney cells (VERO-76); human cervical carcinoma cells (HELA); canine kidney cells (MDCK; buffalo rat liver cells (BRL 3 A); human lung cells (W138); human liver cells (Hep G2); mouse mammary tumor (MMT 060562); TRI cells, as described, e.g., in Mather, J.P. et al, Annals N.Y. Acad. Sci. 383 (1982) 44-68; MRC 5 cells; and FS4 cells. Other useful mammalian host cell lines include Chinese hamster ovary (CHO) cells, including DHFR" CHO cells (Urlaub, G. et al, Proc. Natl. Acad. Sci. USA 77 (1980) 4216-4220); and myeloma cell lines such as YO, NSO and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, NJ (2004), pp. 255-268. For example, mammalian cell lines that are adapted to grow in suspension may be useful.

Particularly, the host cell of the present invention is selected from the group consisting of CHO cell, COS cell, NSO cell, and HEK cell.

For a mammalian host, the transcriptional and translational regulatory signals of the expression vector may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Stable transformants that produce a humanized antibody according to the invention can be identified using a variety of methods. After molecule-producing cells have been identified, the host cells are cultured under conditions (e.g. temperature, medium) suitable for their growth and for humanized antibody expression. The humanized antibody is then isolated and/or purified by any methods known in the art. These methods include, but are not limited to, conventional renaturation treatment, treatment by protein precipitant (such as salt precipitation), centrifugation, cell lysis by osmosis, sonication, supercentrifugation, molecular sieve chromatography or gel chromatography, adsorption chromatography, ion exchange chromatography, HPLC, any other liquid chromatography, and the combination thereof. As described, for example, by Coligan, humanized antibody isolation techniques may particularly include affinity chromatography with Protein-A Sepharose, size-exclusion chromatography and ion exchange chromatography. Protein A preferably is used to isolate the antibody of the invention.

Antibody Conjugates

The present disclosure also provides an "antibody conjugate" also called "immunoconjugate" comprising the humanized anti-PD-1 antibody or antibody fragment thereof described herein and a second suitable agent, which can be a therapeutic agent or diagnostic agent. The invention also provides immunoconjugates comprising an humanized anti-PD1 antibody or antibody fragment thereof conjugated to one or more cytotoxic agents, such as chemotherapeutic agents or drugs (e.g., an immunosuppressant), growth inhibitory agents, toxins (e.g., protein toxins, immunotoxins, cytotoxins, enzymatically active toxins of bacterial, fungal, plant, or animal origin, or fragments thereof), radiotoxin, radioactive isotopes, non-proteinaceous polymers e.g., polyethylene glycol, polypropylene glycol, or polyoxyalkylenes. The antibody conjugates of the invention can be used to modify a given biological response, and the drug moiety is not to be construed as limited to classical chemical therapeutic agents. For example, the drug moiety may be a protein or polypeptide possessing a desired biological activity. The term "immunoconjugated" relates herein to the chemical cross-linking or covalent attachment of another molecule/moiety to the humanized anti-PD1 antibody according to the invention by recombinant methods. Methods for preparing an immunoconjugate are well known in the art (see, e.g., WO 2014/160160, U.S. Pat. Nos. 5,208,020 and 5,416,064; and Chari et al., 1992 Cancer Res. 52:127-131).

Pharmaceutical Composition

The present invention also relates to a pharmaceutical composition comprising the humanized anti-human PD1 antibody or antibody fragment thereof, an antibody conjugate as disclosed above, the nucleic acid molecule, the group of nucleic acid molecules, the vector and/or the host cells as described hereabove, preferably as the active ingredient or compound. The formulations can be sterilized and, if desired, mixed with auxiliary agents such as pharmaceutically acceptable carriers and excipients which do not deleteriously interact with the humanized anti-human PD-1 antibody or antibody fragment thereof, the antibody conjugate, nucleic acid, vector and/or host cell of the invention. Optionally, the pharmaceutical composition may further comprise an additional therapeutic agent as detailed below.

Preferably, the pharmaceutical compositions of the present invention may comprise a humanized anti-human PD-1 antibody or antibody fragment thereof, a nucleic acid molecule, a group of nucleic acid molecules, a vector and/or the host cells, as described herein, in combination with one or more pharmaceutically or physiologically acceptable carriers, diluents, excipients, salt, and anti-oxidant as described hereafter. Desirably, a pharmaceutically acceptable form is employed which does not adversely affect the desired immune potentiating effects of the humanized anti-PD1 antibody according to the invention. To facilitate administration, the humanized anti-human PD-1 antibody or antibody fragment thereof as described herein can be made into a pharmaceutical composition for in vivo administration. The means of making such a composition have been described in the art (see, for instance, Remington: The Science and Practice of Pharmacy, Lippincott Williams & Wilkins, 21st edition (2005).

The pharmaceutical composition according to the invention can be formulated for any conventional route of administration including a topical, enteral, oral, parenteral, intra-nasal, intravenous, intra-arterial, intramuscular, intra-tumoral, subcutaneous or intraocular administration and the like. Preferably, the pharmaceutical composition according to the invention is formulated for enteral or parenteral route of administration. Compositions and formulations for parenteral administration may include sterile aqueous solutions that may also contain buffers, diluents and other suitable additives such as, but not limited to, penetration enhancers, carder compounds and other pharmaceutically acceptable carriers or excipients.

The pharmaceutical composition may be prepared by mixing an agent having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

A solid pharmaceutically acceptable vehicle may include one or more substances which may also act as flavoring agents, lubricants, solubilizers, suspending agents, dyes, fillers, glidants, compression aids, inert binders, sweeteners, preservatives, dyes, coatings, or tablet-disintegrating agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. Pharmaceutically acceptable carriers include sterile aqueous solutions or dispersions and sterile powders for the extemporaneous preparation of sterile injectable solutions or dispersion. Except insofar as any conventional media or agent is incompatible with the active compound, use thereof in the pharmaceutical compositions of the invention is contemplated.

The humanized anti-PD1 antibody according to the invention may be dissolved or suspended in a pharmaceutically acceptable liquid vehicle such as water, an organic solvent, ethanol, polyol (for example, glycerol, propylene glycol, and liquid polyethylene glycol, and the like a mixture of both or pharmaceutically acceptable oils or fats and suitable mixtures thereof. The liquid vehicle can contain other suitable pharmaceutical additives such as solubilizers, emulsifiers, buffers, preservatives, sweeteners, flavoring agents, suspending agents, wetting agents, thickening agents, colors, viscosity regulators, stabilizers or osmo-regulators. Suitable examples of liquid vehicles for oral and enteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and peanut oil). For parenteral administration, the vehicle can also be an oily ester such as ethyl oleate and isopropyl myristate. Sterile liquid vehicles are useful in sterile liquid form compositions for enteral administration. The liquid vehicle for pressurized compositions can be a halogenated hydrocarbon or other pharmaceutically acceptable propellant.

The pharmaceutical composition of the invention may further comprise one or more pharmaceutically acceptable salts. A "pharmaceutically acceptable salt" refers to a salt that retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline metals or alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetra-acetic acid (EDTA), sorbitol, tartaric acid, phosphoric acid, and the like.

To facilitate delivery, the anti-PD-1 antibody or its encoding nucleic acids can be conjugated with a chaperon agent. The chaperon agent can be a naturally occurring substance, such as a protein (e.g., human serum albumin, low-density lipoprotein, or globulin), carbohydrate (e.g., a dextran, pullulan, chitin, chitosan, inulin, cyclodextrin or hyaluronic acid), or lipid. It can also be a recombinant or synthetic molecule, such as a synthetic polymer, e.g., a synthetic polyamino acid. Examples of polyamino acids include polylysine (PLL), poly L aspartic acid, poly L-glutamic acid, styrene-maleic acid anhydride copolymer, poly(L-lactide-co-glycolied) copolymer, divinyl ether-maleic anhydride copolymer, N-(2-hydroxypropyl) methacrylamide copolymer (HMPA), polyethylene glycol (PEG), polyvinyl alcohol (PVA), polyurethane, poly(2-ethylacryllic acid), N-isopropylacrylamide polymers, and polyphosphazine. In one example, the chaperon agent is a micelle, liposome, nanoparticle, or microsphere, in which the oligonucleotide/interfering RNA is encapsulated. Methods for preparing such a micelle, liposome, nanoparticle, or microsphere are well known in the art. See, e.g., U.S. Pat. Nos. 5,108,921; 5,354,844; 5,416,016; and 5,527,5285.

Pharmaceutical composition typically must be sterile and stable under the conditions of manufacture and storage. The pharmaceutical composition can be formulated as a solution, micro-emulsion, liposome, or other ordered structure suitable to high drug concentration and/or in suitable for injection. The proper fluidity can be maintained, for example, by the use of a coating such as lecithin, by the maintenance of the required particle size in the case of dispersion and by the use of surfactants.

In one embodiment, the pharmaceutical composition is an injectable composition that may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof. Prolonged absorption of the injectable compositions can be brought about by including in the composition an agent that delays absorption, for example, monostearate salts and gelatin.

Prevention of presence of microorganisms may be ensured both by sterilization procedures, and by the inclusion of various antibacterial and antifungal agents, for example, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

It will be understood by one skilled in the art that the formulations of the invention may be isotonic with human blood that is the formulations of the invention have essentially the same osmotic pressure as human blood. Such isotonic formulations generally have an osmotic pressure from about 250 mOSm to about 350 mOSm. Isotonicity can be measured by, for example, a vapor pressure or ice-freezing type osmometer. Tonicity of a formulation is adjusted by the use of tonicity modifiers. "Tonicity modifiers" are those pharmaceutically acceptable inert substances that can be added to the formulation to provide an isotonicity of the formulation. Tonicity modifiers suitable for this invention include, but are not limited to, saccharides, salts and amino acids.

Pharmaceutical compositions according to the invention may be formulated to release the active ingredients (e.g. the humanized anti-hPD1 antibody of the invention) substantially immediately upon administration or at any predetermined time or time period after administration. The pharmaceutical composition in some aspects can employ time-released, delayed release, and sustained release delivery systems such that the delivery of the composition occurs prior to, and with sufficient time to cause, sensitization of the site to be treated. Means known in the art can be used to prevent or minimize release and absorption of the composition until it reaches the target tissue or organ, or to ensure timed-release of the composition. Such systems can avoid repeated administrations of the composition, thereby increasing convenience to the subject and the physician.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect.

Subject, Regimen and Administration

The present invention relates to a humanized anti-PD1 antibody or fragment thereof, a pharmaceutical composition, a nucleic acid molecule, a group of nucleic acid molecules, a vector or a host cell of the invention for use as a medicament, particularly for use in the prevention or treatment of a disease or disorder in a subject. Examples of treatments are more particularly described hereafter under the section "Methods and Uses". It also relates to the use of a pharmaceutical composition, a nucleic acid, a vector or a host cell of the present invention or a humanized anti-PD1 antibody or antibody fragment thereof in the manufacture of a medicament for treating a disease in a subject. Finally, it relates to a method for treating a disease or a disorder in a subject comprising administering a therapeutically effective amount of a pharmaceutical composition or a humanized anti-PD1 antibody or antibody fragment thereof to the subject. Examples of treatments are more particularly described hereafter under the section "Methods and Uses".

The subject to treat may be a human, particularly a human at the prenatal stage, a new-born, a child, an infant, an adolescent or an adult, in particular an adult of at least 30 years old, 40 years old, preferably an adult of at least 50 years old, still more preferably an adult of at least 60 years old, even more preferably an adult of at least 70 years old.

In a particular embodiment, the subject is immunosuppressed or immunodepressed. Such subjects may be immunosuppressed, immunocompromised or immunodepressed, for example due to the infection by a virus such as HIV, cancer, diabetes, malnutrition, and certain genetic disorders, to treatments with immunosuppressive drugs or to previous treatment by immunotherapy, chemotherapy or radiotherapy. The subject of the invention may be immunodepressed. As used herein, the terms "immunodepressed" and "immunodeficient" are equivalent and may be used interchangeably. As used in the invention, the term "immunodepressed" or "immunocompromised" refers to a state in which the subject has weakened immune defenses. Immunodepressed individuals are incapable of properly managing microorganisms that, under normal conditions, present no danger. The subject of the invention may be immunosuppressed. As used herein, the term "immunosuppressed" refers to a state in which the subject no longer has immune defenses.

Accordingly, the antibody or antigen-binding fragment thereof, the pharmaceutical composition, the isolated nucleic acid molecule or the group of isolated nucleic acid molecules, the vector, or the host cell according to the present invention may be fur use in the prevention or treatment of patients with a lymphopenic disorder.

Particularly, the subject is affected with a disease that may involve the PD-1/PDL-1 pathway, particularly wherein, at least one of the ligands of PD-1 (e.g. PDL-1 and/or PDL-2) or PD-1 is/are expressed, especially overexpressed. Preferably, the subject is suffering from cancer, even more preferably from a PD1, PD-L1 and/or PD-L2 positive cancer or a PD-1 positive cancer. Examples of diseases and cancers are more particularly described hereafter under the section "Methods and Uses".

In a particular embodiment, the subject has already received at least one line of treatment, preferably several lines of treatment, prior to the administration of humanized anti-PD1 antibody according to the invention or of a pharmaceutical composition according to the invention.

Conventional methods, known to those of ordinary skill in the art of medicine, can be used to administer the humanized anti-PD1 antibody or antibody fragment thereof or the pharmaceutical composition disclosed herein to the subject, depending upon the type of diseases to be treated or the site of the disease. This composition can be administered via conventional routes, e.g., administered orally, parenterally, enterally, by inhalation spray, topically, rectally, nasally, buccally, vaginally or via an implanted reservoir. The term "parenterally" as used herein includes subcutaneous, intracutaneous, intravenous, intramuscular, intra-articular, intra-arterial, intra-synovial, intra-sternal, intra-thecal, intra-lesion, intra-tumoral, and intracranial injection or infusion techniques. When administered parenterally, the pharmaceutical composition according to the invention is preferably administered by intravenous route of administration. When administered enterally, the pharmaceutical composition according to the invention is preferably administered by oral route of administration. This composition can also be administered locally.

The form of the pharmaceutical compositions, the route of administration and the dose of administration of the pharmaceutical composition or the humanized anti-PD1 antibody or fragment thereof according to the invention can be adjusted by the man skilled in the art according to the type and severity of the infection, and to the patient, in particular its age, weight, sex, and general physical condition. The compositions of the present invention may be administered in a number of ways depending upon whether local or systemic treatment is desired.

Preferably, the treatment with the humanized anti-PD-1 antibody or fragment thereof or with a pharmaceutical composition according to the invention is administered regularly, preferably between every day, every week or every month, more preferably between every day and every one, two, three or four weeks. In a particular embodiment, the treatment is administered several times a day, preferably 2 or 3 times a day.

The duration of treatment with the humanized anti-PD-1 antibody or fragment thereof or with a pharmaceutical composition according to the invention according to the invention is preferably comprised between 1 day and 20 weeks, more preferably between 1 day and 10 weeks, still more preferably between 1 day and 4 weeks, even more preferably between 1 day and 2 weeks. Alternatively, the treatment may last as long as the disease persists.

The humanized anti-hPD1 antibody disclosed herein may be provided at an effective dose range from about 1 ng/kg body weight to about 30 mg/kg body weight, 1 µg/kg to about 20 mg/kg, 10 µg/kg to about 10 mg/kg, or from 100 µg/kg to 5 mg/kg, optionally every one, two, three or four weeks, preferably by parenteral or oral administration, in particular by intravenous or subcutaneous administration.

Particularly, the humanized anti-hPD1 antibody according to the invention can be administered at a subtherapeutic dose. The term "subtherapeutic dose" as used herein refers to a dose that is below the effective monotherapy dosage levels commonly used to treat a disease, or a dose that currently is not typically used for effective monotherapy with anti-hPD1 antibodies.

Methods and Uses
Use in the Treatment of a Disease

The humanized anti-PD-1 antibody or antigen binding fragment thereof, nucleic acids, vectors, host cells, compositions and methods of the present invention have numerous in vitro and in vivo utilities and applications. For example, the humanized anti-PD-1 antibody or antibody fragment thereof (either in free form or as immunoconjugates), the nucleic acids, the vectors, the host cells, and/or the pharmaceutical compositions described herein can be used as therapeutic agents, diagnostic agents and medical researches. Particularly, any of the humanized anti-PD1 antibody, nucleic acids, vectors, host cells, or pharmaceutical compositions provided herein may be used in therapeutic methods and/or for therapeutic purposes. Particularly, the humanized anti-PD-1 antibody or antibody fragment thereof provided herein may be useful for the treatment of any disease or condition involving PD-1, such as cancer and infection, or other diseases associated with immune deficiency, such as T cell dysfunction.

In one aspect, the invention relates to a method of treatment of a pathology, disease and/or disorder that could be prevented or treated by the inhibition of the binding of PD-L1 and/or PD-L2 to PD-1.

Even more preferably, the invention relates to a method of treatment of a disease and/or disorder selected from the group consisting of a cancer and an infectious disease, preferably a chronic infection, in a subject in need thereof, comprising administering to said subject an effective amount of the anti-PD1 antibody or pharmaceutical composition as defined above. Examples of such diseases are more particularly described hereafter.

The present invention also relates to a humanized anti-hPD1 antibody or antigen binding fragment thereof, a nucleic acid, a group of nucleic acids or a vector encoding such, or a pharmaceutical composition comprising such for use in the treatment of a disorder and/or disease in a subject and/or for use as a medicament or vaccine. It also relates to the use of a humanized anti-hPD1 antibody or antigen binding fragment thereof, a nucleic acid or a vector encoding such, or a pharmaceutical composition comprising such in the manufacture of a medicament for treating a disease and/or disorder in a subject. Finally, it relates to a method for treating a disease or a disorder in a subject comprising administering a therapeutically effective amount of a pharmaceutical composition or a humanized anti-PD1 antibody or antibody fragment thereof to the subject.

In a particular aspect, the invention particularly concerns a humanized anti-hPD1 antibody or antigen binding fragment thereof, a nucleic acid, a group of nucleic acids or a vector encoding such, or a pharmaceutical composition comprising such, as disclosed herein, for use in the treatment of a pathology, disease and/or disorder that could be prevented or treated by the inhibition of the binding of PD-L1 and/or PD-L2 to PD-1.

Accordingly, disclosed herein are methods for treating a disease associated with the PD-1 and/or PD-1/PD-L1 and/or PD-1/PD-L2 signaling pathway comprising administering to a subject in need of a treatment an effective amount of the anti-PD-1 antibody or pharmaceutical composition described herein. Physiological data of the patient (e.g. age, size, and weight) and the routes of administration have also to be taken into account to determine the appropriate dosage, so as a therapeutically effective amount will be administered to the patient.

Disclosed herein, are methods of treating a patient with a disease and/or disorder, the method comprising: (a) identifying a patient in need of treatment; and (b) administering to the patient a therapeutically effective amount of the antibody, nucleic acid, vector or pharmaceutical composition described herein.

In one particular aspect, the subject in need of a treatment may be a human having, at risk for, or suspected of having a disease associated with the signaling pathway mediated by PD-1. Such a patient can be identified by routine medical examination. For example, a subject suitable for the treatment can be identified by examining whether such subject carries PD-1, PD-L1 and/or PD-L2 positive cells. In one embodiment, a subject who needs a treatment is a patient having, suspected of having, or at risk for a disease, preferably a PD-1, PDL1 and/or PDL2 positive disease, even more preferably a disease where PD-1 and/or at least one ligand of PD-1 is overexpressed. In such subject, the disruption of PD-1/PD-L1 and/or PD-1/PD-L2 interaction thanks to the administration of the antibody or pharmaceutical composition according to the invention may enhance immune response of the subject. In some embodiments, the humanized anti-PD-1 antibody or pharmaceutical composition described herein can be used for treating PD-1 positive cells.

Alternatively, due to the effect on the phagocytosis by macrophages which are not specific to PD-L1 or PD-L2 expressing targeted cells, a subject suitable for the treatment can also have PD-L1 and/or PD-L2 negative targeted cells. In one embodiment, a subject who needs a treatment is a patient having, suspected of having, or at risk for a disease which is PDL1 and/or PDL2 negative.

In another aspect the humanized anti-PD-1 antibody or pharmaceutical composition described herein can be administered to a subject, e.g., in vivo, to enhance immunity, preferably in order to treat a disorder and/or disease. Accordingly, in one aspect, the invention provides a method of modifying an immune response in a subject comprising administering to the subject a humanized anti-PD-1 antibody or antigen binding fragment thereof, nucleic acid, vector or pharmaceutical composition of the invention such that the immune response in the subject is modified. Preferably, the immune response is enhanced, increased, stimulated or up-regulated. The humanized anti-hPD-1 antibody or pharmaceutical composition can be used to enhance immune responses such as T cell activation in a subject in need of a treatment. The immune response enhancement can result in the inhibition of the binding of PD-L1 and/or PD-L2 to PD-1 thereby reducing the immunosuppressive environment, stimulating the proliferation and/or the activation of human T-cells and/or the IFNγ secretion by human PBMC.

Alternatively or in addition, the immune response enhancement can result from the activation of phagocytosis of cells by macrophages. This phagocytosis is not limited to cells expressing PD-L1. Indeed, the humanized anti-hPD-1 antibody of the present invention can activate the phagocytosis of any cell by these macrophages, especially cancer cells or infected cells.

The invention particularly provides a method of enhancing an immune response in a subject, comprising administering to the subject a therapeutic effective amount of any of the humanized anti-PD-1 antibody or antigen binding fragment thereof, nucleic acid, vector or pharmaceutical composition comprising such described herein, such that an immune response in the subject is enhanced.

In some embodiments, the amount of the humanized anti-hPD-1 antibody described herein is effective in suppressing the PD-1 signaling (e.g., reducing the PD-1 signaling by at least 20%, 30%, 50%, 80%, 100%, 200%, 400%, or 500% as compared to a control). In other embodiments, the amount of the anti-PD-1 antibody described herein is effective in activating immune responses (e.g., by at least 20%, 30%, 50%, 80%, 100%, 200%, 400%, or 500% as compared to a control).

In some embodiments, the amount of the humanized anti-hPD-1 antibody described herein is effective in the inhibition of the binding of human PD-L1 and/or PD-L2 to human PD-1 e.g., inhibiting the binding by at least 20%, 30%, 50%, 80%, 100%, 200%, 400%, or 500% as compared to a control).

In some embodiments, the amount of the humanized anti-hPD-1 antibody described herein is sufficient to have an antagonist activity of the binding of human PD-L1 and/or PD-L2 to human PD-1 e.g., inhibiting the binding by at least 20%, 30%, 50%, 80%, 100%, 200%, 400%, or 500% as compared to a control).

Cancer

It is known in the art that blockade of PD-1 by antibodies can enhance the immune response to cancerous cells in a patient. Thus, in one aspect, the invention provides an anti-PD1 antibody or a pharmaceutical composition for use in the treatment of a subject having a cancer, comprising administering to the individual an effective amount of the anti-PD1 antibody or pharmaceutical composition, preferably to disrupt or inhibit the PD1/PD-L1 and/or PD1/PD-L2 interaction. Thus, in one aspect, the invention provides an anti-PD-1 antibody or a pharmaceutical composition for use in the treatment of a subject having a cancer, wherein the –anti-PD-1 antibody is capable of activating exhausted T cells, preferably by disrupting or inhibiting the PD1/PD-L1 and/or PD1/PD-L2 interaction. In one aspect, the invention provides an anti-PD-1 antibody or a pharmaceutical composition for use in the treatment of a subject having a cancer, wherein the anti-PD-1 antibody is capable of activating macrophages, preferably by disrupting or inhibiting the PD1/PD-L1 and/or PD1/PD-L2 interaction.

In one embodiment, a subject who needs a treatment is a patient having, suspected of having, or at risk for a disease, preferably a PD-1 or PD-L1 positive cancer, even more preferably a cancer where PD-1 or PD-L1 is expressed or overexpressed. For example, a patient suitable for the treatment can be identified by examining whether such a patient carries PD-L1 positive tumor cells. Additionally or alternatively, the subject suitable for the treatment is a subject having tumor infiltrating T cells that express or overexpress PD-1.

In another embodiment, a subject is a patient having, suspected of having, or at risk for a cancer development, preferably a PD-L1 and/or PD-L2 positive cancer. In some embodiments, the humanized anti-PD-1 antibody or pharmaceutical composition described herein can be used for treating PD-L1 and/or PD-L2 positive tumors. For example, a human patient suitable for the treatment can be identified by examining whether such a patient carries PD-L1 and/or PD-L2 positive cancer cells.

In further aspects, a humanized anti-hPD1 antibody or antibody fragment thereof for use in treating cancer, preferably a PD-L1 and/or PD-L2 positive cancer, even more preferably a cancer wherein PD-L1 and/or PD-L2 is/are overexpressed is provided.

In another embodiment, the invention provides the use of a humanized anti-hPD-1 antibody, or antigen-binding portion thereof, or a pharmaceutical composition as disclosed herein in the manufacture of a medicament for treating a cancer, for instance for inhibiting growth of tumor cells, in a subject, preferably having PD-L1, PD-L2 positive tumor cells.

Accordingly, in one embodiment, the invention provides a method of treating a cancer, for instance of inhibiting growth of tumor cells, in a subject, comprising administering to the subject a therapeutically effective amount of a humanized anti-PD-1 antibody, or antigen-binding portion thereof, or pharmaceutical composition according to the invention. Particularly, the present invention relates to the treatment of a subject using a humanized anti-PD-1 antibody such that growth of cancerous cells is inhibited.

In an aspect of the disclosure, the cancer to be treated is associated with exhausted T cells.

Preferably, by "PD-L1 positive tumor cells" or "PD-L2 positive tumor cells" is intended to refer to a population of tumor cells in which PD-L1 or PD-L2, respectively, are expressed in at least 10% of tumor cells, preferable at least 20, 30, 40 or 50% of tumor cells.

Alternatively or in addition, the humanized anti-hPD-1 antibody of the present invention can also be used for treating a cancer which could be associated with low expression of PD-1 and/or PD-L1, and/or a low number of T cells, especially tumor-infiltrated T cells, and/or a high number of exhausted T cells. Indeed, the humanized anti-hPD-1 antibody of the present invention can surprisingly activate the phagocytosis of any cell (cells expressing or not PD-1 and/or PD-L1) by these macrophages. In this context, patients can be immunosuppressed, immunocompromised or immunodepressed due to the infection by a virus such as HIV, cancer, diabetes, malnutrition, and certain genetic disorders, to treatments with immunosuppressive drugs or to previous treatment by immunotherapy, chemotherapy or radiotherapy.

Accordingly, the humanized anti-hPD-1 antibody of the present invention can also be used for treating a cancer with PD-L1 negative tumor cells.

Preferably, by "PD-L1 negative tumor cells" or "PD-L2 negative tumor cells" is intended to refer to a population of tumor cells in which PD-L1 or PD-L2, respectively, are expressed in less than 10% of tumor cells, preferably less than 5% of tumor cells, preferably less than 1% of tumor cells.

Any suitable cancer may be treated with the antibody provided herein can be hematopoietic cancer or solid cancer. Such cancers include carcinoma, cervical cancer, colorectal cancer, esophageal cancer, gastric cancer, gastrointestinal cancer, head and neck cancer, kidney cancer, liver cancer, lung cancer, lymphoma, glioma, mesothelioma, melanoma, stomach cancer, urethral cancer environmentally induced cancers and any combinations of said cancers. The present invention is also useful for treatment of metastatic cancers, especially metastatic cancers that express PD-L1 (Iwai et al. (2005) Int. Immunol. 17: 133-144). Additionally, the invention includes refractory or recurrent malignancies.

In a particular aspect, the cancer is a hematologic malignancy or a solid tumor with high expression of PD-1 and/or PD-L1. Such a cancer can be selected from the group consisting of hematolymphoid neoplasms, angioimmunoblastic T cell lymphoma, myelodysplastic syndrome, acute myeloid leukemia.

In a particular aspect, the cancer is a cancer induced by virus or associated with immunodeficiency. Such a cancer can be selected from the group consisting of Kaposi sarcoma (e.g., associated with Kaposi sarcoma herpes virus); cervical, anal, penile and vulvar squamous cell cancer and oropharyngeal cancers (e.g., associated with human papilloma virus); B cell non-Hodgkin lymphomas (NHL) including diffuse large B-cell lymphoma, Burkitt lymphoma, plasmablastic lymphoma, primary central nervous system lymphoma, HHV-8 primary effusion lymphoma, classic Hodgkin lymphoma, and lymphoproliferative disorders (e.g., associated with Epstein-Barr virus (EBV) and/or Kaposi sarcoma herpes virus); hepatocellular carcinoma (e.g., associated with hepatitis B and/or C viruses); Merkel cell carcinoma (e.g., associated with Merkel cell polyoma virus (MPV)); and cancer associated with human immunodeficiency virus infection (HIV) infection.

Preferably, the cancer to be treated or prevented is selected from the group consisting of metastatic or not metastatic, Melanoma, malignant mesothelioma, Non-Small Cell Lung Cancer, Renal Cell Carcinoma, Hodgkin's Lymphoma, Head and Neck Cancer, Urothelial Carcinoma, Colorectal Cancer, Hepatocellular Carcinoma, Small Cell Lung Cancer Metastatic Merkel Cell Carcinoma, Gastric or Gastroesophageal cancers and Cervical Cancer.

Preferred cancers for treatment include cancers typically responsive to immunotherapy.

By way of example and not wishing to be bound by theory, treatment with an anti-cancer antibody or an anti-cancer immunoconjugate or other current anti-cancer therapy that lead to cancer cell death would potentiate an immune response mediated by PD-1. Accordingly, a treatment of a hyper proliferative disease (e.g., a cancer tumor) may include humanized anti-PD-1 antibody or fragment thereof combined with an anti-cancer treatment, concurrently or sequentially or any combination thereof, which may potentiate an anti-tumor immune response by the host. Preferably, an anti-PD-1 antibody may be used in combination with other immunogenic agents (e.g. ADC), standard cancer treatments, or other antibodies as described hereafter.

Infectious disease

The humanized anti-PD1 antibody or fragment thereof or pharmaceutical compositions of the invention are used to treat patients that have been exposed to particular toxins or pathogens. Accordingly, an aspect of the invention provides a method of treating an infectious disease in a subject comprising administering to the subject a humanized anti-PD-1 antibody, or antigen-binding fragment thereof, or a pharmaceutical composition comprising such, preferably such that the subject is treated for the infectious disease.

Any suitable infection may be treated with the humanized anti-PD1 antibody or antibody fragment provided herein.

Some examples of pathogenic viruses causing infections treatable by methods of the invention include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Particularly, the anti-PD1 antibody or pharmaceutical compositions of the invention are used to treat patients that have chronic viral infection, such infection being caused by viruses selected from the group consisting of Retroviruses, Anellovirus, Circovirus, Herpesvirus, Varicella zoster virus (VZV), Cytomegalovirus (CMV), Epstein-Barr virus (EBV), Polyomavirus BK, Polyomavirus, Adeno-associated virus (AAV), Herpes simplex type 1 (HSV-1), Adenovirus, Herpes simplex type 2 (HSV-2), Kaposi's sarcoma herpesvirus (KSHV), Hepatitis B virus (HBV), GB virus C, Papilloma virus, Hepatitis C virus (HCV), Human immunodeficiency virus (HIV), Hepatitis D virus (HDV), Human T cell leukemia virus type 1 (HTLV1), Xenotropic murine leukemia virus-related virus (XMLV), Rubella virus, German measles, Parvovirus B19, Measles virus, Coxsackie virus.

Some examples of pathogenic bacteria causing infections treatable by methods of the invention include chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lymes disease bacteria.

Some examples of pathogenic fungi causing infections treatable by methods of the invention include *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the invention include Entamoeba histolytica, Balantidium coli, Naegleriafowleri, Acanthamoeba sp., Giardia lambia, Cryptosporidium sp., Pneumocystis carinii, Plasmodium vivax, Babesia microti, Trypanosoma brucei, Trypanosoma cruzi, Leishmania donovani, Toxoplasma gondi, and Nippostrongylus brasiliensis.

In all of the above methods, PD-1 blockade can be combined with other forms of immunotherapy such as cytokine treatment (e.g., interferons, GM-CSF, G-CSF, IL-2), or any therapy, which provides for enhanced presentation of tumor antigens.

Combined Therapy

In particular, the humanized anti-PD-1 antibody or antigen binding fragment thereof according to the present invention can be combined with some other potential strategies for overcoming immune evasion mechanisms with agents in clinical development or already on the market (see table 1 from Antonia et al. Immuno-oncology combinations: a review of clinical experience and future prospects. Clin. Cancer Res. Off. J. Am. Assoc. Cancer Res. 20, 6258-6268, 2014). Such combination with the humanized anti-PD-1 antibody or antigen binding fragment thereof according to the invention may be useful notably for:

1—Reversing the inhibition of adaptive immunity (blocking T-cell checkpoint pathways), for example by using an anti-CTLA4 molecule;

2—Switching on adaptive immunity (promoting T-cell costimulatory receptor signaling using agonist molecules, in particular antibodies);

3—Improving the function of innate immune cells;

4—Activating the immune system (potentiating immune-cell effector function), for example through vaccine-based strategies.

Accordingly, also provided herein are combined therapies for any of the diseases as described herein with the humanized anti-PD-1 antibody or antibody fragment thereof or pharmaceutical composition comprising such as described herein and an additional therapeutic agent. In an aspect, the humanized anti-PD-1 antibody and an additional therapeutic can be present in a pharmaceutical composition as described above. Alternatively, the term "combination therapy" or "combined therapy" as used herein, embraces administration of these agents (e.g., an anti-PD-1 antibody as described herein and a second or additional suitable therapeutic agent) in a sequential manner, that is, wherein each therapeutic agent is administered at a different time, as well as administration of these therapeutic agents, or at least two of the agents, in a substantially simultaneous manner. Sequential or substantially simultaneous administration of each agent can be affected by any appropriate route. The agents can be administered by the same route or by different routes. For example, a first agent (e.g., an anti-PD-1 antibody) can be administered orally, and an additional therapeutic agent (e.g., an anti-cancer agent, an anti-infection agent; or an immune modulator) can be administered intravenously. Alternatively, an agent of the combination selected may be administered by intravenous injection while the other agents of the combination may be administered orally.

In another aspect, the invention relates to a therapeutic mean, in particular a combination product mean, which comprises as active ingredients: a humanized anti-hPD-1 antibody or antigen binding fragment as defined above and an additional and therapeutic agent, wherein said active ingredients are formulated for separate, sequential or combined therapy, in particular for combined or sequential use.

As used herein, the term "sequential" means, unless otherwise specified, characterized by a regular sequence or order, e.g., if a dosage regimen includes the administration of a humanized anti-hPD-1 antibody and the additional or second agent, a sequential dosage regimen could include administration of a humanized anti-hPD-1 antibody before, simultaneously, substantially simultaneously, or after administration of the second agent, but both agents will be administered in a regular sequence or order. The term "separate" means, unless otherwise specified, to keep apart one from the other. The term "simultaneously" means, unless otherwise specified, happening or done at the same time, i.e., the agents of the invention are administered at the same time. The term "substantially simultaneously" means that the agents are administered within minutes of each other (e.g., within 15 minutes of each other) and intends to embrace joint administration as well as consecutive administration, but if the administration is consecutive it is separated in time for only a short period (e.g., the time it would take a medical practitioner to administer two compounds separately).

It should be appreciated that any combination as described herein may be used in any sequence for treating the disorder or disease described herein. The combinations described herein may be selected on the basis of a number of factors, which include but are not limited to the effectiveness of inhibiting or preventing the target disease progression, the effectiveness for mitigating the side effects of another agent of the combination, or the effectiveness of mitigating symptoms related to the target disease. For example, a combined therapy described herein may reduce any of the side effects associated with each individual members of the combination.

The present invention also relates to a method for treating a disease in a subject comprising administering to said subject a therapeutically effective amount of the humanized anti-hPD-1 antibodies or the pharmaceutical composition described herein and a therapeutically effective amount of an additional therapeutic agent.

When the humanized anti-hPD-1 antibody or the pharmaceutical composition described herein is co-used with an additional therapeutic agent, a sub-therapeutic dosage of either the composition or of the second agent, or a sub-therapeutic dosage of both, can be used in the treatment of a subject, preferably a subject having, or at risk of developing a disease or disorder associated with the cell signaling mediated by PD-1. In an aspect, the additional therapeutic agent can be selected in the non-exhaustive list comprising alkylating agents, angiogenesis inhibitors, antibodies, in particular anti-tumor targeting antibodies, antimetabolites, antimitotics, antiproliferatives, antivirals, aurora kinase inhibitors, apoptosis promoters (for example, Bcl-2 family inhibitors), activators of death receptor pathway, Bcr-Abl kinase inhibitors, BiTE (Bi-Specific T cell Engager) antibodies, antibody drug conjugates, biologic response modifiers, Bruton's tyrosine kinase (BTK) inhibitors, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNAs, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteasome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, hypomethylating agents, checkpoints inhibitors, peptide vaccine and the like, epitopes or neoepitopes from tumor antigens, as well as combinations of one or more of these agents.

For instance, the additional therapeutic agent can be selected in the group consisting of chemotherapy, radiotherapy, targeted therapy, anti-tumor targeting antibodies, antiangiogenic agents, hypomethylating agents, cancer vaccines, epitopes or neoepitopes from tumor antigens, myeloid checkpoints inhibitors, other immunotherapies, and HDAC inhibitors.

In a preferred embodiment, the additional therapeutic agent is selected from the group consisting of chemotherapeutic agents, radiotherapy agents, immunotherapeutic agents, cell therapy agents (such as CAR-T cells), antibiotics and probiotics.

Said immunotherapeutic agent can also be an antibody targeting tumoral antigen, particularly selected from the group consisting of anti-Her2, anti-EGFR, anti-CD20, anti-CD19 and anti-CD52. Said antibodies can be cytotoxic antibodies targeting tumor cells or antibodies inducing cytolytic activity of immune cells (such as NK cells, T cells or macrophages) against tumor cells. A non-exhaustive list of such antibodies includes rituximab, pertuzumab, alemtuzumab, atezolizumab, bevacizumab, cetuximab, herceptin, panitumumab, necitumumab, dinutuximab, ramucirumab, olaratumab, ipilimumab, cemiplimab, tremelimumab, CS1001, relatlimab, naxitamab, margetuximab, BAT8001, KN035, isatuximab, andecaliximab, bemarituzumab, trastuzumab, anti-PD1 antibody, anti-PDL-1, anti-CD47 antibody, and anti-SIRPa antibody. In a very particular aspect, the anti-PD-1 antibody of the invention is used in combination with rituximab.

In an embodiment, the invention relates to a combined therapy as defined above, wherein the additional therapeutic agent is particularly selected from the group consisting of therapeutic vaccines, immune checkpoint blockers or activators, in particular of adaptive immune cells (T and B lymphocytes) and antibody-drug conjugates. Preferably, suitable agents for co-use with the humanized anti-hPD-1 antibody or fragment thereof or with the pharmaceutical composition according to the invention include an antibody binding to a co-stimulatory receptor (e.g., OX40, CD40, ICOS, CD27, HVEM or GITR), an agent that induces immunogenic cell death (e.g., a chemotherapeutic agent, a radio-therapeutic agent, an anti-angiogenic agent, or an agent for targeted therapies), an agent that inhibits a checkpoint molecule (e.g., CTLA4, LAG3, TIM3, B7H3, B7H4, BTLA, or TIGIT), a cancer vaccine, an agent that modifies an immunosuppressive enzyme (e.g., IDO1 or iNOS), an agent that targets $T_{reg}$ cells, an agent for adoptive cell therapy, or an agent that modulates myeloid cells.

In an embodiment, the invention relates to a combined therapy as defined above, wherein the second therapeutic agent is an immune checkpoint blocker or activator of adaptive immune cells (T and B lymphocytes) selected from the group consisting of anti-CTLA4, anti-CD2, anti-CD28, anti-CD40, anti-HVEM, anti-BTLA, anti-CD160, anti-TIGIT, anti-TIM-1/3, anti-LAG-3, anti-2B4, and anti-OX40, anti-CD40 agonist, CD40-L, TLR agonists, anti-ICOS, ICOS-L and B-cell receptor agonists.

In one embodiment, the additional or second therapeutic agent is an antibody targeting tumoral antigen, particularly selected from the group consisting of anti-Her2, anti-EGFR, anti-CD20, anti-CD19 and anti-CD52.

Specific examples of second therapeutic agents are provided in WO 2018/053106, pages 36-43, the disclosure thereof being incorporated herein by reference.

Combination therapy could also rely on the combination of the administration of humanized anti-PD1 antibodies or antibody fragment thereof with surgery, chemotherapy (e.g. such as docetaxel or decarbazine), radiotherapy, immunotherapy (e.g. such as antibodies targeting CD40, CTLA-4), gene targeting and modulation and/or other agents such as immune-modulators, angiogenesis inhibitors and any combinations thereof.

Use in Diagnostic

In certain embodiments, the anti-PD1 antibody provided herein is useful for detecting the presence of PD1 in a biological sample. The term "detecting" as used herein encompasses quantitative or qualitative detection. In certain embodiments, a biological sample comprises a cell or tissue, such as immune cell or T cell infiltrates.

In an aspect, the invention also relates to an in vitro or ex vivo method of diagnosis, in particular a method of diagnostic suitable for use in personalized medicine, more particularly in a companion diagnosis, wherein a humanized anti-PD-1 antibody or an antigen-binding fragment thereof is used for the detection of PD-1 positive cells in a sample, preferably previously obtained from a subject and optionally for the quantification of the expression of PD-1.

The invention further provides methods for detecting the presence of human PD-1 antigen in a sample, or measuring the amount of human PD-1 antigen, comprising contacting the sample, and a control sample, with the humanized anti-PD1 antibody according to the invention, under conditions that allow for formation of a complex between the antibody or portion thereof and human PD-1. The formation of a complex is then detected, wherein a difference complex formation between the sample compared to the control sample is indicative the presence of human PD-1 antigen in the sample. Such method may be an in vitro or in vivo method. The antibody may be an immunoconjugate comprising a suitable detectable moiety as described hereabove. These assays may be useful, for example, evaluating the presence and/or evolution of a disease such as cancer.

In another aspect, the invention also relates to the use, in particular in vitro or ex vivo, of a humanized anti-human PD-1 antibody or antigen-binding fragment thereof of the invention in a method wherein PD-1 is used as a biomarker that is predictive for the response to a treatment in a subject, in particular in a cancer subject.

In an aspect, the invention also relates to an in vitro or ex vivo method of predicting the response of a cancer subject to a treatment, in particular with a humanized anti-human PD-1 antibody or antigen-binding fragment thereof of the invention, comprising:
  determining the expression level of PD-1 in a tumor sample, preferably previously obtained from a subject, preferably with a humanized anti-human PD-1 antibody or antigen-binding fragment thereof of the invention linked to a detectable moiety, and
  comparing the expression level of PD-1 to a value representative of an expression level of PD-1 in a non-responding subject population,
wherein a higher expression level of PD-1 in the tumor sample of the subject is indicative for a subject who will respond to the treatment, preferably the anti-cancer treatment using a humanized anti-PD1 antibody or antigen binding fragment thereof, or a pharmaceutical composition comprising such.

The invention also provides diagnostic methods, wherein a humanized anti-PD1 antibody or fragment thereof is used to select subjects eligible for therapy with a humanized anti-PD1 antibody, e.g. where PD-1 is a biomarker for selection of patients, or where PD-1 is overexpressed.

Kits

Any of the antibody or compositions described herein may be included in a kit provided by the present invention. The present disclosure also provides kits for use in enhancing immune responses and/or treating diseases (e.g. cancer and viral diseases) associated with the PD-1 signaling.

Particularly, a kit according to the invention may comprise:
  an anti-hPD1 antibody or antigen-binding fragment thereof as described herein,
  a nucleic acid molecule or group of nucleic acid molecules encoding said antibody,
  a vector comprising said nucleic acid molecule or group of nucleic acid molecules, and/or
  a cell comprising said vector, nucleic acid molecule or group of nucleic acid molecules.

In the context of the present invention, the term "kit" means two or more components (one of which corresponding to humanized anti-hPD-1 antibody molecule, the nucleic acid molecule, the vector or the cell of the invention) packaged in a container, recipient or otherwise. The kit may thus include, in suitable container means, humanized anti-PD1 antibodies, and/or host cells of the present invention, and/or vectors encoding the nucleic acid molecule or group of nucleic acid molecules of the present invention, and/or the nucleic acid molecule or group of nucleic acid molecules or related reagents of the present invention. A kit can hence be described as a set of products and/or utensils that are sufficient to achieve a certain goal, which can be marketed as a single unit.

In some embodiments, means of taking a sample from an individual and/or of assaying the sample may be provided. In certain embodiments the kit includes cells, buffers, cell media, vectors, primers, restriction enzymes, salts, and so forth. The kits may also comprise means for containing a sterile, pharmaceutically acceptable buffer and/or other diluent. The containers may be unit doses, bulk packages (e.g., multi-dose packages) or sub-unit doses.

In an embodiment, the invention relates to a kit as defined above for a single-dose administration unit. The kit of the invention may also contain a first recipient comprising a dried/lyophilized antibody and a second recipient comprising an aqueous formulation. In certain embodiments of this invention, kits containing single-chambered and multi-chambered pre-filled syringes (e.g., liquid syringes and lyosyringes) are provided.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper penetrable by a hypodermic injection needle). The container may also have a sterile access port (for example the container may be an intravenous solution bag or a vial having a stopper penetrable by a hypodermic injection needle). At least one active agent in the composition is a humanized anti-PD-1 antibody or antigen binding fragment thereof as described herein.

The compositions comprised in the kit according to the invention may also be formulated into a syringe compatible composition. In this case, the container means may itself be a syringe, pipette, and/or other such like apparatus, from which the formulation may be applied to an infected area of the body, and/or even applied to and/or mixed with the other components of the kit. The components of the kit may alternatively be provided as dried powder(s). When reagents and/or components are provided as a dry powder, a soluble composition can be reconstituted by the addition of a suitable solvent. It is envisioned that the solvent may also be provided in another container means and be suitable for administration.

In some embodiments, the kit further includes an additional agent for treating cancer or an infectious disease, and the additional agent may be combined with the humanized anti-PD1 antibody, or other components of the kit of the present invention or may be provided separately in the kit. Particularly, the kits described herein may include one or more additional therapeutic agents such as those described in the "Combined Therapy" described hereabove. The kit(s) may be tailored to a particular cancer for an individual and comprise respective second cancer therapies for the individual as described hereabove.

The instructions related to the use of the antibody molecule or pharmaceutical composition described herein generally include information as to dosage, dosing schedule, route of administration for the intended treatment, means for reconstituting the antibody and/or means for diluting the antibody of the invention. Instructions supplied in the kits of the invention are typically written instructions on a label or package insert (e.g., a paper sheet included in the kit in the form of a leaflet or instruction manual). In some embodiments, the kit can comprise instructions for use in accordance with any of the methods described herein. The included instructions can comprise a description of administration of the pharmaceutical composition comprising the antibody to enhance immune responses and/or to treat a disease as described herein. The kit may further comprise a description of selecting an individual suitable for a treatment based on identifying whether that individual has a disease associated with the PD-1 signaling, e.g., those described herein.

EXAMPLES

The following Figures and Examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Example 1

CDR-Grafting with Human Germlines (Human Framework)

The first step to humanize antibody was to graft mouse anti PD-1 CDR region into human germlines. Three heavy chains human germlines (IGHV7-4-1*02, IGHV1-46*01, IGHV3-20*01) and two germlines for light chain (IGKV2-30*02, IGKV3-11*01) were tested. As shown in Table 1, the germline IGHV7-4-1*02 heavy chain and IGKV2-30*02 have the highest % of humanization, superior to the 85% required to qualify an antibody as humanized.

TABLE 1

T20 humanness score determined using the Cutoff Human Databases. abAnalyzer.lakepharma.com: In general, full-length sequences that score above 85 cutoffs are considered human-like.

| CDR-grafting | IMGT human germline | Variable region % humanization |
|---|---|---|
| Heavy chain | IGHV7-4-1 | 89.8 |
|  | IGHV1-46*01 | 79.6 |
|  | IGHV3-20*01 | 82.7 |
| Light chain | IGKV2-30*02 | 89 |
|  | IGKV3-11*01 | 80 |

Heavy and light chains were transiently co-transfected into adherent COS cells. Concentration of antibody was assessed in the supernatant of COS cells using a sandwich ELISA (immobilized donkey anti human Fc antibody for detection and revelation was assessed using a mouse anti human kappa+a peroxidase conjugated goat anti mouse antibody). Concentration was calculated using a human IvIgG standard (in ng/ml). As shown in Table 2, good productivity in COS cells was obtained for the germline IGHV7-4-1 and IGKV2-30*02 (the combination with the highest % of humanization), whereas the combination with the germline IGHV3-20*01 and IGKV3-11*01 considerably reduce productivity of the humanized anti-PD-1 antibody. In addition, it could be noted that other combinations also show good productivity.

TABLE 2

Concentration of anti-PD1 antibody produced
in the supernatant of COS mammalian cells.

| (ng/ml) | VH chimeric wt | VH IGHV7-4-1 | VH IGHV1-46*01 | VH IGHV3-20*01 |
|---|---|---|---|---|
| VL chimeric wt | 3459.4 | 1377.2 | 1400.9 | 586.7 |
| VL IGKV2-30*02 | 2459.4 | 1959.0 | 2743.2 | 1888.7 |
| VL IGKV3-11*01 | 3166.0 | 1713.4 | 2368.7 | 735.0 |

Binding analysis of humanized anti-PD1 variant antibodies was performed on human PD1 protein by ELISA. Recombinant hPD1 (Sino Biologicals, Beijing, China; reference 10377-H08H) was immobilized on plastic at 0.5 µg/ml in carbonate buffer (pH9.2) and supernatant of COS cells were added at multiple concentration to measure binding efficacy. After incubation and washing, peroxidase-labeled donkey anti-human IgG (Jackson Immunoresearch; USA; reference 709-035-149) was added and revealed by conventional methods.

TABLE 3

ED50 determination refers to the concentration required to reach 50% of the signal in this assay for each humanized anti-PD1 variant antibodies. Unpurified anti PD-1 antibodies produced by COS cells were used for this experiment.

| ED50 (ng/ml) | VH chimeric wt | VH IGHV7-4-1 | VH IGHV1-46*01 | VH IGHV3-20*01 |
|---|---|---|---|---|
| VL chimeric wt | 6.9 | 7.9 | 6.3 | 9.0 |
| VL IGKV2-30*02 | 8.5 | 8.2 | 6.7 | 7.0 |
| VL IGKV3-11*01 | 7.4 | 6.4 | 5.1 | 5.7 |

All CDR-engrafted germlines have similar binding to PD-1 compared to the chimeric antibody (VHwt+VLwt), validating the biological property of the PD-1 antibody (Table 3). Altogether the IGHV7-4-1 framework and VL-CDR with IGKV2-30*02 framework were selected due to (1) their high humanization percentage, 89.8% and 89% respectively (2) higher complementary sequence compared to the original sequence of the antibody, (3) preserved in vitro biological activity and (4) good productivity in mammalian cells.

The second step of humanization consisted of mutating the mouse-derived CDR sequences to increase percentage of humanization and remove deamination or glycosylation sites in the heavy and light chains that can destabilize the antibody in the manufacturing process. Multiple mutated sequences listed in Table 4 have been generated and tested for their production and biological activity. The light chain sequence also presented a glycosylation site in CDR1 ("NG" sequence), which could impair the product stability in the manufacturing process. To remove this glycosylation site, G29 amino acid was substituted into T amino-acid leading to the "LD" chain (amino acid position is determined by Kabat numbering, corresponding to G34 in SEQ ID NO:33). The HCLD antibody is a good candidate but presents a deamination site (DS sequence) in the CDR3 region of the heavy chain. This sequence can impair product stability in the manufacturing process. To remove this DS sequence, the inventors generated alternative sequences HE, HG, HH, HI, HJ, HK, HL, by either substituting D105 or 5106 amino acids.

TABLE 4

Amino acid sequences of the humanized anti-PD1 variants used in the examples below.
Example 2: Binding analysis of humanized anti-PD1 variant antibodies on human PD1 protein by Blitz, ELISA and Flow cytometry.

| Seq ID | Name | Amino acid sequences |
|---|---|---|
| 25 | HC | QIQLVQSGSELKKPGASVKVSCKASGYTFTHYAMNWVRQ APGQGLEWMGWINTNTGEPTYAQGFTGRFVFSLDTSVST AYLQISSLKAEDTAVYYCAREREPGMDSWGQGTLVTVSS ASTKGPSVFPLAPCSRSTSESTAALGCLVKDYFPEPVTV SWNSGALTSGVHTFPAVLQSSGLYSLSSVVTVPSSSLGT KTYTCNVDHKPSNTKVDKRVESKYGPPCPPCPAPEFLGG PSVFLFPPKPKDTLMISRTPEVTCVVVDVSQEDPEVQFN WYVDGVEVHNAKTKPREEQFNSTYRVVSVLTVLHQDWLN GKEYKCKVSNKGLPSSIEKTISKAKGQPREPQVYTLPPS QEEMTKNQVSLTCLVKGFYPSDIAVEWESNGQPENNYKT TPPVLDSDGSFFLYSRLTVDKSRWQEGNVFSCSVMHEAL HNHYTQKSLSLSPGK |
| 26 | HE | QIQLVQSGSELKKPGASVKVSCKASGYTFTHYAMNWVRQ APGQGLEWMGWINTNTGEPTYAQGFTGRFVFSLDTSVST AYLQISSLKAEDTAVYYCAREREPGMDTWGQGTLVTVSS ASTKGPSVFPLAPCSRSTSESTAALGCLVKDYFPEPVTV SWNSGALTSGVHTFPAVLQSSGLYSLSSVVTVPSSSLGT KTYTCNVDHKPSNTKVDKRVESKYGPPCPPCPAPEFLGG PSVFLFPPKPKDTLMISRTPEVTCVVVDVSQEDPEVQFN WYVDGVEVHNAKTKPREEQFNSTYRVVSVLTVLHQDWLN GKEYKCKVSNKGLPSSIEKTISKAKGQPREPQVYTLPPS QEEMTKNQVSLTCLVKGFYPSDIAVEWESNGQPENNYKT TPPVLDSDGSFFLYSRLTVDKSRWQEGNVFSCSVMHEAL HNHYTQKSLSLSPGK |
| 27 | HG | QIQLVQSGSELKKPGASVKVSCKASGYTFTHYAMNWVRQ APGQGLEWMGWINTNTGEPTYAQGFTGRFVFSLDTSVST AYLQISSLKAEDTAVYYCAREREPGMESWGQGTLVTVSS ASTKGPSVFPLAPCSRSTSESTAALGCLVKDYFPEPVTV SWNSGALTSGVHTFPAVLQSSGLYSLSSVVTVPSSSLGT KTYTCNVDHKPSNTKVDKRVESKYGPPCPPCPAPEFLGG PSVFLFPPKPKDTLMISRTPEVTCVVVDVSQEDPEVQFN WYVDGVEVHNAKTKPREEQFNSTYRVVSVLTVLHQDWLN GKEYKCKVSNKGLPSSIEKTISKAKGQPREPQVYTLPPS QEEMTKNQVSLTCLVKGFYPSDIAVEWESNGQPENNYKT TPPVLDSDGSFFLYSRLTVDKSRWQEGNVFSCSVMHEAL HNHYTQKSLSLSPGK |
| 28 | HH | QIQLVQSGSELKKPGASVKVSCKASGYTFTHYAMNWVRQ APGQGLEWMGWINTNTGEPTYAQGFTGRFVFSLDTSVST AYLQISSLKAEDTAVYYCAREREPGMDHWGQGTLVTVSS ASTKGPSVFPLAPCSRSTSESTAALGCLVKDYFPEPVTV SWNSGALTSGVHTFPAVLQSSGLYSLSSVVTVPSSSLGT KTYTCNVDHKPSNTKVDKRVESKYGPPCPPCPAPEFLGG PSVFLFPPKPKDTLMISRTPEVTCVVVDVSQEDPEVQFN WYVDGVEVHNAKTKPREEQFNSTYRVVSVLTVLHQDWLN GKEYKCKVSNKGLPSSIEKTISKAKGQPREPQVYTLPPS QEEMTKNQVSLTCLVKGFYPSDIAVEWESNGQPENNYKT TPPVLDSDGSFFLYSRLTVDKSRWQEGNVFSCSVMHEAL HNHYTQKSLSLSPGK |
| 29 | HI | QIQLVQSGSELKKPGASVKVSCKASGYTFTHYAMNWVRQ APGQGLEWMGWINTNTGEPTYAQGFTGRFVFSLDTSVST AYLQISSLKAEDTAVYYCAREREPGMDAWGQGTLVTVSS ASTKGPSVFPLAPCSRSTSESTAALGCLVKDYFPEPVTV SWNSGALTSGVHTFPAVLQSSGLYSLSSVVTVPSSSLGT KTYTCNVDHKPSNTKVDKRVESKYGPPCPPCPAPEFLGG PSVFLFPPKPKDTLMISRTPEVTCVVVDVSQEDPEVQFN WYVDGVEVHNAKTKPREEQFNSTYRVVSVLTVLHQDWLN GKEYKCKVSNKGLPSSIEKTISKAKGQPREPQVYTLPPS QEEMTKNQVSLTCLVKGFYPSDIAVEWESNGQPENNYKT TPPVLDSDGSFFLYSRLTVDKSRWQEGNVFSCSVMHEAL HNHYTQKSLSLSPGK |
| 30 | HJ | QIQLVQSGSELKKPGASVKVSCKASGYTFTHYAMNWVRQ APGQGLEWMGWINTNTGEPTYAQGFTGRFVFSLDTSVST AYLQISSLKAEDTAVYYCAREREPGMDYWGQGTLVTVSS ASTKGPSVFPLAPCSRSTSESTAALGCLVKDYFPEPVTV SWNSGALTSGVHTFPAVLQSSGLYSLSSVVTVPSSSLGT KTYTCNVDHKPSNTKVDKRVESKYGPPCPPCPAPEFLGG |

TABLE 4-continued

Amino acid sequences of the humanized anti-PD1
variants used in the examples below.
Example 2: Binding analysis of humanized anti-
PD1 variant antibodies on human PD1 protein by
Blitz, ELISA and Flow cytometry.

| Seq ID | Name | Amino acid sequences |
|---|---|---|
|  |  | PSVFLFPPKPKDTLMISRTPEVTCVVVDVSQEDPEVQFN WYVDGVEVHNAKTKPREEQFNSTYRVVSVLTVLHQDWLN GKEYKCKVSNKGLPSSIEKTISKAKGQPREPQVYTLPPS QEEMTKNQVSLTCLVKGFYPSDIAVEWESNGQPENNYKT TPPVLDSDGSFFLYSRLTVDKSRWQEGNVFSCSVMHEAL HNHYTQKSLSLSPGK |
| 31 | HK | QIQLVQSGSELKKPGASVKVSCKASGYTFTHYAMNWVRQ APGQGLEWMGWINTNTGEPTYAQGFTGRFVFSLDTSVST AYLQISSLKAEDTAVYYCAREREPGMDNWGQGTLVTVSS ASTKGPSVFPLAPCSRSTSESTAALG<u>C</u>LVKDYFPEPVTV SWNSGALTSGVHTFPAVLQSSGLYSLSSVVTVPSSSLGT KTYTCNVDHKPSNTKVDKRVESKYGPPCPPCPAPEFLGG PSVFLFPPKPKDTLMISRTPEVTCVVVDVSQEDPEVQFN WYVDGVEVHNAKTKPREEQFNSTYRVVSVLTVLHQDWLN GKEYKCKVSNKGLPSSIEKTISKAKGQPREPQVYTLPPS QEEMTKNQVSLTCLVKGFYPSDIAVEWESNGQPENNYKT TPPVLDSDGSFFLYSRLTVDKSRWQEGNVFSCSVMHEAL HNHYTQKSLSLSPGK |
| 32 | HL | QIQLVQSGSELKKPGASVKVSCKASGYTFTHYAMNWVRQ APGQGLEWMGWINTNTGEPTYAQGFTGRFVFSLDTSVST AYLQISSLKAEDTAVYYCAREREPGMDEWGQGTLVTVSS ASTKGPSVFPLAPCSRSTSESTAALG<u>C</u>LVKDYFPEPVTV SWNSGALTSGVHTFPAVLQSSGLYSLSSVVTVPSSSLGT KTYTCNVDHKPSNTKVDKRVESKYGPPCPPCPAPEFLGG PSVFLFPPKPKDTLMISRTPEVTCVVVDVSQEDPEVQFN WYVDGVEVHNAKTKPREEQFNSTYRVVSVLTVLHQDWLN GKEYKCKVSNKGLPSSIEKTISKAKGQPREPQVYTLPPS QEEMTKNQVSLTCLVKGFYPSDIAVEWESNGQPENNYKT TPPVLDSDGSFFLYSRLTVDKSRWQEGNVFSCSVMHEAL HNHYTQKSLSLSPGK |
| 33 | LC | DVVMTQSPLSLPVTLGQPASISCRSSQSLVHANGNTYLE WYQQRPGQSPRLLIYKVSNRFSGVPDRFSGSG<u>S</u>GTDFTL KISRVEAEDVGVYYCFQGTHVPNTFGQGTKLEIKRTVAA PSVFIFPPSDEQLKSGTASVVCLLNNFYPREAKVQWKVD NALQSGNSQESVTEQDSKDSTYSLSSTLTLSKADYEKHK VYACEVTHQGLSSPVTKSFNRGEC |
| 34 | LD | DVVMTQSPLSLPVTLGQPASISCRSSQSLVHANTNTYLE WYQQRPGQSPRLLIYKVSNRFSGVPDRFSGSG<u>S</u>GTDFTL KISRVEAEDVGVYYCFQGTHVPNTFGQGTKLEIKRTVAA PSVFIFPPSDEQLKSGTASVVCLLNNFYPREAKVQWKVD NALQSGNSQESVTEQDSKDSTYSLSSTLTLSKADYEKHK VYACEVTHQGLSSPVTKSFNRGEC |

Recombinant hPD1 (Sino Biologicals, Beijing, China; reference 10377-H08H) was immobilized on plastic at 0.5 µg/ml in carbonate buffer (pH9.2) and purified antibody was added to measure binding. After incubation and washing, peroxidase-labeled donkey anti-human IgG (Jackson Immunoresearch; USA; reference 709-035-149) was added and revealed by conventional methods.

TABLE 5

ED50 determination from FIG. 1A refers to the concentration required to reach 50% of the signal in this assay for each humanized anti-PD1 variant antibodies. Purified anti PD-1 antibodies produced by HEK cells were used for this experiment.

|  | ED50 ng/ml |
|---|---|
| Chimeric | 16.79 |
| HCLD | 12.66 |
| HELD | 19.23 |
| HGLD | 14.75 |
| HHLD | 16.39 |
| HILD | 11.55 |
| HJLD | 13.44 |
| HKLD | 11.42 |
| HLLD | 16.58 |

TABLE 6

Avidity analysis of anti-PD1 antibodies to human PD1 recombinant protein measured by Blitz.

|  | KD (nM) | Ka (1/Ms) | Kd (1/s) |
|---|---|---|---|
| Chimeric | 1.29 | 2.26e5 | 2.91e−4 |
| HCLD | 1.34 | 3.19e5 | 4.29e−4 |
| HELD | 1.14 | 4.43e5 | 5.07e−4 |
| HGLD | 1.28 | 2.74e5 | 3.52e−4 |
| HHLD | 0.84 | 4.05e5 | 3.43e−4 |
| HILD | 0.93 | 4.58e5 | 4.27e−4 |
| HJLD | 1.05 | 4.1e5 | 4.32e−4 |
| HKLD | 0.75 | 3.51e5 | 2.62e−4 |
| HLLD | 1.25 | 4.41e5 | 5.54e−4 |

TABLE 7

Affinity analysis of anti-PD1 antibodies to human PD1 recombinant protein measured by Biacore.

| Ab | KD (M) | Ka (1/Ms) | Kd (1/s) |
|---|---|---|---|
| Chimeric | $1.01^{E}{-}9$ | $2.43^{E}5$ | 2.45E−4 |
| HKLD | $4.1^{E}{-}9$ | $3.24^{E}5$ | 0.05137 |
| KEYTRUDA clinic | $4.42^{e}{-}9$ | $4.5^{e}5$ | 0.00428 |

TABLE 8

ED50 determination from FIG. 1C refers to the concentration required to reach 50% of the signal in this assay for each humanized anti-PD1 variant antibodies.

|  | pM |
|---|---|
| HGLD | 1543.68523 |
| HHLD | 133.273506 |
| HILD | 118.262072 |
| HJLD | 241.404054 |
| HKLD | 187.312713 |
| HLLD | 223.473437 |
| HELD | 401.699408 |
| HCLD | 278.261503 |
| Chimeric | 611.914193 |

TABLE 9

T20 Percentage of humanness determined using the Cutoff Human Databases: abAnalyzer.lakepharma.com: In general, full-length sequences that score above 85 are considered human-like antibody.

| Name | Seq ID | T20 |
|---|---|---|
| VH_Consensus | 17 | 90.86 |
| HC | 18 | 91.28 |
| HE | 19 | 91.06 |

TABLE 9-continued

T20 Percentage of humanness determined using the
Cutoff Human Databases: abAnalyzer.lakepharma.com:
In general, full-length sequences that score above
85 are considered human-like antibody.

| Name | Seq ID | T20 |
|---|---|---|
| HG | 20 | 90.3 |
| HH | 21 | 90.94 |
| HI | 22 | 91.06 |
| HJ | 23 | 91.2 |
| HK | 24 | 91.07 |
| HL | 25 | 91.28 |
| VL_consensus | 26 | 89.5 |
| LC | 27 | 89.55 |
| LD | 28 | 88.7 |

TABLE 10

T20 Percentage of humanness determined using the Cutoff Human
Databases: abAnalyzer.lakepharma.com: In general, full-
length sequences that score above 85 are considered human-like.

| score T20 | VH | VL |
|---|---|---|
| Keytruda | 75.7 | 82.7 |
| HKLD | 91.07 | 88.7 |

Figure 2:
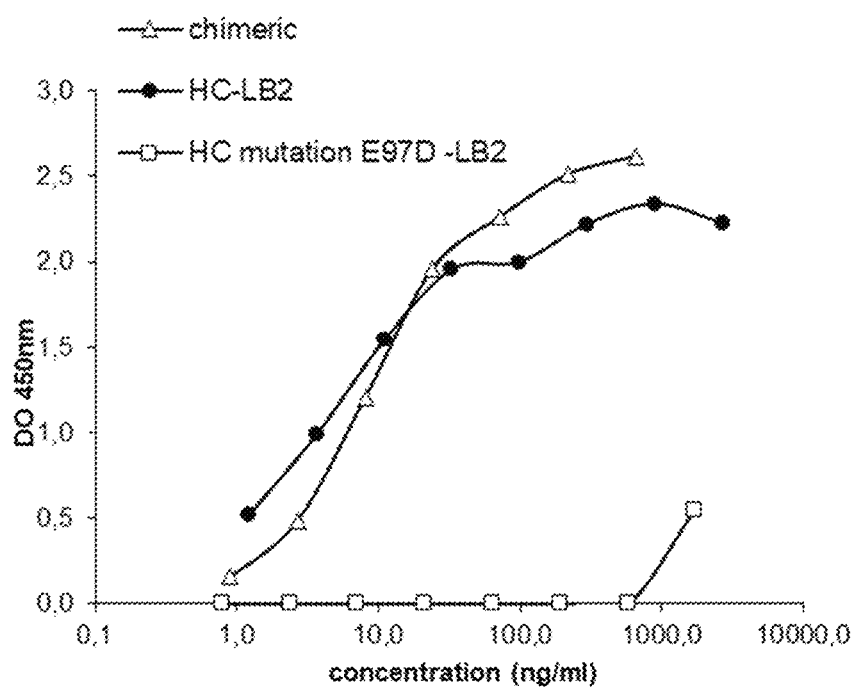
FIG. 2: Binding loss of some humanized anti-PD1 antibodies to human PD1 after mutation of amino acids during humanization process: ELISA binding of the humanized anti-PD1 variants after mutations on the heavy variable chain at Kabat position 97 (i.e. conventional amino acid position 101).
Figure 2:
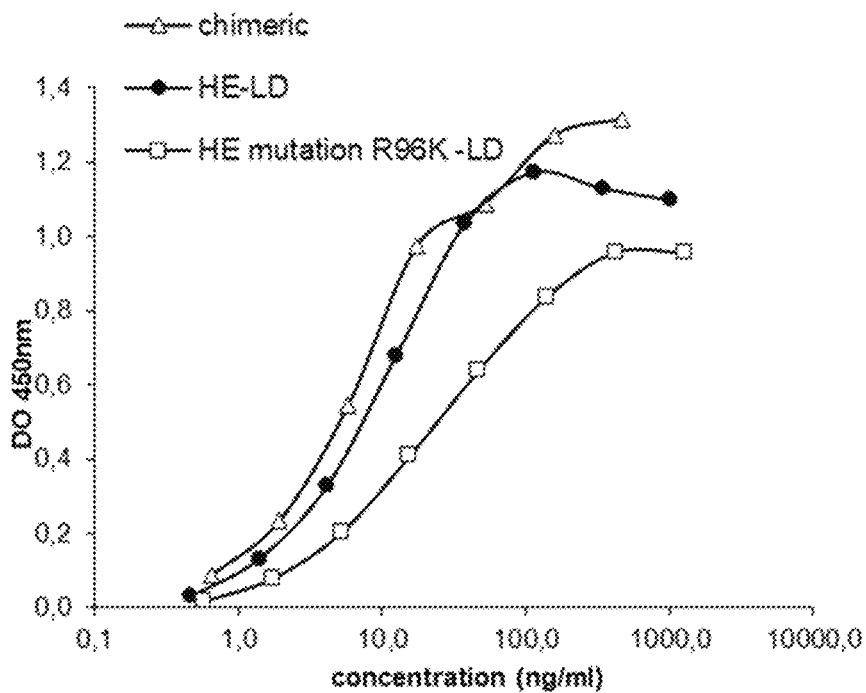
Figure 2:
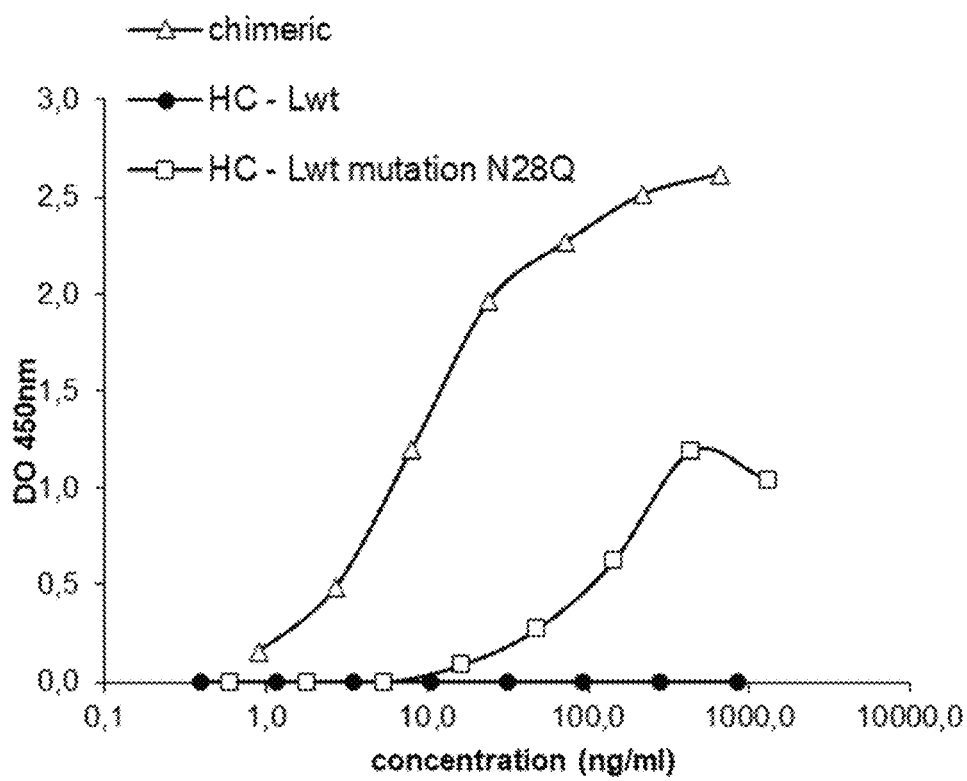
Figure 2:
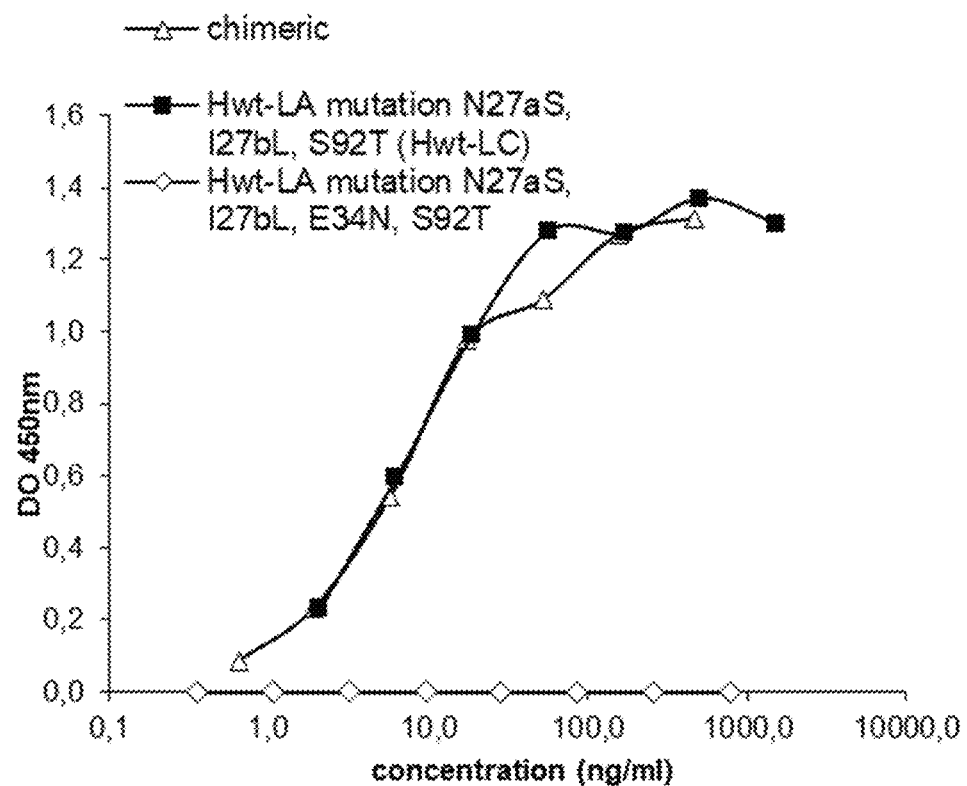
Figure 2:
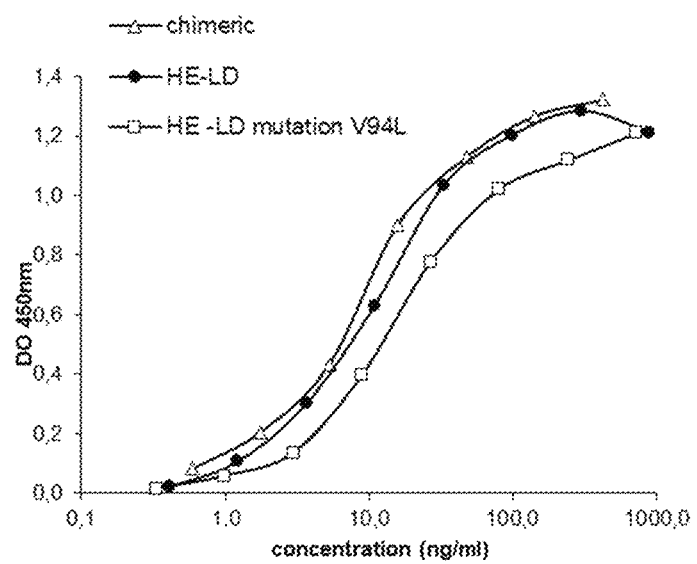

Results: Following the humanization stages of the mouse anti-humanPD1 antibody (as referred herein as the chimeric antibody), several humanized anti-PD1 variant antibodies were selected for their good binding capacity to human PD1 (recombinant protein as well as cell surface expressed PD1) compared to the chimeric antibody. FIG. 1 (A) and Table 5 show by different methods that the antibody HKLD has the best binding activity among the variant antibodies and an improved binding compared to the chimeric antibody. FIG. 1B confirms this similar binding capacity on human cells when the antibody is combined with the LC light chain variant. The avidity measurement presented Table 6 indicates that HKLD presents the best KD among the variant antibodies and an improved KD compared to the chimeric antibody. Table 7 compares the affinity measurements to PD1 of chimeric, HKLD and other PD1 antibody like Keytruda, a clinically approved anti-PD-1 antibody, and shows that the variant HKLD has a similar affinity compared to Keytruda. In this experiment, affinity of antibodies was measured by immobilizing an anti-Fc antibody, allowing affinity measurement of one valence of the PD-1 antibody, in contrast to Blitz experiment that used immobilized PD-1 and soluble antibodies. Although the affinity of the anti PD-1 variant antibody depicted similar affinity/avidity for PD-1 protein, in a cell-based system, the inventors surprisingly observed that HKLD binds better PD-1+ T cells compared to chimeric form of the antibody, as shown FIG. 1 C and Table 8. On the other hand, the HGLD variant loses binding capacity compared to the anti PD-1 chimeric form. In addition to HGLD, the inventors also showed that, during the humanization process, some mutations induced the loss of PD1 binding capacity. FIG. 2 (from A to E) shows that amino acids numbered by the Kabat method 96 and 97 on the Heavy variable domain and the amino acids Kabat numbered 28, 34, 94 on the Light variable domain are crucial for PD1 binding capacity and should therefore not be mutated. Table 9 presents the degree of the humanization (T20 humanness score) for each selected variable domains of the Heavy and Light chains. T20 determination indicates a very strong humanness score for each variable region of the selected variant antibodies, in particular from 88 to 91.28%. Table 10 shows that the T20 score of the humanized anti PD-1 (HKLD variant) was superior to the standard Keytruda, previously described and clinically approved anti PD-1 sequence (heavy chain 75.7 vs 91.07% and light chain 82.7 vs 88.7%).

Example 3

Antibody Productivity After Transient Transfection in Mammalian COS and CHO Cells Heavy and light chains were transiently co-transfected into adherent COS cells or CHO cells. Concentration of antibody was assessed in the supernatant of COS and CHO cells using a sandwich ELISA (immobilized donkey anti human Fc antibody for detection and revelation with a mouse anti human kappa+a peroxidase conjugated goat anti mouse antibody). Concentration was determined with human IvIgG standard. Productivity was calculated as the quantity of purified antibody per liter of collected culture supernatant.

TABLE 11

High productivity yield when produced in mammalian cells
(COS and CHO). Higher productivity of humanized form
of the antibody compared to the chimeric antibody.

| | Production CHO (mg/L) | Production COS (mg/L) |
|---|---|---|
| Chimeric | 4.6 | 1.67 |
| HCLD | 9.58 | 7.21 |
| HELD | 11.71 | 4.03 |
| HGLD | 12.15 | 6.91 |
| HHLD | 12.80 | 4.48 |
| HILD | 11.41 | 5.81 |
| HJLD | 12.67 | 5.80 |
| HKLD | 14.08 | 6.35 |
| HLLD | 14.35 | 4.85 |

TABLE 12

Stability of anti PD-1 antibody after incubation 37°
C. during 7 days. Antibodies were incubated during 7 days
at 4° C. or 37° C. From Exclusion diffusion chromatography
the percentage of the monomeric form and aggregates were
assessed. Day 0 is used as positive control in these experiments.

| | Day 0 | | Day 7 after incubation at 37° C. | |
|---|---|---|---|---|
| | % monomeric form | % aggregates | % monomeric form | % aggregates |
| HCLC | 94.8 | 2.5 | 96.1 | 1.1 |
| HCLD | 91.4 | 6.6 | 90.5 | 7 |
| HELC | 98.7 | 1.3 | 98.8 | 1.2 |
| HELD | 97.2 | 2.1 | 96.4 | 2.4 |
| HGLD | 97.45 | 2.55 | 96.57 | 3.43 |
| HHLD | 97.32 | 2.68 | 97.82 | 2.18 |
| HILD | 96.16 | 3.84 | 96.14 | 3.86 |
| HJLD | 97.74 | 2.26 | 98.28 | 1.72 |
| HKLD | 96.9 | 3.1 | 97.12 | 2.88 |
| HLLD | 96.98 | 3.02 | 96.73 | 3.27 |

Results: The different variants were produced in mammalian cells such as CHO or COS and the results presented in table 11 show in a surprising manner that the humanized anti-PD1 variant antibodies have a better productive yield (mg/L) than the chimeric antibody in both cell types. The HKLD presents the best productive yield. In CHO cells, productive yield for this antibody is increased by 3-fold and almost 4-fold in COS cells. In parallel, stability of the molecule was evaluated in vitro, as shown in Table 12, all variants present a good stability at 4° C. and 37° C. with low aggregation. Those results indicate that the humanized anti-PD1 antibody of the invention presents a very good manufacturability which is very important for the next steps of the clinical development and therapeutic applications.

In a second experiment using CHO cells production method, the productivity of HKLD variant was compared to the productivity of Keytruda and chimeric anti PD-1 antibodies. As shown in the FIG. 6, the inventors observed increased productivity with HKLD variant compared to chimeric and Keytruda backbones. In this test, productivity was tested in small scale (12-well plate, transient transfection on adherent cells) and in bioreactor (unoptimized fed-batch CHO cell production). A high yield of 2 g/L for HKLD variant was obtained, confirming the high productivity of the antibody in large scale production process.

Example 4

Competitive Assays to Measure the Antagonist Activity of the Humanized Anti-PD1 Variant Antibodies on the PD-PDL1 and PD1-PDL2 Interactions:

TABLE 13

Blitz determination of the inhibition of the interaction of PD1-PDL1 in presence of the different humanized anti-PD1 variant antibodies: ka (1/Ms), kd (1/s) and KD (nM) were measured.

|  | KD (nM) | Ka (1/Ms) | Kd (1/s) |
| --- | --- | --- | --- |
| No antibody | 1.83e−7 | 3.68E4 | 6.71E−3 |
| HCLD | 7.15E−3 | 10.1 | 7.2E−2 |
| HELD | 5.91E−3 | 14.9 | 1.04E4 |
| HGLD | 9.8E−3 | 28.3 | 5.34E−2 |
| HHLD | 8.54E−3 | 112.2 | 1.04E−1 |
| HILD | 1.12E−3 | 790 | 88.8E−1 |
| HJLD | 2.79E−3 | 65.4 | 5.67E4 |
| HKLD | 4.59E−3 | 18.8 | 8.62E−2 |
| HLLD | 2.15E−3 | 99.6 | 2.14E−1 |

TABLE 14

Antagonist capacity of PD-1 antibodies to block PD-L1 Binding. Determination of the IC50 (ng/ml) obtained with the different humanized anti-PD1 variant antibodies issued from FIG. 4C.

|  | IC50 ng/mL |
| --- | --- |
| Chimeric | 253.15 |
| HCLD | 196.11 |
| HELD | 196.43 |
| HGLD | 177.57 |
| HHLD | 201.4 |
| HILD | 175.4 |
| HJLD | 193.95 |
| HKLD | 205.32 |
| HLLD | 155.72 |

PD-1 Signaling Analysis Using DiscoverX Cell-Based Bioassay

The capacity of anti-PD-1 antibodies to blocks PD-1/pSHP-1 signaling was assessed with DiscoverX PathHunter® Jurkat PD-1 (SHP1) Signaling Assay (reference 93-1104C19). In this assay, Jurkat T cells stably express a chimeric PD-1 receptor fused to Beta-gal fragment (ED) and an engineered SHP1 fused to complementing Beta-gal fragment (EA). The coculture of Jurkat cells with PD-L1 presenting cells results in PD-1 phosphorylation, recruitment of engineered SHP-1 and the complementation of the ED and EA fragment creating an active Beta-gal enzyme and bioluminescence signal after substrate addition. Chemiluminescence is proportional to PD-1 signaling activation. Experiment was performed as per manufacturer recommendation. Briefly, PD-1+ Jurkat cells were incubated with different concentration of anti PD-1 antibodies for 1 hour then cocultured with PD-L1+ cells for another hour. Detection reagent was added luminescence signal was read 180 minutes after using Tecan™ plate reader. The humanized anti-PD1 variant antibodies were tested at different concentrations. Data are represented in RLU (Relative luminescence signal). IC50 (ng/mL) refers to the concentration required to reach 50% of signal inhibition.

TABLE 15

Antagonist capacity of PD-1 antibodies to block PD-1 mediated inhibitory signaling: Determination of the IC50 (ng/mL) which refers to the concentration required to reach 50% of signal inhibition from FIG. 7A.

|  | IC50 ng/mL |
| --- | --- |
| Chimeric | 16.79 |
| HCLD | 12.66 |
| HELD | 19.23 |
| HGLD | 14.75 |
| HHLD | 16.92 |
| HILD | 11.55 |
| HJLD | 13.44 |
| HKLD | 11.42 |
| HLLD | 16.58 |

Example 5

Cell Activation Assay Using Promega Cell-Based Bioassay

The capacity of anti-PD-1 antibodies restore T cell activation was tested using Promega PD-1/PD-L1 kit (Reference J1250). Two cell lines are used (1) Effector T cells (Jurkat stably expressing PD-1, NFAT-induced luciferase) and (2) activating target cells (CHO K1 cells stably expressing PDL1 and surface protein designed to stimulate cognate TCRs in an antigen-independent manner. When cells are cocultured, PD-L1 /PD-1 interaction inhibits TCR mediated activation thereby blocking NFAT activation and luciferase activity. The addition of an anti- PD-1 antibody blocks the PD-1 mediated inhibitory signal leading to NFAT activation and luciferase synthesis and emission of bioluminescence signal. Experiment was performed as per as manufacturer recommendations. Serial dilutions of the PD-1 antibody were tested. Four hours following coculture of PD-L1+target cells, PD-1 effector cells and anti PD-1 antibodies, Bio-Glo™ luciferin substrate was added to the wells and plates were read using Tecan™ luminometer. The quantified Luminescence using a luminometer reflects T cell activation. Serial dilution of the humanized anti-PD1 variant antibodies were tested. ED50 (ug/mL) refers to the concentration of antibody required to reach 50% of maximum luminescence.

TABLE 16 anti-PD-1 antibody potentiates activation of T cells in vitro: Determination of the ED50 (µg/mL) which refers to the concentration of antibody required to reach 50% of maximum luminescence from FIG. 8.

|  | ED50 ug/mL |
| --- | --- |
| Chimeric | 0.29 |
| HCLD | 0.41 |
| HELD | 0.46 |
| HGLD | 1.16 |
| HHLD | 0.54 |
| HILD | 0.40 |
| HJLD | 0.90 |
| HKLD | 0.69 |
| HLLD | 0.89 |

Results: After measurement of the binding capacity of the different humanized anti-PD1 variant antibodies to PD1, the inhibitory capacity of each variant antibodies to block PD1-PDL1 interaction was assessed using different methods (Biacore, Blitz and ELISA). FIG. 4A presents the inhibitory response of the variants: HCLC, HCLD and HELC, HELD antibodies compared to the chimeric antibody on PD1-PDL1 interaction. FIG. 4B presents the inhibitory response of the variants HCLD, HELD, HGLD, HILD, HJLD, HKLD and HLLD antibodies on the PDL1 binding to PD1. Table 13 shows that the presence of all variant antibodies inhibits the binding of PDL1 to PD1. Results obtained with HCLC and HELC are similar to those presented table 13 (data not shown). FIG. 4C shows the competitive efficiency of humanized anti-PD1 antibodies at different concentrations leading to determination of the IC50 for each variant (FIG. 4C and table 14). PD1 are able to bind to another ligand expressed on cell surface: PDL2. FIG. 5A and B show that anti PD-1 variant antibodies HELC, HELD and HKLD also block the interaction PD1-PDL2, as measured by Biacore assay and antagonist PD-L2/PD-1 ELISA.

In order to confirm those results, a bioassay assessing the phosphorylation of SHP1, a signaling protein from PD-1 pathway was performed. FIG. 7A and B, presents the inhibitory dose-response obtained with the different humanized anti-PD1 variant antibodies on the phosphorylation of SHP1. Table 15 present the IC50 for each variant antibody showing a similar inhibitory efficiency for all variants on PD1 activation. Nevertheless, two variants named HCLD and HKLD variants were more effective to inhibit the signal P-SHP1 compared to HELD variant for example. Inhibition curves showed a better inhibition with HCLD and HKLD close to the chimeric backbone, whereas the HLLD or HJLD humanized variant loss some antagonist capacity. In parallel, T cell activation was assessed using a NFAT biolumines cence bioassay to compare the inhibitory efficiency of all selected humanized anti-PD1 variant antibodies to inhibit PD1-PDL1 interaction leading to the T cell activation (inhi bition of the inhibitory checkpoint interaction). FIG. 8 shows that all variant tested were able to activate TCR mediated NFAT signaling but with different potency and efficacy. The maximum RLU signal obtained at the plateau phase reflects the potency. The inventor observed that HCLD, HKLD variants have better potency compared to the HELD or HLLD variants for example. This efficacy is determined by the EC50 (Table 16). The chimeric antibody and all variants are effective to activate NFAT and the HCLD, HILD, HKLD, HHLD, HELD and HKLD variants were the most effective to activate T cell.

Example 6

IFNg Secretion by Human T Cells

In order to demonstrate efficacy of HKLD variant to stimulate secretion of effector cytokine by human T cells, the inventors performed a mixed leucocyte reaction assay by co-cultivating Dendritic cells and allogeneic T cells. As shown on FIG. 9, the HKLD variant increases secretion of IFNg cytokine in a dose dependent manner.

All selected humanized anti-PD1 variant antibodies were able to inhibit the binding of PD1 to PDL1 and PDL2 in a manner at least as good as the chimeric antibody. All variants are able to activate T cells. In biological assays, like P-SHP1 inhibition or NFAT activation via PD1 signaling, the inventors observed that three variants were more effec tive than the others, namely HCLD, HKLD and HILD. They exhibit a signal similar to chimeric results and improved PD1 blockade compared to the other variants. In comparison to the other variants, HILD and HKLD variants demon strated the best properties with a high manufacturability and production yield in mammalian cell-based production sys tems while preserving its biological activity:high affinity for PD-1, antagonist capacity for PD-L1 and PD-L2 and capac ity to restore T cell activation (inhibition for pSH-P-1, activation NFAT, promoting IFNg effector cytokine secre tion).

Example 7

In Vivo Efficacy of a Humanized Anti-PD1 Antibody

Efficacy of human anti PD-1 antibody was assessed in multiple in vivo models in immunocompetent mice geneti cally modified to express human PD-1 (exon 2). For meso thelioma model, AK7 mesothelial cells were intrapleurally injected (3e6 cell/mouse) then treated at Day 5/8/12/15 with an anti PD-1 control or anti-PD1 humanized antibody (HKLD variant) at 1 mg/kg. Injected AK7 cells stably express luciferase allowing generation of in vivo biolumi nescence signal following intraperitoneal injection of D-lu ciferin (3 µg/mouse, GoldBio, Saint Louis Mo., USA, Ref erence 115144-35-9). Ten minutes following luciferin injection, bioluminescence signal was measured by Bio space Imager on the dorsal side and ventral side of the mouse for 1 minute. Data were analyzed in photon per second per cm2 per steradian and represent the mean of the dorsal and ventral signal. Each group represents mean +/−SEM of 5 to 7 mice per group. For the MC38 model, MC38 colon cancer cells were subcutaneously injected with 5e5 cells in the flank and Tumor volume was calculated with the formula 0.52×(length×width). Mice were treated when the tumor reached 40-80mm$^3$ with 10 mg/kg of anti-PD1 humanized antibody (HKLD variant) 3 times a week for 3 weeks. For the Hepatocarcinoma orthotopic model, 2.5e6 Hepa1.6 cells are injected into the portal vein Mice were treated with 3mg/kg of IgG4 isotype control or anti-PD1 humanized antibody (HKLD variant) on Day 4/7/11/14/18/21 following tumor injection.

Results: FIG. 10 shows the mesothelioma tumor growth following a treatment with a control anti-PD1 antibody as a positive control or with one of the humanized anti-PD1 variant antibody (HKLD), the negative control is shown by treating animal with PBS. The humanized anti-PD1 of the invention shows a very good efficiency in controlling tumor growth. Humanized anti-PD1 variant antibody (HKLD) can eradicate AK7 mesothelioma tumor as depicted on FIG. 10A with 77% (10 out 13 mice) or 100% (7 mice) of complete response, with respectively 1 or 3 mg/kg of antibody (FIG. 10 B). In vivo efficacy was confirmed in 2 other mouse models. In the ectopic MC38 colon carcinoma, humanized anti-PD1 variant antibody (HKLD) significantly improved median survival and promoted 50% of complete response (5 out of 10 mice) (FIG. 11A and B). Similarly, in the orthotopic HCC model, humanized anti-PD1 variant antibody (HKLD) improved mice survival with 42% of complete response (3 out of 10 mice) (FIG. 12).

Example 8

Pharmacokinetics and Pharmacodynamics of the Humanized anti-PD1 Antibody In Vivo Pharmacokinetics and Pharmacodynamics of the product were assessed in cynomolgus monkeys and mice following a single injection. To assess Pharmacokinetics in mice, BalbcRJ (female 6-9 weeks) were intra-orbitally or subcutaneously injected with a single dose (5 mg/kg) of the chimeric form, the humanized anti PD-1 antibody (HKLD variant) or the Keytruda antibody. Plasma drug concentration was determined by ELISA using an immobilized anti-human light chain antibody (clone NaM76-5F3) diluted serum-containing anti-PD-1 antibody was added. Detection was performed with a peroxidase-labeled donkey anti-human IgG (Jackson Immunoresearch; USA; reference 709-035-149) was added and revealed by conventional methods. Cynomolgus monkeys were intravenously injected with the humanized anti-PD1 antibody (HKLD variant) with 1 or 5mg/kg. Whole blood and sera were collected at multiple time points to or quantify anti-PD1 antibody in the sera by ELISA. anti-PD-1 antibody in the sera of monkeys, PD-1 recombinant protein was immobilized and diluted serum-containing anti-PD-1 antibody was added. Detection was performed with a sulfo-tagged anti human kappa antibody and revealed using MSD technology.

Results: FIGS. 13A, B and C show that the humanized anti PD-1 antibody has a favorable pharmacokinetic profile in vivo in mice and monkeys with a linear kinetic curve. In mice, anti-PD-1 humanized form (HKLD) with IgG1 N298A and IgG4 S228P isotype have a similar profile to Keytruda, clinically used and commercialized anti PD-1 antibody. In cynomolgus monkeys, a good correlation dose vs exposure is observed as higher quantity in the sera of humanized anti PD-1 antibody is detected at 5 mg/kg compared to 1 mg/kg. Altogether this data show that the humanized anti PD-1 has a favorable pharmacokinetic profile in vivo.

Example 9

Humanized Anti PD-1 Antibodies Potentiate Macrophage-Mediated Tumor Cell Phagocytosis Through the Blockage of PD-1/PD-L1 Interaction on the Same Cell PD-1 expression is not limited to T cells, for example, PD-1 can also be expressed on tumor-associated macrophages. PD-L1 expression on tumor cells can trigger a trans-inhibitory signal into macrophages blocking their phagocytic potency (Gordon et al., Nature. 2017 May 25; 545 (7655):495-499). However, it is not described if PD-1/PD-L1 blockade therapy can enhance phagocytosis of PD-L1 negative tumor cells. As M1 macrophages express both receptor on their surface, it is possible that PD-1 and PD-L1 bind on the same cell and trigger a negative regulatory signaling into macrophages. Here, the inventors demonstrated that the humanized anti-PD-1 antibody can restore phagocytic function of macrophages against PD-L1 negative tumor cells through the blockage of PD-1/PD-L1 interaction on the same cell.

Results: FIG. 14A shows the expression of PD-1 and PD-L1 on MO, M1 macrophages and raji cells. Only M1 macrophages express both receptors PD-1 and PD-L1 and MO macrophages express PD-1 high and does not express PD-L1, Raji cells does not express PD-L1. FIG. 14 B shows that the humanized anti-PD-1 antibody surprisingly enhances phagocytosis of PD-L1 negative tumors by M1-macrophages. In comparison to other anti-PD-1 antibodies (pembrolizumab and nivolumab), the humanized anti-PD-1 antibody is even more efficacious in promoting phagocytosis of tumor cells (FIG. 14 C). As tumor cells do not express PD-L1 in this assay and M1 macrophages express both receptors PD1 and PDL1, this experiment suggests that anti-humanized antibody can block the interaction (interaction causing inhibition of tumor cell phagocytosis) between PD-L1 and PD-1 on the same cell. In fact, the same experiment was performed with MO macrophage that do not express PD-1 but express PD-1 receptor (FIG. 14A). As shown on FIG. 14 D, the anti PD-1 humanized antibody enhances phagocytosis of M1 macrophages whereas it has no effect on MO macrophage demonstrating that both receptors, PD-1/PD-L1, are required for the enhanced effect mediated by the humanized anti PD1 antibody. These data suggest that the anti PD-1 humanized antibody neutralizes the PD-1/PD-L1 interaction on the M1 macrophages leading to reactivation tumor cells phagocytosis.

Raji cells do not neither expressed PD-L2 the other ligand of PD-1, as described elsewhere (Andorsky et al, 2011, DOI: 10.1158/1078-0432), supporting that the anti-humanized anti PD-1 antibody can enhance phagocytosis of PD-L1 as well as PD-L2 negative tumor cells.

Although it is well established that PD-1-PD-L1 blockade reactivate T cells, here, the inventors show a new property of anti-PD-1 antibody through direct reinvigoration of macrophages. They demonstrated that the humanized anti-PD-1 antibody can block the interaction of PD-1/PD-L1 on the same macrophages promoting phagocytosis of PD-L1 negative tumor cells. This aspect has a particular interest in clinic since patients expressing PD-L1 on the surface of the tumor cells are treated with PD-1/PD-L1 therapy. The data presented here show that even PD-L1 negative tumors can benefit from humanized anti-PD-1 antibody by reactivation macrophages phagocytosis.

Material and Methods
ELISA Binding PD1

For activity ELISA assay, recombinant hPD1 (Sino Biologicals, Beijing, China; reference 10377-H08H) was immobilized on plastic at 0.5 µg/ml in carbonate buffer (pH9.2) and purified antibody was added to measure binding. After incubation and washing, peroxidase-labeled donkey anti-human IgG (Jackson Immunoresearch; USA; reference 709-035-149) was added and revealed by conventional methods.
PD1 Binding Assay on Human Stimulated T Cells by Cytofluorometry PBMC from healthy volunteers were activated by anti-CD3/CD28 stimulation to stimulate T cells. To measure binding of anti-PD1 on human stimulated T cells, antibody was incubated for 30 min at 4° C., and washed before stained 30 min at 4° C. with PE-labelled anti-human IgG Fc (Biolegend; USA; reference 409303). Samples were analyzed on BD LSRII or Canto II cytofluorometer in gating on CD3 cells (T cells).

Avidity Measurement for PD1 by Blitz Mmethod

The binding affinity/avidity was measured using Blitz method (Forte Bio; USA; reference C22-2 No 61010-1). Recombinant hPD1-His (Sino Biologicals, Beijing, China; reference 10377-H08H) was immobilized at 10µg/ml by histidine tail into a Ni-NTA biosensor (Forte Bio; USA; reference 18-0029) for 30 seconds. Then, anti-PD1 antibodies were associated with 20 µg/mL for 120 seconds. The dissociation of anti-PD1 antibody was made in kinetics buffer for 120 seconds. Analysis data was made with the Blitz pro 1.2 software, which calculated association constant (ka) and dissociation constant (kd) and determined the affinity constant KD (ka/kd).

Affinity Measurement for PD1 by Biacore Method

The affinity measurement was performed by Biacore in PP21 platform (Inserm U1194, Université de Montpellier). Anti-human Fc antibody (GEHelthcare) was immobilized at 25µg/ml in acetate buffer pH5. Anti-human PD1 antibodies (Keytruda, Opdivo, HKLD variant, chimeric) was added at 1.25 nM and recombinant hPD1-His (Sino Biologicals, Beijing, China; reference 10377-H08H) was associated at different doses (6.25 nm to 200 nM) to calculate association constant (ka) and dissociation constant (kd) and to determine the affinity constant KD (ka/kd).

ELISA Antagonist: Competition Between PDL1 or PDL2 and Humanized Anti-PD1

Competitive ELISA assay was performed by PD-1: PD-L1 Inhibitor Screening ELISA Assay Pair (AcroBiosystems; USA; reference EP-101). In this assay, recombinant hPDL1 was immobilized on plastic at 2 µg/ml in PBS pH7.4 buffer. Purified antibody (at different concentrations) were mixed with 0.66 µg/ml final (fix concentration) of biotinylated Human PD1 (AcroBiosystems; USA; reference EP-101) to measure competitive binding for 2h at 37° C. After incubation and washing, peroxidase-labeled streptavidin (Vector Laboratories; USA; reference SA-5004) was added to detect Biotin-PD-1Fc binding and revealed by conventional methods. For the Competitive ELISA assay PDL-2/PD-1, a similar protocol was performed except that PD-L2 (SinoBiological, #10292-H02H) immobilized on plastic at 2 µg/mL in PBS pH7.4 buffer instead of PD-L1.

Blitz Method Competition with PDL1: PD1+acs+PDL1

This method was performed with a Blitz (Forté Bio; USA; reference C22-2 No 61010-1). Recombinant hPD1-His (Sino Biologicals, Beijing, China; reference 10377-H08H) was immobilized at 10 µg/ml by histidine tail into a Ni-NTA biosensor (Forté Bio; USA; reference 18-0029) for 30 seconds. In the second step, anti-PD1 antibodies were added at 20 µg/mL (saturating concentration) for 120 seconds. Then, human PDL1 (Sino Biologicals, Beijing, China; reference 10084-H02H) was associated at 100µg/mL, in competition with anti-PD1 antibodies, for 120 seconds. The dissociation of PDL1 was made in kinetics buffer for 120 seconds. Analysis data was made with the Blitz pro 1.2 software, which calculated association constant (ka) and dissociation constant (kd) and determined the affinity constant KD (ka/kd).

Competition Assay by Biacore to Measure Affinity Between PDL2 and PD1 Combined with the Humanized Anti-PD1 Variant Antibodies Affinity assessment by Biacore of PD-1 recombinant protein (SinoBiological, Beijing, China; reference 10377-H08H) pre-incubated with anti-PD1 antibodies on human PD-L2 recombinant protein (SinoBiological, 10292-H08H-B). Human recombinant PD-L2 was immobilized on the biosensor chip at a concentration 200 µg/mL. The biosensor chip was then treated with Ethanolamine 1M PH 8.4 for 10 min to inactivate free site. The complex antibody (200 nM)+recombinant human PD-1 (100 nM) was added and relative response was measured by Biacore. Data were calculated in % of relative response of interaction: 100%=PD-1 relative response.

Competition assay by Blitz method between PDL1 and humanized anti-PD1 variant antibodies on PD1.

This method was performed with a Blitz (Forté Bio; USA; reference C22-2 No 61010-1). Recombinant hPD1-His (Sino Biologicals, Beijing, China; reference 10377-H08H) was immobilized at 10 µg/ml by histidine tail into a Ni-NTA biosensor (Forté Bio; USA; reference 18-0029) for 30 seconds. In second step, PD1 was incubated with a humanized anti-PD1 variant antibody at 20 µg/mL (saturating concentration) for 120 seconds. Then, human PDL1 (Sino Biologicals, Beijing, China; reference 10084-H02H) was associated at 100 µg/mL, in competition with the humanized anti-PD1 antibody, for 120 seconds. The dissociation of PDL1 was made in kinetics buffer for 120 seconds. Analysis data was made with the Blitz pro 1.2 software, which calculated association constant (ka) and dissociation constant (kd) and determined the affinity constant KD (ka/kd).

Competition Assay by ELISA Between PD1 Combined with Different Concentration of the Humanized Anti-PD1 Variant Antibodies to PDL1 or PD-L2

Competitive ELISA assay was performed by PD-1: PD-L1 Inhibitor Screening ELISA Assay Pair (AcroBiosystems; USA; reference EP-101). In this assay, recombinant hPDL1 was immobilized on plastic at 2 µg/ml in PBS pH 7.4 buffer. Purified antibody (at different concentrations) were mixed with 0.66 µg/ml final (fix concentration) of biotinylated Human PD1 (AcroBiosystems; USA; reference EP-101) to measure competitive binding for 2h at 37° C. After incubation and washing, peroxidase-labeled streptavidin (Vector Laboratories; USA; reference SA-5004) was added to detect Biotin-PD-1Fc binding and revealed by conventional methods.

Stability Study by Exclusion Diffusion Chromatography

Stability study by exclusion diffusion chromatography was performed with a size-exclusion column (GE healthcare; Sweden, Superdex 200 10/300 GL; reference 17-5175-01) on AkTA Prime purification system (GE healthcare; Sweden). Anti-PD1 antibodies, incubated 7 days at 37° C. or at 4° C., were injected in this column (volume 100 µl) and eluted with PBS buffer on 30 ml. Analysis was made with PrimeView evaluation software ((GE healthcare; Sweden) to analyze the percentage of aggregates and monomers (retention time Tm=11.7-12 ml for monomers).

PD-1 Signaling Analysis Using DiscoverX Cell-Based Bioassay

The capacity of anti-PD-1 antibodies to blocks PD-1/pSHP-1 signaling was assessed with DiscoverX PathHunter® Jurkat PD-1 (SHP1) Signaling Assay (reference 93-1104C19). In this assay, Jurkat T cells stably express a chimeric PD-1 receptor fused to Beta-gal fragment (ED) and an engineered SHP1 fused to complementing Beta-gal fragment (EA). The coculture of Jurkat cells with PD-L1 presenting cells results in PD-1 phosphorylation, recruitment of engineered SHP-1 and the complementation of the ED and EA fragment creating an active Beta-gal enzyme and bioluminescence signal after substrate addition. Chemiluminescence is proportional to PD-1 signaling activation. The experiment was performed as per manufacturer recommendation. Briefly, PD-1+ Jurkat cells were incubated with different concentrations of anti PD-1 antibodies for 1 hour then cocultured with PD-L1+ cells for another hour. Detection reagent was added luminescence signal was read 180 minutes after using Tecan™ plate reader.

T Cell Activation Assay Using Promega Cell-Based Bioassay

The capacity of anti-PD-1 antibodies to restore T cell activation was tested using Promega PD-1/PD-L1 kit (Reference J1250). Two cell lines are used (1) Effector T cells (Jurkat stably expressing PD-1, NFAT-induced luciferase) and (2) activating target cells (CHO K1 cells stably expressing PDL1 and surface protein designed to stimulate cognate TCRs in an antigen-independent manner. When cells are cocultured, PD-L1 /PD-1 interaction inhibits TCR mediated activation thereby blocking NFAT activation and luciferase activity. The addition of an anti-PD-1 antibody blocks the PD-1 mediated inhibitory signal leading to NFAT activation and luciferase synthesis and emission of bioluminescence signal. The experiment was performed as per manufacturer recommendations. Serial dilutions of the PD-1 antibody were tested. Four hours following coculture of PD-L1+ target cells, PD-1 effector cells, and anti PD-1 antibodies, BioGlo™ luciferin substrate was added to the wells and plates were read using Tecan™ luminometer.

In Vitro Mixed Leukocyte Reaction Assay

Dendritic cells were differentiated from CD14+ monocytes isolated from human PBMCs (Miltenyi monocyte untouched classic kit isolation #130-117-337) by culturing for 6 days with 20 ng/ml granulocyte-macrophage-colony-stimulating factor and 20 ng/ml IL-4, and then mixed at a 1:10 ratio with allogeneic CD4+ T-cells isolated from healthy blood donors (Miltenyi isolation kit, #130-096-533). After 5 days of co-culture, supernatants were harvested; IFN-γ level was quantified by ELISA.

In Vivo Humanized PD1 Knock in Mouse Model

Efficacy of human anti PD-1 antibody was assessed in vivo in an orthotopic mesothelioma mouse model in immunocompetent mice genetically modified to express human PD-1 (exon 2). AK7 mesothelial cells were intrapleurally injected (3e6 cell/mouse) then treated at Day 5/8/12/15 with an anti PD-1 control or anti PD-1 humanized antibody (HKLD variant) at 1 mg/kg. Injected AK7 cells stably express luciferase allowing generation of in vivo bioluminescence signal following intraperitoneal injection of D-luciferin (3 μg/mouse, GoldBio, Saint Louis MO, USA, Reference 115144-35-9). Ten minutes following luciferin injection, bioluminescence signal was measured by Biospace Imager on the dorsal side and ventral side of the mouse during 1 minute. Data were analyzed in photon per second per cm2 per steradian and represent the mean of the dorsal and ventral signal. Each group represents mean+/−SEM of 5 to 7 mice per group. For the MC38 model, MC38 colon cancer cells were subcutaneously injected with 5e5 cells in the left flank. Tumor volume was calculated with the formula $0.52 \times (length \times width)^{1.5}$. Mice were treated when the tumor reached 80-100 mm$^3$ with 10mg/kg of anti-PD1 humanized antibody (HKLD variant) 3 times a week for 3 weeks. For the Hepa1.6 hepatocarcinoma, 2.5e6 Hepa1.6 hepatocarcinoma cells are injected into the portal vein. Mice were treated with 3 mg/kg of IgG4 isotype control or anti-PD1 humanized antibody (HKLD variant) on Day 4/7/11/14/18/21 following tumor injection.

Pharmacokinetics and Pharmacodynamics of the Humanized Anti-PD1 Antibody in Mice and Monkeys Cynomolgus monkeys were intravenously injected with a single dose of the humanized anti-PD1 antibody (HKLD variant), 1 or 5 mg/kg. Whole blood and sera were collected at multiple time points to assess receptor occupancy and quantify anti-PD1 antibody in the sera. To assess the pharmacokinetics of the humanized anti-PD-1 antibody in the sera of monkeys, PD-1 recombinant protein (Human PD-1-his tag recombinant protein (Sino Biological, #10377-H08H) was immobilized and diluted serum-containing anti-PD-1 antibody was added. Detection was performed with a sulflo-tagged mouse anti-human kappa antibody (clone NaM76-5F3, stained sulfloTag) was added and revealed by MSD Gold Read buffer (MSD #R92TG-2 and the MESO QUICKPLEX SQ 120 reader.

To assess Pharmacokinetics in mice, BalbcRJ (female 6-9 weeks) were intra-orbitally or subcutaneously injected with a single dose (5 mg/kg) of the chimeric form, the humanized anti PD-1 antibody (HKLD variant) or the Keytruda antibody. Plasma drug concentration was determined by ELISA using an immobilized anti-human light chain antibody (clone NaM76-5F3) diluted serum-containing anti-PD-1 antibody was added. Detection was performed with a peroxidase-labeled donkey anti-human IgG (Jackson Immunoresearch; USA; reference 709-035-149) was added and revealed by conventional methods.

Phagocytosis Assay

Human monocytes from healthy volunteers were in vitro differentiated into M0-macrophages with M-CSF (100 ng/mL) in complete RPMI media for 5 days. M0 macrophages were then cultivated for 2 days with human IFNg (70ng/mL) to generate M1-macrophages. M0/M1-macrophages and Raji cell line were stained with Cell Proliferation Dye eFluor450 (Invitrogen) and Cell Proliferation Dye eFluor670 (Invitrogen), respectively. Using Ultra Low attachment (ULA) 96-well bottom round plate, Raji CPDe670+ were pre-incubated with antibodies and Rituximab for 1 hour and M0 or M1-Macrophages CPDe450+ were added at an effector to target ratio of 2:1. Cells were both incubated for 1 or 2 hours. Phagocytosis analysis was performed by flow cytometry and the percentage of phagocytosis was calculated by the percentage of CPDe670+ cells in total CPDe450+ cells (i.e. percentage of double-positive cells (CPDe670+/CPDe450+)).

Ex Vivo Binding Analysis on Human Stimulated CD3+ PBMCs by Flow Cytofluorometry

To measure binding of anti-PD1 on human peripheral T cells, antibody was incubated for 30 min at 4° C., and washed before stained 30min at 4° C. with PE-labelled anti-human IgG Fc (Biolegend; USA; reference 409303)+Pacific Blue labeled anti-human CD3 (BD Biosciences clone SP34-2 #558124)Samples were analyzed on Cytoflex (Beckman Coulter) cytofluorometer in gating on CD3+ T cells.

IFNg Secretion by Human T Cells

Capacity of humanized anti PD-1 to stimulate secretion of IFNg effector cytokines was assessed in mixed allogeneic leukocyte reaction. Monocytes derived dendritic cells were generated from CD14+ isolated human peripheral blood monocytes+GM-CSF and IL-4 and cocultured with CD4+ isolated allogeneic human T cells (1 to 10 ratio) and different doses of HKLD variant or isotype control for 5 days. Supernatant containing IFNg cytokines were harvested and dosed by ELISA (BD Bioscience, reference 555142 and 555190).

We claim:

1. A pharmaceutical composition comprising a pharmaceutically acceptable carrier and a humanized monoclonal anti-human-PD-1 antibody or an antigen-binding fragment thereof comprising:
   (i) a heavy chain variable domain comprising HCDR1 comprising SEQ ID NO: 1, HCDR2 comprising SEQ ID NO: 2 and HCDR3 comprising SEQ ID NO: 9, and
   (ii) a light chain variable domain comprising LCDR1 comprising SEQ ID NO: 12, LCDR2 comprising SEQ ID NO: 13 and LCDR3 comprising SEQ ID NO: 14.

2. The pharmaceutical composition of claim 1, wherein the humanized monoclonal anti-human-PD-1 antibody or an antigen-binding fragment thereof comprises:
   (i) a heavy chain variable domain comprising HCDR1 consisting of SEQ ID NO: 1, HCDR2 consisting of SEQ ID NO: 2 and HCDR3 consisting of SEQ ID NO: 9, and
   (ii) a light chain variable domain comprising LCDR1 consisting of SEQ ID NO: 12, LCDR2 consisting of SEQ ID NO: 13 and LCDR3 consisting of SEQ ID NO: 14.

3. The pharmaceutical composition of claim 1, wherein the antibody or antigen-binding fragment thereof comprises a light chain constant domain derived from a human kappa light chain constant domain and a heavy chain constant domain derived from a human IgG1, IgG2, IgG3 or IgG4 heavy chain constant domain.

4. The pharmaceutical composition of claim 1, wherein the antibody or antigen-binding fragment thereof comprises a light chain constant domain derived from a human kappa light chain constant domain and a heavy chain constant domain derived from a human IgG1 heavy chain constant domain, optionally with a substitution or a combination of substitutions selected from the group consisting of T250Q/M428L; M252Y/S254T/T256E+H433K/N434F; E233P/L234V/L235A/G236A+A327G/A330S/P331S; E333A; S239D/A330L/I332E; P257I/Q311; K326W/E333S; S239D/I332E/G236A; N297A; L234A/L235A; N297A+M252Y/S254T/T256E; K322A and K444A, preferably selected from the group consisting of N297A optionally in combination with M252Y/S254T/T256E, and L234A/L235A.

5. The pharmaceutical composition of claim 1, wherein the antibody or antigen-binding fragment thereof comprises a light chain constant domain derived from a human kappa light chain constant domain and a heavy chain constant domain derived from a human IgG4 heavy chain constant domain, optionally with a substitution or a combination of substitutions selected from the group consisting of S228P; L234A/L235A, S228P+M252Y/S254T/T256E and K444A.

6. A method of treating cancer in a subject comprising administering a composition according to claim 1 to a subject having cancer, said cancer being selected from the group consisting of malignant mesothelioma, colorectal cancer and hepatocellular carcinoma.

7. The method of claim 6, wherein the cancer has tumor cells which are PD-L1 negative.

8. The method of claim 6, wherein said composition is administered in combination with radiotherapy or an additional therapeutic agent.

9. The method of claim 6, wherein the subject to be treated is immunosuppressed, immunocompromised or immunodepressed.

* * * * *